(12) United States Patent
Long

(10) Patent No.: US 9,233,241 B2
(45) Date of Patent: Jan. 12, 2016

(54) ELECTRICAL ABLATION DEVICES AND METHODS

(75) Inventor: Gary L. Long, Cincinnati, OH (US)

(73) Assignee: Ethicon Endo-Surgery, Inc., Cincinnati, OH (US)

(*) Notice: Subject to any disclaimer, the term of this patent is extended or adjusted under 35 U.S.C. 154(b) by 1020 days.

(21) Appl. No.: 13/352,495

(22) Filed: Jan. 18, 2012

(65) Prior Publication Data
US 2012/0220999 A1 Aug. 30, 2012

Related U.S. Application Data

(63) Continuation-in-part of application No. 13/036,908, filed on Feb. 28, 2011.

(51) Int. Cl.
| | |
|---|---|
| *A61B 18/18* | (2006.01) |
| *A61N 1/32* | (2006.01) |
| *A61B 18/12* | (2006.01) |
| *A61B 18/14* | (2006.01) |
| *A61B 18/00* | (2006.01) |

(52) U.S. Cl.
CPC ............ *A61N 1/327* (2013.01); *A61B 18/1206* (2013.01); *A61B 18/1492* (2013.01); *A61B 2018/00613* (2013.01)

(58) Field of Classification Search
CPC ........... A61B 18/1492; A61B 18/1477; A61B 2018/00577; A61B 18/1445; A61B 17/00234; A61B 1/00087; A61B 1/00135; A61B 1/018; A61B 2018/00613; A61B 2018/1425; A61B 2018/1475; A61B 17/3415; A61B 18/1206; A61B 18/1482; A61B 2018/00214
See application file for complete search history.

(56) References Cited

U.S. PATENT DOCUMENTS

| | | |
|---|---|---|
| 645,576 A | 3/1900 | Telsa |
| 649,621 A | 5/1900 | Tesla |
| 787,412 A | 4/1905 | Tesla |
| 1,039,354 A | 9/1912 | Bonadio |
| 1,127,948 A | 2/1915 | Wappler |
| 1,482,653 A | 2/1924 | Lilly |

(Continued)

FOREIGN PATENT DOCUMENTS

| | | |
|---|---|---|
| AU | 666310 B2 | 2/1996 |
| DE | 3008120 A1 | 9/1980 |

(Continued)

OTHER PUBLICATIONS

U.S. Appl. No. 13/036,908, filed Feb. 28, 2011.

(Continued)

*Primary Examiner* — Michael Peffley
*Assistant Examiner* — Amanda Zink

(57) ABSTRACT

A method for delivering energy to tissue having a necrotic threshold may generally comprise inserting an electrode array comprising a plurality of electrodes into the tissue, inserting a central electrode into the tissue, positioning a ground pad proximal to the tissue, applying a first sequence of electrical pulses to the electrode array less than the necrotic threshold to induce thermal heating in the tissue, applying a second sequence of electrical pulses to the central electrode equal to or greater than the necrotic threshold to induce cell necrosis in the tissue by irreversible electroporation, and applying a ground potential to the ground pad. Electrical ablation devices and systems and methods of using the same are also described herein.

23 Claims, 37 Drawing Sheets

(56) References Cited

U.S. PATENT DOCUMENTS

| | | |
|---|---|---|
| 1,625,602 A | 4/1927 | Gould et al. |
| 1,916,722 A | 7/1933 | Ende |
| 2,028,635 A | 1/1936 | Wappler |
| 2,031,682 A | 2/1936 | Wappler et al. |
| 2,113,246 A | 4/1938 | Wappler |
| 2,155,365 A | 4/1939 | Rankin |
| 2,191,858 A | 2/1940 | Moore |
| 2,196,620 A | 4/1940 | Attarian |
| 2,388,137 A | 10/1945 | Graumlich |
| 2,493,108 A | 1/1950 | Casey, Jr. |
| 2,504,152 A | 4/1950 | Riker et al. |
| 2,938,382 A | 5/1960 | De Graaf |
| 2,952,206 A | 9/1960 | Becksted |
| 3,069,195 A | 12/1962 | Buck |
| 3,070,088 A | 12/1962 | Brahos |
| 3,170,471 A | 2/1965 | Schnitzer |
| 3,435,824 A | 4/1969 | Gamponia |
| 3,470,876 A | 10/1969 | Barchilon |
| 3,595,239 A | 7/1971 | Petersen |
| 3,669,487 A | 6/1972 | Roberts et al. |
| 3,746,881 A | 7/1973 | Fitch et al. |
| 3,799,672 A | 3/1974 | Vurek |
| 3,854,473 A | 12/1974 | Matsuo |
| 3,946,740 A | 3/1976 | Bassett |
| 3,948,251 A | 4/1976 | Hosono |
| 3,961,632 A | 6/1976 | Moossun |
| 3,965,890 A | 6/1976 | Gauthier |
| 3,994,301 A | 11/1976 | Agris |
| 4,011,872 A | 3/1977 | Komiya |
| 4,012,812 A | 3/1977 | Black |
| 4,085,743 A | 4/1978 | Yoon |
| 4,164,225 A | 8/1979 | Johnson et al. |
| 4,174,715 A | 11/1979 | Hasson |
| 4,178,920 A | 12/1979 | Cawood, Jr. et al. |
| 4,207,873 A | 6/1980 | Kruy |
| 4,235,238 A | 11/1980 | Ogiu et al. |
| 4,258,716 A | 3/1981 | Sutherland |
| 4,269,174 A | 5/1981 | Adair |
| 4,278,077 A | 7/1981 | Mizumoto |
| 4,285,344 A | 8/1981 | Marshall |
| 4,311,143 A | 1/1982 | Komiya |
| 4,329,980 A | 5/1982 | Terada |
| 4,396,021 A | 8/1983 | Baumgartner |
| 4,406,656 A | 9/1983 | Hattler et al. |
| 4,452,246 A | 6/1984 | Bader et al. |
| 4,461,281 A | 7/1984 | Carson |
| 4,491,132 A | 1/1985 | Aikins |
| 4,527,331 A | 7/1985 | Lasner et al. |
| 4,527,564 A | 7/1985 | Eguchi et al. |
| 4,538,594 A | 9/1985 | Boebel et al. |
| D281,104 S | 10/1985 | Davison |
| 4,569,347 A | 2/1986 | Frisbie |
| 4,580,551 A | 4/1986 | Siegmund et al. |
| 4,646,722 A | 3/1987 | Silverstein et al. |
| 4,653,476 A | 3/1987 | Bonnet |
| 4,655,219 A | 4/1987 | Petruzzi |
| 4,669,470 A | 6/1987 | Brandfield |
| 4,671,477 A | 6/1987 | Cullen |
| 4,677,982 A | 7/1987 | Llinas et al. |
| 4,685,447 A | 8/1987 | Iversen et al. |
| 4,711,240 A | 12/1987 | Goldwasser et al. |
| 4,712,545 A | 12/1987 | Honkanen |
| 4,721,116 A | 1/1988 | Schintgen et al. |
| 4,727,600 A | 2/1988 | Avakian |
| 4,733,662 A | 3/1988 | DeSatnick et al. |
| D295,894 S | 5/1988 | Sharkany et al. |
| 4,763,669 A | 8/1988 | Jaeger |
| 4,770,188 A | 9/1988 | Chikama |
| 4,815,450 A | 3/1989 | Patel |
| 4,823,794 A | 4/1989 | Pierce |
| 4,829,999 A | 5/1989 | Auth |
| 4,867,140 A | 9/1989 | Hovis et al. |
| 4,869,238 A | 9/1989 | Opie et al. |
| 4,869,459 A | 9/1989 | Bourne |
| 4,873,979 A | 10/1989 | Hanna |
| 4,880,015 A | 11/1989 | Nierman |
| 4,911,148 A | 3/1990 | Sosnowski et al. |
| 4,926,860 A | 5/1990 | Stice et al. |
| 4,938,214 A | 7/1990 | Specht et al. |
| 4,950,273 A | 8/1990 | Briggs |
| 4,950,285 A | 8/1990 | Wilk |
| 4,953,539 A | 9/1990 | Nakamura et al. |
| 4,960,133 A | 10/1990 | Hewson |
| 4,977,887 A | 12/1990 | Gouda |
| 4,979,950 A | 12/1990 | Transue et al. |
| 4,984,581 A | 1/1991 | Stice |
| 4,994,079 A | 2/1991 | Genese et al. |
| 5,007,917 A | 4/1991 | Evans |
| 5,010,876 A | 4/1991 | Henley et al. |
| 5,020,514 A | 6/1991 | Heckele |
| 5,020,535 A | 6/1991 | Parker et al. |
| 5,025,778 A | 6/1991 | Silverstein et al. |
| 5,033,169 A | 7/1991 | Bindon |
| 5,037,433 A | 8/1991 | Wilk et al. |
| 5,041,129 A | 8/1991 | Hayhurst et al. |
| 5,046,513 A | 9/1991 | Gatturna et al. |
| 5,050,585 A | 9/1991 | Takahashi |
| 5,052,372 A | 10/1991 | Shapiro |
| 5,065,516 A | 11/1991 | Dulebohn |
| 5,066,295 A | 11/1991 | Kozak et al. |
| 5,108,421 A | 4/1992 | Fowler |
| 5,123,913 A | 6/1992 | Wilk et al. |
| 5,123,914 A | 6/1992 | Cope |
| 5,133,727 A | 7/1992 | Bales et al. |
| 5,147,374 A | 9/1992 | Fernandez |
| 5,174,300 A | 12/1992 | Bales et al. |
| 5,176,126 A | 1/1993 | Chikama |
| 5,190,050 A | 3/1993 | Nitzsche |
| 5,190,555 A | 3/1993 | Wetter et al. |
| 5,192,284 A | 3/1993 | Pleatman |
| 5,192,300 A | 3/1993 | Fowler |
| 5,197,963 A | 3/1993 | Parins |
| 5,201,752 A | 4/1993 | Brown et al. |
| 5,201,908 A | 4/1993 | Jones |
| 5,203,785 A | 4/1993 | Slater |
| 5,203,787 A | 4/1993 | Noblitt et al. |
| 5,209,747 A | 5/1993 | Knoepfler |
| 5,217,003 A | 6/1993 | Wilk |
| 5,217,453 A | 6/1993 | Wilk |
| 5,219,357 A | 6/1993 | Honkanen et al. |
| 5,219,358 A | 6/1993 | Bendel et al. |
| 5,222,362 A | 6/1993 | Maus et al. |
| 5,222,965 A | 6/1993 | Haughton |
| 5,234,437 A | 8/1993 | Sepetka |
| 5,234,453 A | 8/1993 | Smith et al. |
| 5,235,964 A | 8/1993 | Abenaim |
| 5,242,456 A | 9/1993 | Nash et al. |
| 5,245,460 A | 9/1993 | Allen et al. |
| 5,246,424 A | 9/1993 | Wilk |
| 5,257,999 A | 11/1993 | Slanetz, Jr. |
| 5,259,366 A | 11/1993 | Reydel et al. |
| 5,263,958 A | 11/1993 | deGuillebon et al. |
| 5,273,524 A | 12/1993 | Fox et al. |
| 5,275,607 A | 1/1994 | Lo et al. |
| 5,275,614 A | 1/1994 | Haber et al. |
| 5,275,616 A | 1/1994 | Fowler |
| 5,284,128 A | 2/1994 | Hart |
| 5,284,162 A | 2/1994 | Wilk |
| 5,287,845 A | 2/1994 | Faul et al. |
| 5,287,852 A | 2/1994 | Arkinstall |
| 5,290,299 A | 3/1994 | Fain et al. |
| 5,290,302 A | 3/1994 | Pericic |
| 5,295,977 A | 3/1994 | Cohen et al. |
| 5,297,536 A | 3/1994 | Wilk |
| 5,297,687 A | 3/1994 | Freed |
| 5,301,061 A | 4/1994 | Nakada et al. |
| 5,312,023 A | 5/1994 | Green et al. |
| 5,312,333 A | 5/1994 | Churinetz et al. |
| 5,312,351 A | 5/1994 | Gerrone |
| 5,312,416 A | 5/1994 | Spaeth et al. |
| 5,312,423 A | 5/1994 | Rosenbluth et al. |
| 5,318,589 A | 6/1994 | Lichtman |
| 5,320,636 A | 6/1994 | Slater |
| 5,324,261 A | 6/1994 | Amundson et al. |

(56) References Cited

U.S. PATENT DOCUMENTS

| | | |
|---|---|---|
| 5,325,845 A | 7/1994 | Adair |
| 5,330,471 A | 7/1994 | Eggers |
| 5,330,486 A | 7/1994 | Wilk |
| 5,330,488 A | 7/1994 | Goldrath |
| 5,330,496 A | 7/1994 | Alferness |
| 5,330,502 A | 7/1994 | Hassler et al. |
| 5,331,971 A | 7/1994 | Bales et al. |
| 5,334,168 A | 8/1994 | Hemmer |
| 5,334,198 A | 8/1994 | Hart et al. |
| 5,341,815 A | 8/1994 | Cofone et al. |
| 5,342,396 A | 8/1994 | Cook |
| 5,344,428 A | 9/1994 | Griffiths |
| 5,345,927 A | 9/1994 | Bonutti |
| 5,350,391 A | 9/1994 | Iacovelli |
| 5,352,184 A | 10/1994 | Goldberg et al. |
| 5,352,222 A | 10/1994 | Rydell |
| 5,354,302 A | 10/1994 | Ko |
| 5,354,311 A | 10/1994 | Kambin et al. |
| 5,356,381 A | 10/1994 | Ensminger et al. |
| 5,356,408 A | 10/1994 | Rydell |
| 5,360,428 A | 11/1994 | Hutchinson, Jr. |
| 5,364,408 A | 11/1994 | Gordon |
| 5,364,410 A | 11/1994 | Failla et al. |
| 5,366,466 A | 11/1994 | Christian et al. |
| 5,366,467 A | 11/1994 | Lynch et al. |
| 5,368,605 A | 11/1994 | Miller, Jr. |
| 5,370,647 A | 12/1994 | Graber et al. |
| 5,370,679 A | 12/1994 | Atlee, III |
| 5,374,273 A | 12/1994 | Nakao et al. |
| 5,374,275 A | 12/1994 | Bradley et al. |
| 5,374,277 A | 12/1994 | Hassler |
| 5,377,695 A | 1/1995 | An Haack |
| 5,383,877 A | 1/1995 | Clarke |
| 5,383,888 A | 1/1995 | Zvenyatsky et al. |
| 5,386,817 A | 2/1995 | Jones |
| 5,387,259 A | 2/1995 | Davidson |
| 5,391,174 A | 2/1995 | Weston |
| 5,392,789 A | 2/1995 | Slater et al. |
| 5,395,386 A | 3/1995 | Slater |
| 5,401,248 A | 3/1995 | Bencini |
| 5,403,311 A | 4/1995 | Abele et al. |
| 5,403,328 A | 4/1995 | Shallman |
| 5,403,342 A | 4/1995 | Tovey et al. |
| 5,403,348 A | 4/1995 | Bonutti |
| 5,405,073 A | 4/1995 | Porter |
| 5,405,359 A | 4/1995 | Pierce |
| 5,409,478 A | 4/1995 | Gerry et al. |
| 5,417,699 A | 5/1995 | Klein et al. |
| 5,423,821 A | 6/1995 | Pasque |
| 5,433,721 A | 7/1995 | Hooven et al. |
| 5,439,471 A | 8/1995 | Kerr |
| 5,439,478 A | 8/1995 | Palmer |
| 5,441,059 A | 8/1995 | Dannan |
| 5,441,494 A | 8/1995 | Ortiz |
| 5,441,499 A | 8/1995 | Fritzsch |
| 5,443,463 A | 8/1995 | Stern et al. |
| 5,445,638 A | 8/1995 | Rydell et al. |
| 5,445,648 A | 8/1995 | Cook |
| 5,449,021 A | 9/1995 | Chikama |
| 5,454,827 A | 10/1995 | Aust et al. |
| 5,456,667 A | 10/1995 | Ham et al. |
| 5,456,684 A | 10/1995 | Schmidt et al. |
| 5,458,131 A | 10/1995 | Wilk |
| 5,458,583 A | 10/1995 | McNeely et al. |
| 5,460,168 A | 10/1995 | Masubuchi et al. |
| 5,460,629 A | 10/1995 | Shlain et al. |
| 5,462,561 A | 10/1995 | Voda |
| 5,465,731 A | 11/1995 | Bell et al. |
| 5,467,763 A | 11/1995 | McMahon et al. |
| 5,468,250 A | 11/1995 | Paraschac et al. |
| 5,470,308 A | 11/1995 | Edwards et al. |
| 5,470,320 A | 11/1995 | Tiefenbrun et al. |
| 5,478,347 A | 12/1995 | Aranyi |
| 5,478,352 A | 12/1995 | Fowler |
| 5,480,404 A | 1/1996 | Kammerer et al. |
| 5,482,054 A | 1/1996 | Slater et al. |
| 5,484,451 A | 1/1996 | Akopov et al. |
| 5,489,256 A | 2/1996 | Adair |
| 5,496,347 A | 3/1996 | Hashiguchi et al. |
| 5,499,990 A | 3/1996 | Schülken et al. |
| 5,499,992 A | 3/1996 | Meade et al. |
| 5,501,692 A | 3/1996 | Riza |
| 5,503,616 A | 4/1996 | Jones |
| 5,505,686 A | 4/1996 | Willis et al. |
| 5,507,755 A | 4/1996 | Gresl et al. |
| 5,511,564 A | 4/1996 | Wilk |
| 5,514,157 A | 5/1996 | Nicholas et al. |
| 5,518,501 A | 5/1996 | Oneda et al. |
| 5,522,829 A | 6/1996 | Michalos |
| 5,522,830 A | 6/1996 | Aranyi |
| 5,527,321 A | 6/1996 | Hinchliffe |
| 5,533,418 A | 7/1996 | Wu et al. |
| 5,536,248 A | 7/1996 | Weaver et al. |
| 5,538,509 A | 7/1996 | Dunlap et al. |
| 5,540,648 A | 7/1996 | Yoon |
| 5,549,637 A | 8/1996 | Crainich |
| 5,554,151 A | 9/1996 | Hinchliffe |
| 5,555,883 A | 9/1996 | Avitall |
| 5,558,133 A | 9/1996 | Bortoli et al. |
| 5,562,693 A | 10/1996 | Devlin et al. |
| 5,569,243 A | 10/1996 | Kortenbach et al. |
| 5,569,298 A | 10/1996 | Schnell |
| 5,571,090 A | 11/1996 | Sherts |
| 5,573,540 A | 11/1996 | Yoon |
| 5,578,030 A | 11/1996 | Levin |
| 5,582,611 A | 12/1996 | Tsuruta et al. |
| 5,582,617 A | 12/1996 | Klieman et al. |
| 5,584,845 A | 12/1996 | Hart |
| 5,591,179 A | 1/1997 | Edelstein |
| 5,591,205 A | 1/1997 | Fowler |
| 5,593,420 A | 1/1997 | Eubanks, Jr et al. |
| 5,595,562 A | 1/1997 | Grier |
| 5,597,378 A | 1/1997 | Jervis |
| 5,601,573 A | 2/1997 | Fogelberg et al. |
| 5,601,588 A | 2/1997 | Tonomura et al. |
| 5,601,602 A | 2/1997 | Fowler |
| 5,604,531 A | 2/1997 | Iddan et al. |
| 5,607,389 A | 3/1997 | Edwards et al. |
| 5,607,406 A | 3/1997 | Hernandez et al. |
| 5,607,450 A | 3/1997 | Zvenyatsky et al. |
| 5,609,601 A | 3/1997 | Kolesa et al. |
| 5,613,975 A | 3/1997 | Christy |
| 5,616,117 A | 4/1997 | Dinkler et al. |
| 5,618,303 A | 4/1997 | Marlow et al. |
| 5,620,415 A | 4/1997 | Lucey et al. |
| 5,624,399 A | 4/1997 | Ackerman |
| 5,624,431 A | 4/1997 | Gerry et al. |
| 5,626,578 A | 5/1997 | Tihon |
| 5,628,732 A | 5/1997 | Antoon, Jr. et al. |
| 5,630,782 A | 5/1997 | Adair |
| 5,643,283 A | 7/1997 | Younker |
| 5,643,292 A | 7/1997 | Hart |
| 5,643,294 A | 7/1997 | Tovey et al. |
| 5,644,798 A | 7/1997 | Shah |
| 5,645,083 A | 7/1997 | Essig et al. |
| 5,645,565 A | 7/1997 | Rudd et al. |
| 5,649,372 A | 7/1997 | Souza |
| 5,653,677 A | 8/1997 | Okada et al. |
| 5,653,690 A | 8/1997 | Booth et al. |
| 5,653,722 A | 8/1997 | Kieturakis |
| 5,657,755 A | 8/1997 | Desai |
| 5,662,621 A | 9/1997 | Lafontaine |
| 5,662,663 A | 9/1997 | Shallman |
| 5,667,527 A | 9/1997 | Cook |
| 5,669,875 A | 9/1997 | van Eerdenburg |
| 5,681,324 A | 10/1997 | Kammerer et al. |
| 5,681,330 A | 10/1997 | Hughett et al. |
| 5,685,820 A | 11/1997 | Riek et al. |
| 5,690,606 A | 11/1997 | Slotman |
| 5,690,656 A | 11/1997 | Cope et al. |
| 5,690,660 A | 11/1997 | Kauker et al. |
| 5,695,448 A | 12/1997 | Kimura et al. |
| 5,695,505 A | 12/1997 | Yoon |
| 5,695,511 A | 12/1997 | Cano et al. |

(56) References Cited

U.S. PATENT DOCUMENTS

| | | |
|---|---|---|
| 5,700,275 A | 12/1997 | Bell et al. |
| 5,702,438 A | 12/1997 | Avitall |
| 5,704,892 A | 1/1998 | Adair |
| 5,709,708 A | 1/1998 | Thal |
| 5,711,921 A | 1/1998 | Langford |
| 5,716,326 A | 2/1998 | Dannan |
| 5,716,375 A | 2/1998 | Fowler |
| 5,728,094 A | 3/1998 | Edwards |
| 5,730,740 A | 3/1998 | Wales et al. |
| 5,735,849 A | 4/1998 | Baden et al. |
| 5,741,234 A | 4/1998 | Aboul-Hosn |
| 5,741,278 A | 4/1998 | Stevens |
| 5,741,285 A | 4/1998 | McBrayer et al. |
| 5,741,429 A | 4/1998 | Donadio, III et al. |
| 5,743,456 A | 4/1998 | Jones et al. |
| 5,746,759 A | 5/1998 | Meade et al. |
| 5,749,826 A | 5/1998 | Faulkner |
| 5,749,881 A | 5/1998 | Sackier et al. |
| 5,749,889 A | 5/1998 | Bacich et al. |
| 5,752,951 A | 5/1998 | Yanik |
| 5,755,731 A | 5/1998 | Grinberg |
| 5,762,604 A | 6/1998 | Kieturakis |
| 5,766,167 A | 6/1998 | Eggers et al. |
| 5,766,170 A | 6/1998 | Eggers |
| 5,766,205 A | 6/1998 | Zvenyatsky et al. |
| 5,769,849 A | 6/1998 | Eggers |
| 5,779,701 A | 7/1998 | McBrayer et al. |
| 5,779,716 A | 7/1998 | Cano et al. |
| 5,779,727 A | 7/1998 | Orejola |
| 5,782,859 A | 7/1998 | Nicholas et al. |
| 5,782,861 A | 7/1998 | Cragg et al. |
| 5,782,866 A | 7/1998 | Wenstrom, Jr. |
| 5,791,022 A | 8/1998 | Bohman |
| 5,792,113 A | 8/1998 | Kramer et al. |
| 5,792,153 A | 8/1998 | Swain et al. |
| 5,792,165 A | 8/1998 | Klieman et al. |
| 5,797,835 A | 8/1998 | Green |
| 5,797,928 A | 8/1998 | Kogasaka |
| 5,797,939 A | 8/1998 | Yoon |
| 5,797,941 A | 8/1998 | Schulze et al. |
| 5,797,959 A | 8/1998 | Castro et al. |
| 5,800,451 A | 9/1998 | Buess et al. |
| 5,803,903 A | 9/1998 | Athas et al. |
| 5,808,665 A | 9/1998 | Green |
| 5,810,806 A | 9/1998 | Ritchart et al. |
| 5,810,849 A | 9/1998 | Kontos |
| 5,810,865 A | 9/1998 | Koscher et al. |
| 5,810,876 A | 9/1998 | Kelleher |
| 5,810,877 A | 9/1998 | Roth et al. |
| 5,813,976 A | 9/1998 | Filipi et al. |
| 5,814,058 A | 9/1998 | Carlson et al. |
| 5,817,061 A | 10/1998 | Goodwin et al. |
| 5,817,107 A | 10/1998 | Schaller |
| 5,817,119 A | 10/1998 | Klieman et al. |
| 5,819,736 A | 10/1998 | Avny et al. |
| 5,823,947 A | 10/1998 | Yoon et al. |
| 5,824,071 A | 10/1998 | Nelson et al. |
| 5,827,276 A | 10/1998 | LeVeen et al. |
| 5,827,281 A | 10/1998 | Levin |
| 5,827,299 A | 10/1998 | Thomason et al. |
| 5,827,323 A | 10/1998 | Klieman et al. |
| 5,830,231 A | 11/1998 | Geiges, Jr. |
| 5,833,603 A | 11/1998 | Kovacs et al. |
| 5,833,700 A | 11/1998 | Fogelberg et al. |
| 5,833,703 A | 11/1998 | Manushakian |
| 5,836,960 A | 11/1998 | Kolesa et al. |
| 5,843,017 A | 12/1998 | Yoon |
| 5,843,121 A | 12/1998 | Yoon |
| 5,849,022 A | 12/1998 | Sakashita et al. |
| 5,853,374 A | 12/1998 | Hart et al. |
| 5,855,585 A | 1/1999 | Kontos |
| 5,860,913 A | 1/1999 | Yamaya et al. |
| 5,860,995 A | 1/1999 | Berkelaar |
| 5,868,762 A | 2/1999 | Cragg et al. |
| 5,873,849 A * | 2/1999 | Bernard .................. 604/20 |
| 5,876,411 A | 3/1999 | Kontos |
| 5,882,331 A | 3/1999 | Sasaki |
| 5,882,344 A | 3/1999 | Stouder, Jr. |
| 5,893,846 A | 4/1999 | Bales et al. |
| 5,893,874 A | 4/1999 | Bourque et al. |
| 5,893,875 A | 4/1999 | O'Connor et al. |
| 5,897,487 A | 4/1999 | Ouchi |
| 5,899,919 A | 5/1999 | Eubanks, Jr. et al. |
| 5,902,238 A | 5/1999 | Golden et al. |
| 5,902,254 A | 5/1999 | Magram |
| 5,904,702 A | 5/1999 | Ek et al. |
| 5,908,420 A | 6/1999 | Parins et al. |
| 5,908,429 A | 6/1999 | Yoon |
| 5,911,737 A | 6/1999 | Lee et al. |
| 5,916,146 A | 6/1999 | Allotta et al. |
| 5,916,147 A | 6/1999 | Boury |
| 5,921,993 A | 7/1999 | Yoon |
| 5,921,997 A | 7/1999 | Fogelberg et al. |
| 5,922,008 A | 7/1999 | Gimpelson |
| 5,925,052 A | 7/1999 | Simmons |
| 5,928,255 A | 7/1999 | Meade et al. |
| 5,928,266 A | 7/1999 | Kontos |
| 5,936,536 A | 8/1999 | Morris |
| 5,944,718 A | 8/1999 | Austin et al. |
| 5,951,547 A | 9/1999 | Gough et al. |
| 5,951,549 A | 9/1999 | Richardson et al. |
| 5,954,720 A | 9/1999 | Wilson et al. |
| 5,954,731 A | 9/1999 | Yoon |
| 5,957,936 A | 9/1999 | Yoon et al. |
| 5,957,943 A | 9/1999 | Vaitekunas |
| 5,957,953 A | 9/1999 | DiPoto et al. |
| 5,964,782 A | 10/1999 | Lafontaine et al. |
| 5,970,581 A | 10/1999 | Chadwick et al. |
| 5,971,995 A | 10/1999 | Rousseau |
| 5,972,002 A | 10/1999 | Bark et al. |
| 5,976,074 A | 11/1999 | Moriyama |
| 5,976,075 A | 11/1999 | Beane et al. |
| 5,976,130 A | 11/1999 | McBrayer et al. |
| 5,976,131 A | 11/1999 | Guglielmi et al. |
| 5,980,539 A | 11/1999 | Kontos |
| 5,980,556 A | 11/1999 | Giordano et al. |
| 5,984,938 A | 11/1999 | Yoon |
| 5,984,939 A | 11/1999 | Yoon |
| 5,984,950 A | 11/1999 | Cragg et al. |
| 5,989,182 A | 11/1999 | Hori et al. |
| 5,993,447 A | 11/1999 | Blewett et al. |
| 5,993,474 A | 11/1999 | Ouchi |
| 5,995,875 A | 11/1999 | Blewett et al. |
| 5,997,555 A | 12/1999 | Kontos |
| 6,001,120 A | 12/1999 | Levin |
| 6,004,269 A | 12/1999 | Crowley et al. |
| 6,004,330 A | 12/1999 | Middleman et al. |
| 6,007,566 A | 12/1999 | Wenstrom, Jr. |
| 6,010,515 A | 1/2000 | Swain et al. |
| 6,012,494 A | 1/2000 | Balazs |
| 6,016,452 A | 1/2000 | Kasevich |
| 6,017,356 A | 1/2000 | Frederick et al. |
| 6,019,770 A | 2/2000 | Christoudias |
| 6,024,708 A | 2/2000 | Bales et al. |
| 6,024,747 A | 2/2000 | Kontos |
| 6,027,522 A | 2/2000 | Palmer |
| 6,030,365 A | 2/2000 | Laufer |
| 6,030,384 A | 2/2000 | Nezhat |
| 6,030,634 A | 2/2000 | Wu et al. |
| 6,033,399 A | 3/2000 | Gines |
| 6,036,640 A | 3/2000 | Corace et al. |
| 6,036,685 A | 3/2000 | Mueller |
| 6,053,927 A | 4/2000 | Hamas |
| 6,053,937 A | 4/2000 | Edwards et al. |
| 6,066,160 A | 5/2000 | Colvin et al. |
| 6,068,603 A | 5/2000 | Suzuki |
| 6,068,629 A | 5/2000 | Haissaguerre et al. |
| 6,071,233 A | 6/2000 | Ishikawa et al. |
| 6,074,408 A | 6/2000 | Freeman |
| 6,086,530 A | 7/2000 | Mack |
| 6,090,105 A | 7/2000 | Zepeda et al. |
| 6,090,108 A | 7/2000 | McBrayer et al. |
| 6,090,129 A | 7/2000 | Ouchi |
| 6,096,046 A | 8/2000 | Weiss |

(56) References Cited

U.S. PATENT DOCUMENTS

| | | |
|---|---|---|
| 6,102,909 A | 8/2000 | Chen et al. |
| 6,102,926 A | 8/2000 | Tartaglia et al. |
| 6,106,473 A | 8/2000 | Violante et al. |
| 6,106,521 A | 8/2000 | Blewett et al. |
| 6,109,852 A | 8/2000 | Shahinpoor et al. |
| 6,110,154 A | 8/2000 | Shimomura et al. |
| 6,110,183 A | 8/2000 | Cope |
| 6,113,593 A | 9/2000 | Tu et al. |
| 6,117,144 A | 9/2000 | Nobles et al. |
| 6,117,158 A | 9/2000 | Measamer et al. |
| 6,139,555 A | 10/2000 | Hart et al. |
| 6,141,037 A | 10/2000 | Upton et al. |
| 6,146,391 A | 11/2000 | Cigaina |
| 6,148,222 A | 11/2000 | Ramsey, III |
| 6,149,653 A | 11/2000 | Deslauriers |
| 6,149,662 A | 11/2000 | Pugliesi et al. |
| 6,152,920 A | 11/2000 | Thompson et al. |
| 6,156,006 A | 12/2000 | Brosens et al. |
| 6,159,200 A | 12/2000 | Verdura et al. |
| 6,165,175 A | 12/2000 | Wampler et al. |
| 6,165,184 A | 12/2000 | Verdura et al. |
| 6,168,570 B1 | 1/2001 | Ferrera |
| 6,168,605 B1 | 1/2001 | Measamer et al. |
| 6,169,269 B1 | 1/2001 | Maynard |
| 6,170,130 B1 | 1/2001 | Hamilton et al. |
| 6,179,776 B1 | 1/2001 | Adams et al. |
| 6,179,832 B1 | 1/2001 | Jones et al. |
| 6,179,837 B1 | 1/2001 | Hooven |
| 6,183,420 B1 | 2/2001 | Douk et al. |
| 6,190,353 B1 | 2/2001 | Makower et al. |
| 6,190,383 B1 | 2/2001 | Schmaltz et al. |
| 6,190,384 B1 | 2/2001 | Ouchi |
| 6,190,399 B1 | 2/2001 | Palmer et al. |
| 6,203,533 B1 | 3/2001 | Ouchi |
| 6,206,872 B1 | 3/2001 | Lafond et al. |
| 6,206,877 B1 | 3/2001 | Kese et al. |
| 6,206,904 B1 | 3/2001 | Ouchi |
| 6,210,409 B1 | 4/2001 | Ellman et al. |
| 6,214,007 B1 | 4/2001 | Anderson |
| 6,214,028 B1 | 4/2001 | Yoon et al. |
| 6,216,043 B1 | 4/2001 | Swanson et al. |
| 6,228,096 B1 | 5/2001 | Marchand |
| 6,231,506 B1 | 5/2001 | Hu et al. |
| 6,234,958 B1 | 5/2001 | Snoke et al. |
| 6,245,079 B1 | 6/2001 | Nobles et al. |
| 6,246,914 B1 | 6/2001 | de la Rama et al. |
| 6,258,064 B1 | 7/2001 | Smith et al. |
| 6,261,242 B1 | 7/2001 | Roberts et al. |
| 6,264,664 B1 | 7/2001 | Avellanet |
| 6,270,497 B1 | 8/2001 | Sekino et al. |
| 6,270,505 B1 | 8/2001 | Yoshida et al. |
| 6,277,136 B1 | 8/2001 | Bonutti |
| 6,283,963 B1 | 9/2001 | Regula |
| 6,293,909 B1 | 9/2001 | Chu et al. |
| 6,293,952 B1 | 9/2001 | Brosens et al. |
| 6,296,630 B1 | 10/2001 | Altman et al. |
| 6,314,963 B1 | 11/2001 | Vaska et al. |
| 6,322,578 B1 | 11/2001 | Houle et al. |
| 6,325,534 B1 | 12/2001 | Hawley et al. |
| 6,326,177 B1 | 12/2001 | Schoenbach et al. |
| 6,328,730 B1 | 12/2001 | Harkrider, Jr. |
| 6,350,267 B1 | 2/2002 | Stefanchik |
| 6,350,278 B1 | 2/2002 | Lenker et al. |
| 6,352,503 B1 | 3/2002 | Matsui et al. |
| 6,352,543 B1 | 3/2002 | Cole |
| 6,355,013 B1 | 3/2002 | van Muiden |
| 6,355,035 B1 | 3/2002 | Manushakian |
| 6,361,534 B1 | 3/2002 | Chen et al. |
| 6,364,879 B1 | 4/2002 | Chen et al. |
| 6,368,340 B2 | 4/2002 | Malecki et al. |
| 6,371,956 B1 | 4/2002 | Wilson et al. |
| 6,379,366 B1 | 4/2002 | Fleischman et al. |
| 6,383,195 B1 | 5/2002 | Richard |
| 6,383,197 B1 | 5/2002 | Conlon et al. |
| 6,387,671 B1 | 5/2002 | Rubinsky et al. |
| 6,391,029 B1 | 5/2002 | Hooven et al. |
| 6,398,708 B1 | 6/2002 | Hastings et al. |
| 6,402,735 B1 | 6/2002 | Langevin |
| 6,402,746 B1 | 6/2002 | Whayne et al. |
| 6,406,440 B1 | 6/2002 | Stefanchik |
| 6,409,727 B1 | 6/2002 | Bales et al. |
| 6,409,733 B1 | 6/2002 | Conlon et al. |
| 6,419,639 B2 | 7/2002 | Walther et al. |
| 6,419,641 B1 | 7/2002 | Mark et al. |
| 6,427,089 B1 | 7/2002 | Knowlton |
| 6,431,500 B1 | 8/2002 | Jacobs et al. |
| 6,436,107 B1 | 8/2002 | Wang et al. |
| 6,443,970 B1 | 9/2002 | Schulze et al. |
| 6,443,988 B2 | 9/2002 | Felt et al. |
| 6,447,511 B1 | 9/2002 | Slater |
| 6,447,523 B1 | 9/2002 | Middleman et al. |
| 6,454,783 B1 | 9/2002 | Piskun |
| 6,454,785 B2 | 9/2002 | De Hoyos Garza |
| 6,458,076 B1 | 10/2002 | Pruitt |
| 6,464,701 B1 | 10/2002 | Hooven et al. |
| 6,464,702 B2 | 10/2002 | Schulze et al. |
| 6,470,218 B1 | 10/2002 | Behl |
| 6,475,104 B1 | 11/2002 | Lutz et al. |
| 6,485,411 B1 | 11/2002 | Konstorum et al. |
| 6,489,745 B1 | 12/2002 | Koreis |
| 6,491,626 B1 | 12/2002 | Stone et al. |
| 6,491,627 B1 | 12/2002 | Komi |
| 6,491,691 B1 | 12/2002 | Morley et al. |
| 6,493,590 B1 | 12/2002 | Wessman et al. |
| 6,494,893 B2 | 12/2002 | Dubrul et al. |
| 6,500,176 B1 | 12/2002 | Truckai et al. |
| 6,503,192 B1 | 1/2003 | Ouchi |
| 6,506,190 B1 | 1/2003 | Walshe |
| 6,508,827 B1 | 1/2003 | Manhes |
| 6,514,239 B2 | 2/2003 | Shimmura et al. |
| 6,520,954 B2 | 2/2003 | Ouchi |
| 6,526,320 B2 | 2/2003 | Mitchell |
| 6,527,782 B2 | 3/2003 | Hogg et al. |
| 6,530,922 B2 | 3/2003 | Cosman et al. |
| 6,535,764 B2 | 3/2003 | Imran et al. |
| 6,537,200 B2 | 3/2003 | Leysieffer et al. |
| 6,543,456 B1 | 4/2003 | Freeman |
| 6,551,270 B1 | 4/2003 | Bimbo et al. |
| 6,554,766 B2 | 4/2003 | Maeda et al. |
| 6,554,823 B2 | 4/2003 | Palmer et al. |
| 6,554,829 B2 | 4/2003 | Schulze et al. |
| 6,558,384 B2 | 5/2003 | Mayenberger |
| 6,562,034 B2 | 5/2003 | Edwards et al. |
| 6,562,035 B1 | 5/2003 | Levin |
| 6,562,052 B2 | 5/2003 | Nobles et al. |
| 6,569,159 B1 | 5/2003 | Edwards et al. |
| 6,572,629 B2 | 6/2003 | Kalloo et al. |
| 6,572,635 B1 | 6/2003 | Bonutti |
| 6,575,988 B2 | 6/2003 | Rousseau |
| 6,579,311 B1 | 6/2003 | Makower |
| 6,581,889 B2 | 6/2003 | Carpenter et al. |
| 6,585,642 B2 | 7/2003 | Christopher |
| 6,585,717 B1 | 7/2003 | Wittenberger et al. |
| 6,587,750 B2 | 7/2003 | Gerbi et al. |
| 6,592,559 B1 | 7/2003 | Pakter et al. |
| 6,592,603 B2 | 7/2003 | Lasner |
| 6,602,262 B2 | 8/2003 | Griego et al. |
| 6,605,105 B1 | 8/2003 | Cuschieri et al. |
| 6,610,072 B1 | 8/2003 | Christy et al. |
| 6,610,074 B2 | 8/2003 | Santilli |
| 6,613,038 B2 | 9/2003 | Bonutti et al. |
| 6,613,068 B2 | 9/2003 | Ouchi |
| 6,616,632 B2 | 9/2003 | Sharp et al. |
| 6,620,193 B1 | 9/2003 | Lau et al. |
| 6,623,448 B2 | 9/2003 | Slater |
| 6,626,919 B1 | 9/2003 | Swanstrom |
| 6,632,229 B1 | 10/2003 | Yamanouchi |
| 6,632,234 B2 | 10/2003 | Kieturakis et al. |
| 6,638,275 B1 | 10/2003 | McGaffigan et al. |
| 6,638,286 B1 | 10/2003 | Burbank et al. |
| 6,645,225 B1 | 11/2003 | Atkinson |
| 6,652,518 B2 | 11/2003 | Wellman et al. |
| 6,652,521 B2 | 11/2003 | Schulze |
| 6,652,551 B1 | 11/2003 | Heiss |

(56) References Cited

U.S. PATENT DOCUMENTS

| | | |
|---|---|---|
| 6,656,194 B1 | 12/2003 | Gannoe et al. |
| 6,663,641 B1 | 12/2003 | Kovac et al. |
| 6,663,655 B2 | 12/2003 | Ginn et al. |
| 6,666,854 B1 | 12/2003 | Lange |
| 6,672,338 B1 | 1/2004 | Esashi et al. |
| 6,673,058 B2 | 1/2004 | Snow |
| 6,673,087 B1 | 1/2004 | Chang et al. |
| 6,673,092 B1 | 1/2004 | Bacher |
| 6,679,882 B1 | 1/2004 | Kornerup |
| 6,685,628 B2 | 2/2004 | Vu |
| 6,685,724 B1 | 2/2004 | Haluck |
| 6,692,445 B2 | 2/2004 | Roberts et al. |
| 6,692,462 B2 | 2/2004 | Mackenzie et al. |
| 6,692,493 B2 | 2/2004 | McGovern et al. |
| 6,699,180 B2 | 3/2004 | Kobayashi |
| 6,699,256 B1 | 3/2004 | Logan et al. |
| 6,699,263 B2 | 3/2004 | Cope |
| 6,706,018 B2 | 3/2004 | Westlund et al. |
| 6,708,066 B2 | 3/2004 | Herbst et al. |
| 6,709,188 B2 | 3/2004 | Ushimaru |
| 6,709,445 B2 | 3/2004 | Boebel et al. |
| 6,716,226 B2 | 4/2004 | Sixto, Jr. et al. |
| 6,731,875 B1 | 5/2004 | Kartalopoulos |
| 6,736,822 B2 | 5/2004 | McClellan et al. |
| 6,740,030 B2 | 5/2004 | Martone et al. |
| 6,743,166 B2 | 6/2004 | Berci et al. |
| 6,743,226 B2 | 6/2004 | Cosman et al. |
| 6,743,239 B1 | 6/2004 | Kuehn et al. |
| 6,743,240 B2 | 6/2004 | Smith et al. |
| 6,749,560 B1 | 6/2004 | Konstorum et al. |
| 6,749,609 B1 | 6/2004 | Lunsford et al. |
| 6,752,768 B2 | 6/2004 | Burdorff et al. |
| 6,752,811 B2 | 6/2004 | Chu et al. |
| 6,752,822 B2 | 6/2004 | Jespersen |
| 6,758,857 B2 | 7/2004 | Cioanta et al. |
| 6,761,685 B2 | 7/2004 | Adams et al. |
| 6,761,718 B2 | 7/2004 | Madsen |
| 6,761,722 B2 | 7/2004 | Cole et al. |
| 6,773,434 B2 | 8/2004 | Ciarrocca |
| 6,776,787 B2 | 8/2004 | Phung et al. |
| 6,780,151 B2 | 8/2004 | Grabover et al. |
| 6,780,352 B2 | 8/2004 | Jacobson |
| 6,783,491 B2 | 8/2004 | Saadat et al. |
| 6,786,382 B1 | 9/2004 | Hoffman |
| 6,786,864 B2 | 9/2004 | Matsuura et al. |
| 6,786,905 B2 | 9/2004 | Swanson et al. |
| 6,788,977 B2 | 9/2004 | Fenn et al. |
| 6,790,173 B2 | 9/2004 | Saadat et al. |
| 6,790,217 B2 | 9/2004 | Schulze et al. |
| 6,795,728 B2 | 9/2004 | Chornenky et al. |
| 6,800,056 B2 | 10/2004 | Tartaglia et al. |
| 6,808,491 B2 | 10/2004 | Kortenbach et al. |
| 6,817,974 B2 | 11/2004 | Cooper et al. |
| 6,818,007 B1 | 11/2004 | Dampney et al. |
| 6,824,548 B2 | 11/2004 | Smith et al. |
| 6,830,545 B2 | 12/2004 | Bendall |
| 6,836,688 B2 | 12/2004 | Ingle et al. |
| 6,837,847 B2 | 1/2005 | Ewers et al. |
| 6,840,246 B2 | 1/2005 | Downing |
| 6,840,938 B1 | 1/2005 | Morley et al. |
| 6,843,794 B2 | 1/2005 | Sixto, Jr. et al. |
| 6,861,250 B1 | 3/2005 | Cole et al. |
| 6,866,627 B2 | 3/2005 | Nozue |
| 6,866,628 B2 | 3/2005 | Goodman et al. |
| 6,869,394 B2 | 3/2005 | Ishibiki |
| 6,878,106 B1 | 4/2005 | Herrmann |
| 6,878,110 B2 | 4/2005 | Yang et al. |
| 6,881,213 B2 | 4/2005 | Ryan et al. |
| 6,881,216 B2 | 4/2005 | Di Caprio et al. |
| 6,884,213 B2 | 4/2005 | Raz et al. |
| 6,887,255 B2 | 5/2005 | Shimm |
| 6,889,089 B2 | 5/2005 | Behl et al. |
| 6,896,683 B1 | 5/2005 | Gadberry et al. |
| 6,896,692 B2 | 5/2005 | Ginn et al. |
| 6,899,710 B2 | 5/2005 | Hooven |
| 6,908,427 B2 | 6/2005 | Fleener et al. |
| 6,908,476 B2 | 6/2005 | Jud et al. |
| 6,913,613 B2 | 7/2005 | Schwarz et al. |
| 6,916,284 B2 | 7/2005 | Moriyama |
| 6,918,871 B2 | 7/2005 | Schulze |
| 6,918,908 B2 | 7/2005 | Bonner et al. |
| 6,926,725 B2 | 8/2005 | Cooke et al. |
| 6,932,810 B2 | 8/2005 | Ryan |
| 6,932,824 B1 | 8/2005 | Roop et al. |
| 6,932,827 B2 | 8/2005 | Cole |
| 6,932,834 B2 | 8/2005 | Lizardi et al. |
| 6,936,003 B2 | 8/2005 | Iddan |
| 6,939,327 B2 | 9/2005 | Hall et al. |
| 6,942,613 B2 | 9/2005 | Ewers et al. |
| 6,944,490 B1 | 9/2005 | Chow |
| 6,945,472 B2 | 9/2005 | Wuttke et al. |
| 6,945,979 B2 | 9/2005 | Kortenbach et al. |
| 6,955,683 B2 | 10/2005 | Bonutti |
| 6,958,035 B2 | 10/2005 | Friedman et al. |
| 6,960,162 B2 | 11/2005 | Saadat et al. |
| 6,960,163 B2 | 11/2005 | Ewers et al. |
| 6,962,587 B2 | 11/2005 | Johnson et al. |
| 6,964,662 B2 | 11/2005 | Kidooka |
| 6,966,909 B2 | 11/2005 | Marshall et al. |
| 6,966,919 B2 | 11/2005 | Sixto, Jr. et al. |
| 6,967,462 B1 | 11/2005 | Landis |
| 6,971,988 B2 | 12/2005 | Orban, III |
| 6,972,017 B2 | 12/2005 | Smith et al. |
| 6,974,411 B2 | 12/2005 | Belson |
| 6,976,992 B2 | 12/2005 | Sachatello et al. |
| 6,984,203 B2 | 1/2006 | Tartaglia et al. |
| 6,984,205 B2 | 1/2006 | Gazdzinski |
| 6,986,774 B2 | 1/2006 | Middleman et al. |
| 6,988,987 B2 | 1/2006 | Ishikawa et al. |
| 6,989,028 B2 | 1/2006 | Lashinski et al. |
| 6,991,627 B2 | 1/2006 | Madhani et al. |
| 6,991,631 B2 | 1/2006 | Woloszko et al. |
| 6,994,708 B2 | 2/2006 | Manzo |
| 6,997,931 B2 | 2/2006 | Sauer et al. |
| 7,000,818 B2 | 2/2006 | Shelton, IV et al. |
| 7,001,341 B2 | 2/2006 | Gellman et al. |
| 7,008,375 B2 | 3/2006 | Weisel |
| 7,008,419 B2 | 3/2006 | Shadduck |
| 7,009,634 B2 | 3/2006 | Iddan et al. |
| 7,010,340 B2 | 3/2006 | Scarantino et al. |
| 7,020,531 B1 | 3/2006 | Colliou et al. |
| 7,025,580 B2 | 4/2006 | Heagy et al. |
| 7,029,435 B2 | 4/2006 | Nakao |
| 7,029,438 B2 | 4/2006 | Morin et al. |
| 7,029,450 B2 | 4/2006 | Gellman |
| 7,032,600 B2 | 4/2006 | Fukuda et al. |
| 7,035,680 B2 | 4/2006 | Partridge et al. |
| 7,037,290 B2 | 5/2006 | Gardeski et al. |
| 7,041,052 B2 | 5/2006 | Saadat et al. |
| 7,052,489 B2 | 5/2006 | Griego et al. |
| 7,060,024 B2 | 6/2006 | Long et al. |
| 7,060,025 B2 | 6/2006 | Long et al. |
| 7,063,697 B2 | 6/2006 | Slater |
| 7,063,715 B2 | 6/2006 | Onuki et al. |
| 7,066,879 B2 | 6/2006 | Fowler et al. |
| 7,066,936 B2 | 6/2006 | Ryan |
| 7,070,602 B2 | 7/2006 | Smith et al. |
| 7,076,305 B2 | 7/2006 | Imran et al. |
| 7,083,618 B2 | 8/2006 | Couture et al. |
| 7,083,620 B2 | 8/2006 | Jahns et al. |
| 7,083,629 B2 | 8/2006 | Weller et al. |
| 7,083,635 B2 | 8/2006 | Ginn |
| 7,087,071 B2 | 8/2006 | Nicholas et al. |
| 7,088,923 B2 | 8/2006 | Haruyama |
| 7,090,673 B2 | 8/2006 | Dycus et al. |
| 7,090,683 B2 | 8/2006 | Brock et al. |
| 7,090,685 B2 | 8/2006 | Kortenbach et al. |
| 7,093,518 B2 | 8/2006 | Gmeilbauer |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,105,000 B2 | 9/2006 | McBrayer |
| 7,105,005 B2 | 9/2006 | Blake |
| 7,108,696 B2 | 9/2006 | Daniel et al. |

(56) References Cited

U.S. PATENT DOCUMENTS

| | | |
|---|---|---|
| 7,108,703 B2 | 9/2006 | Danitz et al. |
| 7,112,208 B2 | 9/2006 | Morris et al. |
| 7,115,092 B2 | 10/2006 | Park et al. |
| 7,115,124 B1 | 10/2006 | Xiao |
| 7,117,703 B2 | 10/2006 | Kato et al. |
| 7,118,531 B2 | 10/2006 | Krill |
| 7,118,578 B2 | 10/2006 | West, Jr. et al. |
| 7,118,587 B2 | 10/2006 | Dycus et al. |
| 7,128,708 B2 | 10/2006 | Saadat et al. |
| 7,130,697 B2 | 10/2006 | Chornenky et al. |
| RE39,415 E | 11/2006 | Bales et al. |
| 7,131,978 B2 | 11/2006 | Sancoff et al. |
| 7,131,979 B2 | 11/2006 | DiCarlo et al. |
| 7,131,980 B1 | 11/2006 | Field et al. |
| 7,137,980 B2 | 11/2006 | Buysse et al. |
| 7,137,981 B2 | 11/2006 | Long |
| 7,146,984 B2 | 12/2006 | Stack et al. |
| 7,147,650 B2 | 12/2006 | Lee |
| 7,150,097 B2 | 12/2006 | Sremcich et al. |
| 7,150,655 B2 | 12/2006 | Mastrototaro et al. |
| 7,150,750 B2 | 12/2006 | Damarati |
| 7,152,488 B2 | 12/2006 | Hedrich et al. |
| 7,153,321 B2 | 12/2006 | Andrews |
| 7,160,296 B2 | 1/2007 | Pearson et al. |
| 7,163,525 B2 | 1/2007 | Franer |
| 7,172,714 B2 | 2/2007 | Jacobson |
| 7,179,254 B2 | 2/2007 | Pendekanti et al. |
| 7,188,627 B2 | 3/2007 | Nelson et al. |
| 7,195,612 B2 | 3/2007 | Van Sloten et al. |
| 7,195,631 B2 | 3/2007 | Dumbauld |
| 7,204,820 B2 | 4/2007 | Akahoshi |
| 7,208,005 B2 | 4/2007 | Frecker et al. |
| 7,211,092 B2 | 5/2007 | Hughett |
| 7,220,227 B2 | 5/2007 | Sasaki et al. |
| 7,223,272 B2 | 5/2007 | Francere et al. |
| 7,229,438 B2 | 6/2007 | Young |
| 7,232,414 B2 | 6/2007 | Gonzalez |
| 7,232,445 B2 | 6/2007 | Kortenbach et al. |
| 7,235,089 B1 | 6/2007 | McGuckin, Jr. |
| 7,241,290 B2 | 7/2007 | Doyle et al. |
| 7,244,228 B2 | 7/2007 | Lubowski |
| 7,250,027 B2 | 7/2007 | Barry |
| 7,252,660 B2 | 8/2007 | Kunz |
| 7,255,675 B2 | 8/2007 | Gertner et al. |
| 7,261,725 B2 | 8/2007 | Binmoeller |
| 7,270,663 B2 | 9/2007 | Nakao |
| 7,288,075 B2 | 10/2007 | Parihar et al. |
| 7,291,127 B2 | 11/2007 | Eidenschink |
| 7,294,139 B1 | 11/2007 | Gengler |
| 7,301,250 B2 | 11/2007 | Cassel |
| 7,306,597 B2 | 12/2007 | Manzo |
| 7,308,828 B2 | 12/2007 | Hashimoto |
| 7,318,802 B2 | 1/2008 | Suzuki et al. |
| 7,320,695 B2 | 1/2008 | Carroll |
| 7,322,934 B2 | 1/2008 | Miyake et al. |
| 7,323,006 B2 | 1/2008 | Andreas et al. |
| 7,329,256 B2 | 2/2008 | Johnson et al. |
| 7,329,257 B2 | 2/2008 | Kanehira et al. |
| 7,329,383 B2 | 2/2008 | Stinson |
| 7,335,220 B2 | 2/2008 | Khosravi et al. |
| 7,344,536 B1 | 3/2008 | Lunsford et al. |
| 7,352,387 B2 | 4/2008 | Yamamoto |
| 7,364,582 B2 | 4/2008 | Lee |
| 7,371,215 B2 | 5/2008 | Colliou et al. |
| 7,381,216 B2 | 6/2008 | Buzzard et al. |
| 7,390,324 B2 | 6/2008 | Whalen et al. |
| 7,393,322 B2 | 7/2008 | Wenchell |
| 7,402,162 B2 | 7/2008 | Ouchi |
| 7,404,791 B2 | 7/2008 | Linares et al. |
| 7,410,483 B2 | 8/2008 | Danitz et al. |
| 7,413,563 B2 | 8/2008 | Corcoran et al. |
| 7,416,554 B2 | 8/2008 | Lam et al. |
| 7,422,590 B2 | 9/2008 | Kupferschmid et al. |
| 7,435,229 B2 | 10/2008 | Wolf |
| 7,435,257 B2 | 10/2008 | Lashinski et al. |
| 7,452,327 B2 | 11/2008 | Durgin et al. |
| 7,455,208 B2 | 11/2008 | Wales et al. |
| 7,468,066 B2 | 12/2008 | Vargas et al. |
| 7,476,237 B2 | 1/2009 | Taniguchi et al. |
| 7,485,093 B2 | 2/2009 | Glukhovsky |
| 7,488,295 B2 | 2/2009 | Burbank et al. |
| 7,494,499 B2 | 2/2009 | Nagase et al. |
| 7,497,867 B2 | 3/2009 | Lasner et al. |
| 7,498,950 B1 | 3/2009 | Ertas et al. |
| 7,507,200 B2 | 3/2009 | Okada |
| 7,510,107 B2 | 3/2009 | Timm et al. |
| 7,511,733 B2 | 3/2009 | Takizawa et al. |
| 7,515,953 B2 | 4/2009 | Madar et al. |
| 7,520,876 B2 | 4/2009 | Ressemann et al. |
| 7,524,281 B2 | 4/2009 | Chu et al. |
| 7,524,302 B2 | 4/2009 | Tower |
| 7,534,228 B2 | 5/2009 | Williams |
| 7,540,872 B2 | 6/2009 | Schechter et al. |
| 7,542,807 B2 | 6/2009 | Bertolero et al. |
| 7,544,203 B2 | 6/2009 | Chin et al. |
| 7,548,040 B2 | 6/2009 | Lee et al. |
| 7,549,564 B2 | 6/2009 | Boudreaux |
| 7,549,998 B2 | 6/2009 | Braun |
| 7,553,278 B2 | 6/2009 | Kucklick |
| 7,553,298 B2 | 6/2009 | Hunt et al. |
| 7,559,452 B2 | 7/2009 | Wales et al. |
| 7,559,887 B2 | 7/2009 | Dannan |
| 7,559,916 B2 | 7/2009 | Smith et al. |
| 7,560,006 B2 | 7/2009 | Rakos et al. |
| 7,561,907 B2 | 7/2009 | Fuimaono et al. |
| 7,561,916 B2 | 7/2009 | Hunt et al. |
| 7,566,334 B2 | 7/2009 | Christian et al. |
| 7,575,144 B2 | 8/2009 | Ortiz et al. |
| 7,575,548 B2 | 8/2009 | Takemoto et al. |
| 7,579,550 B2 | 8/2009 | Dayton et al. |
| 7,582,096 B2 | 9/2009 | Gellman et al. |
| 7,588,177 B2 | 9/2009 | Racenet |
| 7,588,557 B2 | 9/2009 | Nakao |
| 7,597,229 B2 | 10/2009 | Boudreaux et al. |
| 7,604,150 B2 | 10/2009 | Boudreaux |
| 7,608,083 B2 | 10/2009 | Lee et al. |
| 7,611,479 B2 | 11/2009 | Cragg et al. |
| 7,618,398 B2 | 11/2009 | Holman et al. |
| 7,621,936 B2 | 11/2009 | Cragg et al. |
| 7,632,250 B2 | 12/2009 | Smith et al. |
| 7,635,373 B2 | 12/2009 | Ortiz |
| 7,637,903 B2 | 12/2009 | Lentz et al. |
| 7,648,519 B2 | 1/2010 | Lee et al. |
| 7,650,742 B2 | 1/2010 | Ushijima |
| 7,651,483 B2 | 1/2010 | Byrum et al. |
| 7,651,509 B2 | 1/2010 | Bojarski et al. |
| 7,654,431 B2 | 2/2010 | Hueil et al. |
| 7,655,004 B2 | 2/2010 | Long |
| 7,662,089 B2 | 2/2010 | Okada et al. |
| 7,666,180 B2 | 2/2010 | Holsten et al. |
| 7,666,203 B2 | 2/2010 | Chanduszko et al. |
| 7,670,336 B2 | 3/2010 | Young et al. |
| 7,674,259 B2 | 3/2010 | Shadduck |
| 7,678,043 B2 | 3/2010 | Gilad |
| 7,680,543 B2 | 3/2010 | Azure |
| 7,684,599 B2 | 3/2010 | Horn et al. |
| 7,686,826 B2 | 3/2010 | Lee et al. |
| 7,697,970 B2 | 4/2010 | Uchiyama et al. |
| 7,699,835 B2 | 4/2010 | Lee et al. |
| 7,699,864 B2 | 4/2010 | Kick et al. |
| 7,713,189 B2 | 5/2010 | Hanke |
| 7,713,270 B2 | 5/2010 | Suzuki |
| 7,721,742 B2 | 5/2010 | Kalloo et al. |
| 7,736,374 B2 | 6/2010 | Vaughan et al. |
| 7,744,615 B2 | 6/2010 | Couture |
| 7,749,161 B2 | 7/2010 | Beckman et al. |
| 7,753,933 B2 | 7/2010 | Ginn et al. |
| 7,758,577 B2 | 7/2010 | Nobis et al. |
| 7,762,949 B2 | 7/2010 | Nakao |
| 7,762,998 B2 | 7/2010 | Birk et al. |
| 7,763,012 B2 | 7/2010 | Petrick et al. |
| 7,765,010 B2 | 7/2010 | Chornenky et al. |
| 7,771,416 B2 | 8/2010 | Spivey et al. |
| 7,771,437 B2 | 8/2010 | Hogg et al. |

(56) References Cited

U.S. PATENT DOCUMENTS

| | | |
|---|---|---|
| 7,780,683 B2 | 8/2010 | Roue et al. |
| 7,780,691 B2 | 8/2010 | Stefanchik |
| 7,784,663 B2 | 8/2010 | Shelton, IV |
| 7,794,409 B2 | 9/2010 | Damarati |
| 7,794,475 B2 | 9/2010 | Hess et al. |
| 7,798,386 B2 | 9/2010 | Schall et al. |
| 7,815,565 B2 | 10/2010 | Stefanchik et al. |
| 7,815,659 B2 | 10/2010 | Conlon et al. |
| 7,815,662 B2 | 10/2010 | Spivey et al. |
| 7,828,186 B2 | 11/2010 | Wales |
| 7,833,156 B2 | 11/2010 | Williams et al. |
| 7,837,615 B2 | 11/2010 | Le et al. |
| 7,842,028 B2 | 11/2010 | Lee |
| 7,842,068 B2 | 11/2010 | Ginn |
| 7,846,171 B2 | 12/2010 | Kullas et al. |
| 7,850,660 B2 | 12/2010 | Uth et al. |
| 7,857,183 B2 | 12/2010 | Shelton, IV |
| 7,862,546 B2 | 1/2011 | Conlon et al. |
| 7,867,216 B2 | 1/2011 | Wahr et al. |
| 7,879,004 B2 | 2/2011 | Seibel et al. |
| 7,892,220 B2 | 2/2011 | Faller et al. |
| 7,896,804 B2 | 3/2011 | Uchimura et al. |
| 7,896,887 B2 | 3/2011 | Rimbaugh et al. |
| 7,905,828 B2 | 3/2011 | Brock et al. |
| 7,909,809 B2 | 3/2011 | Scopton et al. |
| 7,914,513 B2 | 3/2011 | Voorhees, Jr. |
| 7,918,869 B2 | 4/2011 | Saadat et al. |
| 7,927,271 B2 | 4/2011 | Dimitriou et al. |
| 7,931,624 B2 | 4/2011 | Smith et al. |
| 7,945,332 B2 | 5/2011 | Schechter |
| 7,947,000 B2 | 5/2011 | Vargas et al. |
| 7,953,326 B2 | 5/2011 | Farr et al. |
| 7,955,298 B2 | 6/2011 | Carroll et al. |
| 7,963,975 B2 | 6/2011 | Criscuolo |
| 7,965,180 B2 | 6/2011 | Koyama |
| 7,967,808 B2 | 6/2011 | Fitzgerald et al. |
| 7,969,473 B2 | 6/2011 | Kotoda |
| 7,972,330 B2 | 7/2011 | Alejandro et al. |
| 7,976,552 B2 | 7/2011 | Suzuki |
| 7,985,239 B2 | 7/2011 | Suzuki |
| 7,988,685 B2 | 8/2011 | Ziaie et al. |
| 8,029,504 B2 | 10/2011 | Long |
| 8,034,046 B2 | 10/2011 | Eidenschink |
| 8,037,591 B2 | 10/2011 | Spivey et al. |
| 8,048,067 B2 | 11/2011 | Davalos et al. |
| 8,057,510 B2 | 11/2011 | Ginn et al. |
| 8,062,311 B2 | 11/2011 | Litscher et al. |
| 8,066,632 B2 | 11/2011 | Dario et al. |
| 8,070,759 B2 | 12/2011 | Stefanchik et al. |
| 8,075,572 B2 | 12/2011 | Stefanchik et al. |
| 8,075,587 B2 | 12/2011 | Ginn |
| 8,088,062 B2 | 1/2012 | Zwolinski |
| 8,096,459 B2 | 1/2012 | Ortiz et al. |
| 8,100,922 B2 | 1/2012 | Griffith |
| 8,114,072 B2 | 2/2012 | Long et al. |
| 8,114,119 B2 | 2/2012 | Spivey et al. |
| 8,118,821 B2 | 2/2012 | Mouw |
| 8,147,424 B2 | 4/2012 | Kassab et al. |
| 8,157,813 B2 | 4/2012 | Ko et al. |
| 8,157,834 B2 | 4/2012 | Conlon |
| 8,172,772 B2 | 5/2012 | Zwolinski et al. |
| 8,182,414 B2 | 5/2012 | Handa et al. |
| 8,206,295 B2 | 6/2012 | Kaul |
| 8,221,310 B2 | 7/2012 | Saadat et al. |
| 8,303,581 B2 | 11/2012 | Arts et al. |
| 8,430,811 B2 | 4/2013 | Hess et al. |
| 2001/0023333 A1 | 9/2001 | Wise et al. |
| 2002/0022771 A1 | 2/2002 | Diokno et al. |
| 2002/0022857 A1 | 2/2002 | Goldsteen et al. |
| 2002/0023353 A1 | 2/2002 | Ting-Kung |
| 2002/0029055 A1 | 3/2002 | Bonutti |
| 2002/0042562 A1 | 4/2002 | Meron et al. |
| 2002/0049439 A1 | 4/2002 | Mulier et al. |
| 2002/0068945 A1 | 6/2002 | Sixto, Jr. et al. |
| 2002/0078967 A1 | 6/2002 | Sixto, Jr. et al. |
| 2002/0082516 A1 | 6/2002 | Stefanchik |
| 2002/0095164 A1 | 7/2002 | Andreas et al. |
| 2002/0107530 A1 | 8/2002 | Sauer et al. |
| 2002/0133115 A1 | 9/2002 | Gordon et al. |
| 2002/0138086 A1 | 9/2002 | Sixto, Jr. et al. |
| 2002/0147456 A1 | 10/2002 | Diduch et al. |
| 2002/0165592 A1 | 11/2002 | Glukhovsky et al. |
| 2002/0173805 A1 | 11/2002 | Matsuno et al. |
| 2002/0183591 A1 | 12/2002 | Matsuura et al. |
| 2003/0014090 A1 | 1/2003 | Abrahamson |
| 2003/0023255 A1 | 1/2003 | Miles et al. |
| 2003/0036679 A1 | 2/2003 | Kortenbach et al. |
| 2003/0069602 A1 | 4/2003 | Jacobs et al. |
| 2003/0078471 A1 | 4/2003 | Foley et al. |
| 2003/0083681 A1 | 5/2003 | Moutafis et al. |
| 2003/0114731 A1 | 6/2003 | Cadeddu et al. |
| 2003/0114732 A1 | 6/2003 | Webler et al. |
| 2003/0120257 A1 | 6/2003 | Houston et al. |
| 2003/0124009 A1 | 7/2003 | Ravi et al. |
| 2003/0130564 A1 | 7/2003 | Martone et al. |
| 2003/0130656 A1 | 7/2003 | Levin |
| 2003/0139646 A1 | 7/2003 | Sharrow et al. |
| 2003/0158521 A1 | 8/2003 | Ameri |
| 2003/0167062 A1 | 9/2003 | Gambale et al. |
| 2003/0171651 A1 | 9/2003 | Page et al. |
| 2003/0176880 A1 | 9/2003 | Long et al. |
| 2003/0216611 A1 | 11/2003 | Vu |
| 2003/0216615 A1 | 11/2003 | Ouchi |
| 2003/0220545 A1 | 11/2003 | Ouchi |
| 2003/0225312 A1 | 12/2003 | Suzuki et al. |
| 2003/0225332 A1 | 12/2003 | Okada et al. |
| 2003/0229269 A1 | 12/2003 | Humphrey |
| 2003/0229371 A1 | 12/2003 | Whitworth |
| 2003/0236549 A1 | 12/2003 | Bonadio et al. |
| 2004/0002683 A1 | 1/2004 | Nicholson et al. |
| 2004/0024414 A1 | 2/2004 | Downing |
| 2004/0034369 A1 | 2/2004 | Sauer et al. |
| 2004/0054322 A1 | 3/2004 | Vargas |
| 2004/0098007 A1 | 5/2004 | Heiss |
| 2004/0101456 A1 | 5/2004 | Kuroshima et al. |
| 2004/0104999 A1 | 6/2004 | Okada |
| 2004/0116948 A1 | 6/2004 | Sixto, Jr. et al. |
| 2004/0127940 A1 | 7/2004 | Ginn et al. |
| 2004/0133077 A1 | 7/2004 | Obenchain et al. |
| 2004/0133089 A1 | 7/2004 | Kilcoyne et al. |
| 2004/0136779 A1 | 7/2004 | Bhaskar |
| 2004/0138525 A1 | 7/2004 | Saadat et al. |
| 2004/0138529 A1 | 7/2004 | Wiltshire et al. |
| 2004/0138587 A1 | 7/2004 | Lyons, IV |
| 2004/0161451 A1 | 8/2004 | Pierce et al. |
| 2004/0167545 A1 | 8/2004 | Sadler et al. |
| 2004/0176699 A1 | 9/2004 | Walker et al. |
| 2004/0186350 A1 | 9/2004 | Brenneman et al. |
| 2004/0193009 A1 | 9/2004 | Jaffe et al. |
| 2004/0193146 A1 | 9/2004 | Lee et al. |
| 2004/0193186 A1 | 9/2004 | Kortenbach et al. |
| 2004/0193188 A1 | 9/2004 | Francese |
| 2004/0193189 A1 | 9/2004 | Kortenbach et al. |
| 2004/0193200 A1 | 9/2004 | Dworschak et al. |
| 2004/0199052 A1 | 10/2004 | Banik et al. |
| 2004/0199159 A1 | 10/2004 | Lee et al. |
| 2004/0206859 A1 | 10/2004 | Chong et al. |
| 2004/0210245 A1 | 10/2004 | Erickson et al. |
| 2004/0215058 A1 | 10/2004 | Zirps et al. |
| 2004/0225183 A1 | 11/2004 | Michlitsch et al. |
| 2004/0225186 A1 | 11/2004 | Horne, Jr. et al. |
| 2004/0225323 A1 | 11/2004 | Nagase et al. |
| 2004/0230095 A1 | 11/2004 | Stefanchik et al. |
| 2004/0230096 A1 | 11/2004 | Stefanchik et al. |
| 2004/0230161 A1 | 11/2004 | Zeiner |
| 2004/0243108 A1 | 12/2004 | Suzuki |
| 2004/0249246 A1 | 12/2004 | Campos |
| 2004/0249367 A1 | 12/2004 | Saadat et al. |
| 2004/0249394 A1 | 12/2004 | Morris et al. |
| 2004/0249443 A1 | 12/2004 | Shanley et al. |
| 2004/0254572 A1 | 12/2004 | McIntyre et al. |
| 2004/0260198 A1 | 12/2004 | Rothberg et al. |
| 2004/0260337 A1 | 12/2004 | Freed |
| 2005/0004515 A1 | 1/2005 | Hart et al. |

(56) References Cited

U.S. PATENT DOCUMENTS

| | | |
|---|---|---|
| 2005/0033265 A1 | 2/2005 | Engel et al. |
| 2005/0033277 A1 | 2/2005 | Clague et al. |
| 2005/0033319 A1 | 2/2005 | Gambale et al. |
| 2005/0033333 A1 | 2/2005 | Smith et al. |
| 2005/0043690 A1 | 2/2005 | Todd |
| 2005/0049616 A1 | 3/2005 | Rivera et al. |
| 2005/0059963 A1 | 3/2005 | Phan et al. |
| 2005/0059964 A1 | 3/2005 | Fitz |
| 2005/0065397 A1 | 3/2005 | Saadat et al. |
| 2005/0065509 A1 | 3/2005 | Coldwell et al. |
| 2005/0065517 A1 | 3/2005 | Chin |
| 2005/0070754 A1 | 3/2005 | Nobis et al. |
| 2005/0070763 A1 | 3/2005 | Nobis et al. |
| 2005/0070764 A1 | 3/2005 | Nobis et al. |
| 2005/0080413 A1 | 4/2005 | Canady |
| 2005/0085693 A1 | 4/2005 | Belson et al. |
| 2005/0085832 A1 | 4/2005 | Sancoff et al. |
| 2005/0090837 A1 | 4/2005 | Sixto, Jr. et al. |
| 2005/0090838 A1 | 4/2005 | Sixto, Jr. et al. |
| 2005/0096502 A1 | 5/2005 | Khalili |
| 2005/0101837 A1 | 5/2005 | Kalloo et al. |
| 2005/0101838 A1 | 5/2005 | Camillocci et al. |
| 2005/0101984 A1 | 5/2005 | Chanduszko et al. |
| 2005/0107663 A1 | 5/2005 | Saadat et al. |
| 2005/0107664 A1 | 5/2005 | Kalloo et al. |
| 2005/0110881 A1 | 5/2005 | Glukhovsky et al. |
| 2005/0113847 A1 | 5/2005 | Gadberry et al. |
| 2005/0119613 A1 | 6/2005 | Moenning et al. |
| 2005/0124855 A1 | 6/2005 | Jaffe et al. |
| 2005/0125010 A1 | 6/2005 | Smith et al. |
| 2005/0131279 A1 | 6/2005 | Boulais et al. |
| 2005/0131457 A1 | 6/2005 | Douglas et al. |
| 2005/0137454 A1 | 6/2005 | Saadat et al. |
| 2005/0143647 A1 | 6/2005 | Minai et al. |
| 2005/0143690 A1 | 6/2005 | High |
| 2005/0143774 A1 | 6/2005 | Polo |
| 2005/0143803 A1 | 6/2005 | Watson et al. |
| 2005/0149087 A1 | 7/2005 | Ahlberg et al. |
| 2005/0149096 A1 | 7/2005 | Hilal et al. |
| 2005/0159648 A1 | 7/2005 | Freed |
| 2005/0165272 A1 | 7/2005 | Okada et al. |
| 2005/0165378 A1 | 7/2005 | Heinrich et al. |
| 2005/0165411 A1 | 7/2005 | Orban, III |
| 2005/0165429 A1 | 7/2005 | Douglas et al. |
| 2005/0182429 A1 | 8/2005 | Yamanouchi |
| 2005/0192478 A1 | 9/2005 | Williams et al. |
| 2005/0192598 A1 | 9/2005 | Johnson et al. |
| 2005/0192602 A1 | 9/2005 | Manzo |
| 2005/0192654 A1 | 9/2005 | Chanduszko et al. |
| 2005/0209624 A1 | 9/2005 | Vijay |
| 2005/0215858 A1 | 9/2005 | Vail, III |
| 2005/0216050 A1 | 9/2005 | Sepetka et al. |
| 2005/0228224 A1 | 10/2005 | Okada et al. |
| 2005/0228406 A1 | 10/2005 | Bose |
| 2005/0234297 A1 | 10/2005 | Devierre et al. |
| 2005/0250983 A1 | 11/2005 | Tremaglio et al. |
| 2005/0250990 A1 | 11/2005 | Le et al. |
| 2005/0250993 A1 | 11/2005 | Jaeger |
| 2005/0251166 A1 | 11/2005 | Vaughan et al. |
| 2005/0251176 A1 | 11/2005 | Swanstrom et al. |
| 2005/0261674 A1 | 11/2005 | Nobis et al. |
| 2005/0267492 A1 | 12/2005 | Poncet et al. |
| 2005/0272975 A1 | 12/2005 | McWeeney et al. |
| 2005/0272977 A1 | 12/2005 | Saadat et al. |
| 2005/0273084 A1 | 12/2005 | Hinman et al. |
| 2005/0274935 A1 | 12/2005 | Nelson |
| 2005/0277945 A1 | 12/2005 | Saadat et al. |
| 2005/0277951 A1 | 12/2005 | Smith et al. |
| 2005/0277952 A1 | 12/2005 | Arp et al. |
| 2005/0277954 A1 | 12/2005 | Smith et al. |
| 2005/0277955 A1 | 12/2005 | Palmer et al. |
| 2005/0277956 A1 | 12/2005 | Francese et al. |
| 2005/0277957 A1 | 12/2005 | Kuhns et al. |
| 2005/0283118 A1 | 12/2005 | Uth et al. |
| 2005/0283119 A1 | 12/2005 | Uth et al. |
| 2005/0288555 A1 | 12/2005 | Binmoeller |
| 2006/0004406 A1 | 1/2006 | Wehrstein et al. |
| 2006/0004409 A1 | 1/2006 | Nobis et al. |
| 2006/0004410 A1 | 1/2006 | Nobis et al. |
| 2006/0015009 A1 | 1/2006 | Jaffe et al. |
| 2006/0015131 A1 | 1/2006 | Kierce et al. |
| 2006/0020167 A1 | 1/2006 | Sitzmann |
| 2006/0020247 A1 | 1/2006 | Kagan et al. |
| 2006/0025654 A1 | 2/2006 | Suzuki et al. |
| 2006/0025781 A1 | 2/2006 | Young et al. |
| 2006/0025812 A1 | 2/2006 | Shelton, IV |
| 2006/0025819 A1 | 2/2006 | Nobis et al. |
| 2006/0036267 A1 | 2/2006 | Saadat et al. |
| 2006/0041188 A1 | 2/2006 | Dirusso et al. |
| 2006/0058582 A1 | 3/2006 | Maahs et al. |
| 2006/0058776 A1 | 3/2006 | Bilsbury |
| 2006/0064083 A1 | 3/2006 | Khalaj et al. |
| 2006/0069396 A1 | 3/2006 | Meade et al. |
| 2006/0069424 A1 | 3/2006 | Acosta et al. |
| 2006/0069425 A1 | 3/2006 | Hillis et al. |
| 2006/0069429 A1 | 3/2006 | Spence et al. |
| 2006/0074413 A1 | 4/2006 | Behzadian |
| 2006/0079890 A1 | 4/2006 | Guerra |
| 2006/0089528 A1 | 4/2006 | Tartaglia et al. |
| 2006/0095031 A1 | 5/2006 | Ormsby |
| 2006/0095060 A1 | 5/2006 | Mayenberger et al. |
| 2006/0100687 A1 | 5/2006 | Fahey et al. |
| 2006/0106423 A1 | 5/2006 | Weisel et al. |
| 2006/0111209 A1 | 5/2006 | Hinman et al. |
| 2006/0111210 A1 | 5/2006 | Hinman et al. |
| 2006/0111704 A1 | 5/2006 | Brenneman et al. |
| 2006/0129166 A1 | 6/2006 | Lavelle |
| 2006/0135962 A1 | 6/2006 | Kick et al. |
| 2006/0135971 A1 | 6/2006 | Swanstrom et al. |
| 2006/0135984 A1 | 6/2006 | Kramer et al. |
| 2006/0142644 A1 | 6/2006 | Mulac et al. |
| 2006/0142652 A1 | 6/2006 | Keenan |
| 2006/0142790 A1 | 6/2006 | Gertner |
| 2006/0142798 A1 | 6/2006 | Holman et al. |
| 2006/0149131 A1 | 7/2006 | Or |
| 2006/0149132 A1 | 7/2006 | Iddan |
| 2006/0149135 A1 | 7/2006 | Paz |
| 2006/0161190 A1 | 7/2006 | Gadberry et al. |
| 2006/0167416 A1 | 7/2006 | Mathis et al. |
| 2006/0167482 A1 | 7/2006 | Swain et al. |
| 2006/0178560 A1 | 8/2006 | Saadat et al. |
| 2006/0183975 A1 | 8/2006 | Saadat et al. |
| 2006/0184161 A1 | 8/2006 | Maahs et al. |
| 2006/0189844 A1 | 8/2006 | Tien |
| 2006/0189845 A1 | 8/2006 | Maahs et al. |
| 2006/0190027 A1 | 8/2006 | Downey |
| 2006/0195084 A1 | 8/2006 | Slater |
| 2006/0200005 A1 | 9/2006 | Bjork et al. |
| 2006/0200121 A1 | 9/2006 | Mowery |
| 2006/0200169 A1 | 9/2006 | Sniffin |
| 2006/0200170 A1 | 9/2006 | Aranyi |
| 2006/0200199 A1 | 9/2006 | Bonutti et al. |
| 2006/0217665 A1 | 9/2006 | Prosek |
| 2006/0217697 A1 | 9/2006 | Lau et al. |
| 2006/0217742 A1 | 9/2006 | Messerly et al. |
| 2006/0217743 A1 | 9/2006 | Messerly et al. |
| 2006/0229639 A1 | 10/2006 | Whitfield |
| 2006/0229640 A1 | 10/2006 | Whitfield |
| 2006/0237022 A1 | 10/2006 | Chen et al. |
| 2006/0237023 A1 | 10/2006 | Cox et al. |
| 2006/0241570 A1 | 10/2006 | Wilk |
| 2006/0247500 A1 | 11/2006 | Voegele et al. |
| 2006/0247576 A1 | 11/2006 | Poncet |
| 2006/0247663 A1 | 11/2006 | Schwartz et al. |
| 2006/0247673 A1 | 11/2006 | Voegele et al. |
| 2006/0253004 A1 | 11/2006 | Frisch et al. |
| 2006/0253039 A1 | 11/2006 | McKenna et al. |
| 2006/0258907 A1 | 11/2006 | Stefanchik et al. |
| 2006/0258908 A1 | 11/2006 | Stefanchik et al. |
| 2006/0258910 A1 | 11/2006 | Stefanchik et al. |
| 2006/0258954 A1 | 11/2006 | Timberlake et al. |
| 2006/0258955 A1 | 11/2006 | Hoffman et al. |
| 2006/0259010 A1 | 11/2006 | Stefanchik et al. |
| 2006/0259073 A1 | 11/2006 | Miyamoto et al. |

(56) References Cited

U.S. PATENT DOCUMENTS

| | | |
|---|---|---|
| 2006/0264752 A1 | 11/2006 | Rubinsky et al. |
| 2006/0264904 A1 | 11/2006 | Kerby et al. |
| 2006/0264930 A1 | 11/2006 | Nishimura |
| 2006/0270902 A1 | 11/2006 | Igarashi et al. |
| 2006/0271042 A1 | 11/2006 | Latterell et al. |
| 2006/0271102 A1 | 11/2006 | Bosshard et al. |
| 2006/0276835 A1 | 12/2006 | Uchida |
| 2006/0281970 A1 | 12/2006 | Stokes et al. |
| 2006/0282106 A1 | 12/2006 | Cole et al. |
| 2006/0285732 A1 | 12/2006 | Horn et al. |
| 2006/0287644 A1 | 12/2006 | Inganas et al. |
| 2006/0287666 A1 | 12/2006 | Saadat et al. |
| 2006/0293626 A1 | 12/2006 | Byrum et al. |
| 2007/0002135 A1 | 1/2007 | Glukhovsky |
| 2007/0005019 A1 | 1/2007 | Okishige |
| 2007/0010801 A1 | 1/2007 | Chen et al. |
| 2007/0015965 A1 | 1/2007 | Cox et al. |
| 2007/0016225 A1 | 1/2007 | Nakao |
| 2007/0032700 A1 | 2/2007 | Fowler et al. |
| 2007/0032701 A1 | 2/2007 | Fowler et al. |
| 2007/0043261 A1 | 2/2007 | Watanabe et al. |
| 2007/0043345 A1 | 2/2007 | Davalos et al. |
| 2007/0049800 A1 | 3/2007 | Boulais |
| 2007/0049902 A1 | 3/2007 | Griffin et al. |
| 2007/0051375 A1 | 3/2007 | Milliman |
| 2007/0060880 A1 | 3/2007 | Gregorich et al. |
| 2007/0066869 A1 | 3/2007 | Hoffman |
| 2007/0066957 A1 * | 3/2007 | Demarais et al. ............ 604/500 |
| 2007/0067017 A1 | 3/2007 | Trapp |
| 2007/0073102 A1 | 3/2007 | Matsuno et al. |
| 2007/0073269 A1 | 3/2007 | Becker |
| 2007/0079924 A1 | 4/2007 | Saadat et al. |
| 2007/0083195 A1 | 4/2007 | Werneth et al. |
| 2007/0088370 A1 | 4/2007 | Kahle et al. |
| 2007/0100375 A1 | 5/2007 | Mikkaichi et al. |
| 2007/0100376 A1 | 5/2007 | Mikkaichi et al. |
| 2007/0106118 A1 | 5/2007 | Moriyama |
| 2007/0106317 A1 | 5/2007 | Shelton, IV et al. |
| 2007/0112251 A1 | 5/2007 | Nakhuda |
| 2007/0112331 A1 | 5/2007 | Weber et al. |
| 2007/0112342 A1 | 5/2007 | Pearson et al. |
| 2007/0112383 A1 | 5/2007 | Conlon et al. |
| 2007/0112385 A1 | 5/2007 | Conlon |
| 2007/0112417 A1 | 5/2007 | Shanley et al. |
| 2007/0112425 A1 | 5/2007 | Schaller et al. |
| 2007/0118115 A1 | 5/2007 | Artale et al. |
| 2007/0123840 A1 | 5/2007 | Cox |
| 2007/0129605 A1 | 6/2007 | Schaaf |
| 2007/0129719 A1 | 6/2007 | Kendale et al. |
| 2007/0129760 A1 | 6/2007 | Demarais et al. |
| 2007/0135709 A1 | 6/2007 | Rioux et al. |
| 2007/0135803 A1 | 6/2007 | Belson |
| 2007/0142706 A1 | 6/2007 | Matsui et al. |
| 2007/0142710 A1 | 6/2007 | Yokoi et al. |
| 2007/0142780 A1 | 6/2007 | Van Lue |
| 2007/0154460 A1 | 7/2007 | Kraft et al. |
| 2007/0156028 A1 | 7/2007 | Van Lue et al. |
| 2007/0156127 A1 | 7/2007 | Rioux et al. |
| 2007/0161855 A1 | 7/2007 | Mikkaichi et al. |
| 2007/0162101 A1 | 7/2007 | Burgermeister et al. |
| 2007/0167901 A1 | 7/2007 | Herrig et al. |
| 2007/0173691 A1 | 7/2007 | Yokoi et al. |
| 2007/0173869 A1 | 7/2007 | Gannoe et al. |
| 2007/0173870 A2 | 7/2007 | Zacharias |
| 2007/0173872 A1 | 7/2007 | Neuenfeldt |
| 2007/0179525 A1 | 8/2007 | Frecker et al. |
| 2007/0179530 A1 | 8/2007 | Tieu et al. |
| 2007/0197865 A1 | 8/2007 | Miyake et al. |
| 2007/0198057 A1 | 8/2007 | Gelbart et al. |
| 2007/0203398 A1 | 8/2007 | Bonadio et al. |
| 2007/0203487 A1 | 8/2007 | Sugita |
| 2007/0208336 A1 | 9/2007 | Kim et al. |
| 2007/0208364 A1 | 9/2007 | Smith et al. |
| 2007/0213754 A1 | 9/2007 | Mikkaichi et al. |
| 2007/0225554 A1 | 9/2007 | Maseda et al. |
| 2007/0233040 A1 | 10/2007 | Macnamara et al. |
| 2007/0244358 A1 | 10/2007 | Lee |
| 2007/0250038 A1 | 10/2007 | Boulais |
| 2007/0250057 A1 | 10/2007 | Nobis et al. |
| 2007/0255096 A1 | 11/2007 | Stefanchik et al. |
| 2007/0255100 A1 | 11/2007 | Barlow et al. |
| 2007/0255273 A1 | 11/2007 | Fernandez et al. |
| 2007/0255303 A1 | 11/2007 | Bakos et al. |
| 2007/0255306 A1 | 11/2007 | Conlon et al. |
| 2007/0260112 A1 | 11/2007 | Rahmani |
| 2007/0260117 A1 | 11/2007 | Zwolinski et al. |
| 2007/0260121 A1 | 11/2007 | Bakos et al. |
| 2007/0260242 A1 | 11/2007 | Dycus et al. |
| 2007/0260273 A1 | 11/2007 | Cropper et al. |
| 2007/0260302 A1 | 11/2007 | Igaki |
| 2007/0270629 A1 | 11/2007 | Charles |
| 2007/0270889 A1 | 11/2007 | Conlon et al. |
| 2007/0270895 A1 | 11/2007 | Nobis et al. |
| 2007/0270907 A1 | 11/2007 | Stokes et al. |
| 2007/0282165 A1 | 12/2007 | Hopkins et al. |
| 2007/0282371 A1 | 12/2007 | Lee et al. |
| 2007/0293727 A1 | 12/2007 | Goldfarb et al. |
| 2007/0299387 A1 | 12/2007 | Williams et al. |
| 2008/0004650 A1 | 1/2008 | George |
| 2008/0015409 A1 | 1/2008 | Barlow et al. |
| 2008/0015413 A1 | 1/2008 | Barlow et al. |
| 2008/0015552 A1 | 1/2008 | Doyle et al. |
| 2008/0021416 A1 | 1/2008 | Arai et al. |
| 2008/0022927 A1 | 1/2008 | Zhang et al. |
| 2008/0027387 A1 | 1/2008 | Grabinsky |
| 2008/0033451 A1 | 2/2008 | Rieber et al. |
| 2008/0051629 A1 | 2/2008 | Sugiyama et al. |
| 2008/0051735 A1 | 2/2008 | Measamer et al. |
| 2008/0058586 A1 | 3/2008 | Karpiel |
| 2008/0058854 A1 | 3/2008 | Kieturakis et al. |
| 2008/0065169 A1 | 3/2008 | Colliou et al. |
| 2008/0071264 A1 | 3/2008 | Azure |
| 2008/0086172 A1 | 4/2008 | Martin et al. |
| 2008/0097159 A1 | 4/2008 | Ishiguro |
| 2008/0097472 A1 | 4/2008 | Agmon et al. |
| 2008/0097483 A1 | 4/2008 | Ortiz et al. |
| 2008/0103527 A1 | 5/2008 | Martin et al. |
| 2008/0114384 A1 | 5/2008 | Chang et al. |
| 2008/0119870 A1 | 5/2008 | Williams |
| 2008/0119891 A1 | 5/2008 | Miles et al. |
| 2008/0125796 A1 | 5/2008 | Graham |
| 2008/0132892 A1 | 6/2008 | Lunsford et al. |
| 2008/0139882 A1 | 6/2008 | Fujimori |
| 2008/0140069 A1 | 6/2008 | Filloux et al. |
| 2008/0140071 A1 | 6/2008 | Vegesna |
| 2008/0147113 A1 | 6/2008 | Nobis et al. |
| 2008/0171907 A1 | 7/2008 | Long et al. |
| 2008/0177135 A1 | 7/2008 | Muyari et al. |
| 2008/0188710 A1 | 8/2008 | Segawa et al. |
| 2008/0188868 A1 | 8/2008 | Weitzner et al. |
| 2008/0200755 A1 | 8/2008 | Bakos |
| 2008/0200762 A1 | 8/2008 | Stokes et al. |
| 2008/0200911 A1 | 8/2008 | Long |
| 2008/0200933 A1 | 8/2008 | Bakos et al. |
| 2008/0200934 A1 | 8/2008 | Fox |
| 2008/0208213 A1 | 8/2008 | Benjamin et al. |
| 2008/0221587 A1 | 9/2008 | Schwartz |
| 2008/0228213 A1 | 9/2008 | Blakeney et al. |
| 2008/0230972 A1 | 9/2008 | Ganley |
| 2008/0234696 A1 | 9/2008 | Taylor et al. |
| 2008/0243106 A1 | 10/2008 | Coe et al. |
| 2008/0243148 A1 | 10/2008 | Mikkaichi et al. |
| 2008/0243176 A1 | 10/2008 | Weitzner et al. |
| 2008/0249567 A1 | 10/2008 | Kaplan |
| 2008/0262513 A1 | 10/2008 | Stahler et al. |
| 2008/0262524 A1 | 10/2008 | Bangera et al. |
| 2008/0262540 A1 | 10/2008 | Bangera et al. |
| 2008/0275474 A1 | 11/2008 | Martin et al. |
| 2008/0275475 A1 | 11/2008 | Schwemberger et al. |
| 2008/0287737 A1 | 11/2008 | Dejima |
| 2008/0287983 A1 | 11/2008 | Smith et al. |
| 2008/0300461 A1 | 12/2008 | Shaw et al. |
| 2008/0300547 A1 | 12/2008 | Bakos |
| 2008/0300571 A1 | 12/2008 | LePivert |

(56) References Cited

U.S. PATENT DOCUMENTS

| | | |
|---|---|---|
| 2008/0309758 A1 | 12/2008 | Karasawa et al. |
| 2008/0312496 A1 | 12/2008 | Zwolinski |
| 2008/0312499 A1 | 12/2008 | Handa et al. |
| 2008/0312500 A1 | 12/2008 | Asada et al. |
| 2008/0312506 A1 | 12/2008 | Spivey et al. |
| 2008/0319436 A1 | 12/2008 | Daniel et al. |
| 2008/0319439 A1 | 12/2008 | Ootsubu |
| 2009/0005636 A1 | 1/2009 | Pang et al. |
| 2009/0054728 A1 | 2/2009 | Trusty |
| 2009/0062788 A1 | 3/2009 | Long et al. |
| 2009/0062792 A1 | 3/2009 | Vakharia et al. |
| 2009/0062795 A1 | 3/2009 | Vakharia et al. |
| 2009/0069634 A1 | 3/2009 | Larkin |
| 2009/0076499 A1 | 3/2009 | Azure |
| 2009/0078736 A1 | 3/2009 | Van Lue |
| 2009/0082776 A1 | 3/2009 | Cresina |
| 2009/0082779 A1 | 3/2009 | Nakao |
| 2009/0112059 A1 | 4/2009 | Nobis |
| 2009/0112062 A1 | 4/2009 | Bakos |
| 2009/0112063 A1 | 4/2009 | Bakos et al. |
| 2009/0125042 A1 | 5/2009 | Mouw |
| 2009/0131751 A1 | 5/2009 | Spivey et al. |
| 2009/0131932 A1 | 5/2009 | Vakharia et al. |
| 2009/0131933 A1 | 5/2009 | Ghabrial et al. |
| 2009/0143639 A1 | 6/2009 | Stark |
| 2009/0143649 A1 | 6/2009 | Rossi |
| 2009/0143794 A1 | 6/2009 | Conlon et al. |
| 2009/0143818 A1 | 6/2009 | Faller et al. |
| 2009/0149710 A1 | 6/2009 | Stefanchik et al. |
| 2009/0177031 A1 | 7/2009 | Surti et al. |
| 2009/0177219 A1 | 7/2009 | Conlon |
| 2009/0182332 A1 | 7/2009 | Long et al. |
| 2009/0192344 A1 | 7/2009 | Bakos et al. |
| 2009/0192534 A1 | 7/2009 | Ortiz et al. |
| 2009/0198231 A1 | 8/2009 | Esser et al. |
| 2009/0198253 A1 | 8/2009 | Omori |
| 2009/0210000 A1 | 8/2009 | Sullivan et al. |
| 2009/0216248 A1 | 8/2009 | Uenohara et al. |
| 2009/0221873 A1 | 9/2009 | McGrath |
| 2009/0227828 A1 | 9/2009 | Swain et al. |
| 2009/0228001 A1 | 9/2009 | Pacey |
| 2009/0248055 A1 | 10/2009 | Spivey et al. |
| 2009/0259105 A1 | 10/2009 | Miyano et al. |
| 2009/0269317 A1 | 10/2009 | Davalos |
| 2009/0281559 A1 | 11/2009 | Swain et al. |
| 2009/0287206 A1 | 11/2009 | Jun |
| 2009/0287236 A1 | 11/2009 | Bakos et al. |
| 2009/0292164 A1 | 11/2009 | Yamatani |
| 2009/0299135 A1 | 12/2009 | Spivey |
| 2009/0299143 A1 | 12/2009 | Conlon et al. |
| 2009/0299406 A1 | 12/2009 | Swain et al. |
| 2009/0299409 A1 | 12/2009 | Coe et al. |
| 2009/0306658 A1 | 12/2009 | Nobis et al. |
| 2009/0306683 A1 | 12/2009 | Zwolinski et al. |
| 2009/0322864 A1 | 12/2009 | Karasawa et al. |
| 2009/0326332 A1 | 12/2009 | Carter |
| 2009/0326561 A1 | 12/2009 | Carroll, II et al. |
| 2010/0010294 A1 | 1/2010 | Conlon et al. |
| 2010/0010298 A1 | 1/2010 | Bakos et al. |
| 2010/0010299 A1 | 1/2010 | Bakos et al. |
| 2010/0010303 A1 | 1/2010 | Bakos |
| 2010/0010510 A1 | 1/2010 | Stefanchik |
| 2010/0010511 A1 | 1/2010 | Harris et al. |
| 2010/0023032 A1 | 1/2010 | Granja Filho |
| 2010/0030211 A1 | 2/2010 | Davalos et al. |
| 2010/0036198 A1 | 2/2010 | Tacchino et al. |
| 2010/0042045 A1 | 2/2010 | Spivey |
| 2010/0048990 A1 | 2/2010 | Bakos |
| 2010/0049190 A1 | 2/2010 | Long et al. |
| 2010/0049223 A1 | 2/2010 | Granja Filho |
| 2010/0056861 A1 | 3/2010 | Spivey et al. |
| 2010/0056862 A1 | 3/2010 | Bakos |
| 2010/0056864 A1 | 3/2010 | Lee |
| 2010/0057085 A1 | 3/2010 | Holcomb et al. |
| 2010/0057108 A1 | 3/2010 | Spivey et al. |
| 2010/0076451 A1 | 3/2010 | Zwolinski et al. |
| 2010/0076460 A1 | 3/2010 | Taylor et al. |
| 2010/0081877 A1 | 4/2010 | Vakharia |
| 2010/0091128 A1 | 4/2010 | Ogasawara et al. |
| 2010/0113872 A1 | 5/2010 | Asada et al. |
| 2010/0121362 A1 | 5/2010 | Clague et al. |
| 2010/0130817 A1 | 5/2010 | Conlon |
| 2010/0130975 A1 | 5/2010 | Long |
| 2010/0152539 A1 | 6/2010 | Ghabrial et al. |
| 2010/0152746 A1 | 6/2010 | Ceniccola et al. |
| 2010/0179510 A1 | 7/2010 | Fox et al. |
| 2010/0179530 A1 | 7/2010 | Long et al. |
| 2010/0191050 A1 | 7/2010 | Zwolinski |
| 2010/0191267 A1 | 7/2010 | Fox |
| 2010/0198005 A1 | 8/2010 | Fox |
| 2010/0198149 A1 | 8/2010 | Fox |
| 2010/0198248 A1 | 8/2010 | Vakharia |
| 2010/0217367 A1 | 8/2010 | Belson |
| 2010/0249700 A1 | 9/2010 | Spivey |
| 2010/0256628 A1 | 10/2010 | Pearson et al. |
| 2010/0261994 A1 | 10/2010 | Davalos et al. |
| 2010/0286791 A1 | 11/2010 | Goldsmith |
| 2010/0298642 A1 | 11/2010 | Trusty et al. |
| 2010/0312056 A1 | 12/2010 | Galperin et al. |
| 2010/0331622 A2 | 12/2010 | Conlon |
| 2010/0331758 A1 | 12/2010 | Davalos et al. |
| 2010/0331774 A2 | 12/2010 | Spivey |
| 2011/0077476 A1 | 3/2011 | Rofougaran |
| 2011/0093009 A1 | 4/2011 | Fox |
| 2011/0098694 A1 | 4/2011 | Long |
| 2011/0098704 A1 | 4/2011 | Long et al. |
| 2011/0105850 A1 | 5/2011 | Voegele et al. |
| 2011/0106221 A1 | 5/2011 | Neal, II et al. |
| 2011/0112434 A1 | 5/2011 | Ghabrial et al. |
| 2011/0112527 A1* | 5/2011 | Hamilton et al. ............... 606/41 |
| 2011/0115891 A1 | 5/2011 | Trusty |
| 2011/0124964 A1 | 5/2011 | Nobis |
| 2011/0152609 A1 | 6/2011 | Trusty et al. |
| 2011/0152610 A1 | 6/2011 | Trusty et al. |
| 2011/0152612 A1 | 6/2011 | Trusty et al. |
| 2011/0152858 A1 | 6/2011 | Long et al. |
| 2011/0152859 A1 | 6/2011 | Long et al. |
| 2011/0152878 A1 | 6/2011 | Trusty et al. |
| 2011/0152923 A1 | 6/2011 | Fox |
| 2011/0160514 A1* | 6/2011 | Long et al. .................. 600/2 |
| 2011/0190659 A1 | 8/2011 | Long et al. |
| 2011/0190764 A1 | 8/2011 | Long et al. |
| 2011/0193948 A1 | 8/2011 | Amling et al. |
| 2011/0224665 A1* | 9/2011 | Crosby et al. ............... 606/33 |
| 2011/0245619 A1 | 10/2011 | Holcomb |
| 2011/0285488 A1 | 11/2011 | Scott et al. |
| 2011/0306971 A1 | 12/2011 | Long |
| 2012/0004502 A1 | 1/2012 | Weitzner et al. |
| 2012/0029335 A1 | 2/2012 | Sudam et al. |
| 2012/0088965 A1 | 4/2012 | Stokes et al. |
| 2012/0089089 A1 | 4/2012 | Swain et al. |
| 2012/0089093 A1 | 4/2012 | Trusty |
| 2012/0116155 A1 | 5/2012 | Trusty |
| 2012/0150172 A1* | 6/2012 | Ortiz et al. .................. 606/41 |
| 2012/0179148 A1 | 7/2012 | Conlon |
| 2012/0191075 A1 | 7/2012 | Trusty |
| 2012/0191076 A1 | 7/2012 | Voegele et al. |
| 2012/0220998 A1 | 8/2012 | Long et al. |
| 2012/0221002 A1 | 8/2012 | Long et al. |
| 2012/0238796 A1 | 9/2012 | Conlon |
| 2012/0330306 A1 | 12/2012 | Long et al. |
| 2013/0090666 A1 | 4/2013 | Hess et al. |
| 2013/0158348 A1 | 6/2013 | Nobis et al. |
| 2013/0274735 A1* | 10/2013 | Hastings et al. ............... 606/34 |

FOREIGN PATENT DOCUMENTS

| | | |
|---|---|---|
| DE | 4323585 A1 | 1/1995 |
| DE | 19713797 A1 | 10/1997 |
| DE | 19757056 B4 | 8/2008 |
| DE | 102006027873 B4 | 10/2009 |
| EP | 0086338 A1 | 8/1983 |
| EP | 0286415 A2 | 10/1988 |
| EP | 0589454 A2 | 3/1994 |

(56) References Cited

FOREIGN PATENT DOCUMENTS

| | | |
|---|---|---|
| EP | 0464479 81 | 3/1995 |
| EP | 0529675 B1 | 2/1996 |
| EP | 0621009 B1 | 7/1997 |
| EP | 0724863 B1 | 7/1999 |
| EP | 0760629 B1 | 11/1999 |
| EP | 0818974 B1 | 7/2001 |
| EP | 1281356 A2 | 2/2003 |
| EP | 0947166 B1 | 5/2003 |
| EP | 0836832 B1 | 12/2003 |
| EP | 1402837 A1 | 3/2004 |
| EP | 0744918 B1 | 4/2004 |
| EP | 0931515 B1 | 8/2004 |
| EP | 0941128 81 | 10/2004 |
| EP | 1411843 B1 | 10/2004 |
| EP | 1150614 B1 | 11/2004 |
| EP | 1477104 A1 | 11/2004 |
| EP | 1481642 A1 | 12/2004 |
| EP | 1493391 A1 | 1/2005 |
| EP | 0848598 B1 | 2/2005 |
| EP | 1281360 B1 | 3/2005 |
| EP | 1568330 A1 | 8/2005 |
| EP | 1452143 B1 | 9/2005 |
| EP | 1616527 A2 | 1/2006 |
| EP | 1006888 81 | 3/2006 |
| EP | 1629764 A1 | 3/2006 |
| EP | 1013229 B1 | 6/2006 |
| EP | 1721561 A1 | 11/2006 |
| EP | 1153578 B1 | 3/2007 |
| EP | 1334696 B1 | 3/2007 |
| EP | 1769766 A1 | 4/2007 |
| EP | 1836971 A2 | 9/2007 |
| EP | 1836980 A1 | 9/2007 |
| EP | 1854421 A2 | 11/2007 |
| EP | 1857061 A1 | 11/2007 |
| EP | 1875876 A1 | 1/2008 |
| EP | 1891881 A1 | 2/2008 |
| EP | 1902663 A1 | 3/2008 |
| EP | 1477106 B1 | 6/2008 |
| EP | 1949844 A1 | 7/2008 |
| EP | 1518499 B1 | 8/2008 |
| EP | 1582138 B1 | 9/2008 |
| EP | 1709918 B1 | 10/2008 |
| EP | 1985226 A2 | 10/2008 |
| EP | 1994904 A1 | 11/2008 |
| EP | 1707130 B1 | 12/2008 |
| EP | 0723462 B1 | 3/2009 |
| EP | 1769749 B1 | 11/2009 |
| EP | 2135545 A2 | 12/2009 |
| EP | 1493397 B1 | 9/2011 |
| FR | 2731610 A1 | 9/1996 |
| GB | 330629 A | 6/1930 |
| GB | 2335860 A | 10/1999 |
| GB | 2403909 A | 1/2005 |
| GB | 2421190 A | 6/2006 |
| GB | 2443261 A | 4/2008 |
| JP | 56-46674 | 4/1981 |
| JP | 63309252 A | 12/1988 |
| JP | 4038960 A | 2/1992 |
| JP | 8-29699 A | 2/1996 |
| JP | 2000245683 A | 9/2000 |
| JP | 2002-369791 A | 12/2002 |
| JP | 2003-088494 A | 3/2003 |
| JP | 2003-235852 A | 3/2003 |
| JP | 2004-33525 A | 2/2004 |
| JP | 2004-065745 A | 3/2004 |
| JP | 2005-121947 A | 5/2005 |
| JP | 2005-261514 A | 9/2005 |
| JP | 2006297005 A | 11/2006 |
| JP | 2006-343510 A | 12/2006 |
| NL | 1021295 C2 | 2/2004 |
| SU | 194230 | 5/1967 |
| SU | 980703 | 12/1982 |
| WO | WO 84/01707 A1 | 5/1984 |
| WO | WO 92/13494 A1 | 8/1992 |
| WO | WO 93/10850 A1 | 6/1993 |
| WO | WO 93/20760 A1 | 10/1993 |
| WO | WO 93/20765 A1 | 10/1993 |
| WO | WO 95/09666 A1 | 4/1995 |
| WO | WO 96/22056 A1 | 7/1996 |
| WO | WO 96/27331 A1 | 9/1996 |
| WO | WO 96/39946 A1 | 12/1996 |
| WO | WO 97/12557 A1 | 4/1997 |
| WO | WO 98/01080 A1 | 1/1998 |
| WO | WO 99/00060 A1 | 1/1999 |
| WO | WO 99/09919 A1 | 3/1999 |
| WO | WO 99/17661 A1 | 4/1999 |
| WO | WO 99/30622 A2 | 6/1999 |
| WO | WO 00/35358 A1 | 6/2000 |
| WO | WO 00/68665 A1 | 11/2000 |
| WO | WO 01/10319 A1 | 2/2001 |
| WO | WO 01/26708 A1 | 4/2001 |
| WO | WO 01/41627 A2 | 6/2001 |
| WO | WO 01/58360 A2 | 8/2001 |
| WO | WO 02/11621 A2 | 2/2002 |
| WO | WO 02/34122 A2 | 5/2002 |
| WO | WO 02/094082 A2 | 11/2002 |
| WO | WO 03/045260 A1 | 6/2003 |
| WO | WO 03/047684 A2 | 6/2003 |
| WO | WO 03/059412 A2 | 7/2003 |
| WO | WO 03/078721 A2 | 9/2003 |
| WO | WO 03/081761 A2 | 10/2003 |
| WO | WO 03/082129 A2 | 10/2003 |
| WO | WO 2004/006789 A1 | 1/2004 |
| WO | WO 2004/028613 A2 | 4/2004 |
| WO | WO 2004/037123 A1 | 5/2004 |
| WO | WO 2004/037149 A1 | 5/2004 |
| WO | WO 2004/052221 A1 | 6/2004 |
| WO | WO 2004/086984 A1 | 10/2004 |
| WO | WO 2005/009211 A2 | 2/2005 |
| WO | WO 2005/018467 A2 | 3/2005 |
| WO | WO 2005/037088 A2 | 4/2005 |
| WO | WO 2005/048827 A1 | 6/2005 |
| WO | WO 2005/065284 A2 | 7/2005 |
| WO | WO 2005/097019 A2 | 10/2005 |
| WO | WO 2005/097234 A2 | 10/2005 |
| WO | WO 2005/112810 A2 | 12/2005 |
| WO | WO 2005/120363 A1 | 12/2005 |
| WO | WO 2005/122866 A1 | 12/2005 |
| WO | WO 2006/007399 A1 | 1/2006 |
| WO | WO 2006/012630 A2 | 2/2006 |
| WO | WO 2006/040109 A1 | 4/2006 |
| WO | WO 2006/041881 A2 | 4/2006 |
| WO | WO 2006/060405 A2 | 6/2006 |
| WO | WO 2006/110733 A2 | 10/2006 |
| WO | WO 2006/113216 A2 | 10/2006 |
| WO | WO 2007/013059 A2 | 2/2007 |
| WO | WO 2007/014063 A2 | 2/2007 |
| WO | WO 2007/035537 A2 | 3/2007 |
| WO | WO 2007/048085 A2 | 4/2007 |
| WO | WO 2007/063550 A2 | 6/2007 |
| WO | WO 2007/100067 A1 | 9/2007 |
| WO | WO 2007/109171 A2 | 9/2007 |
| WO | WO 2007/135577 A2 | 11/2007 |
| WO | WO 2007/143200 A2 | 12/2007 |
| WO | WO 2007/144004 A1 | 12/2007 |
| WO | WO 2008/005433 A1 | 1/2008 |
| WO | WO 2008/033356 A2 | 3/2008 |
| WO | WO 2008/041225 A2 | 4/2008 |
| WO | WO 2008/076337 A1 | 6/2008 |
| WO | WO 2008/076800 A2 | 6/2008 |
| WO | WO 2008/079440 A2 | 7/2008 |
| WO | WO 2008/101075 A2 | 8/2008 |
| WO | WO 2008/101086 A2 | 8/2008 |
| WO | WO 2008/102154 A2 | 8/2008 |
| WO | WO 2008/108863 A2 | 9/2008 |
| WO | WO 2008/151237 A1 | 12/2008 |
| WO | WO 2009/021030 A1 | 2/2009 |
| WO | WO 2009/027065 A1 | 3/2009 |
| WO | WO 2009/029065 A1 | 3/2009 |
| WO | WO 2009/032623 A2 | 3/2009 |
| WO | WO 2009/036457 A1 | 3/2009 |
| WO | WO 2009/121017 A1 | 10/2009 |
| WO | WO 2010/027688 A1 | 3/2010 |

(56) References Cited

FOREIGN PATENT DOCUMENTS

| WO | WO 2010/056716 A2 | 5/2010 |
| WO | WO 2010/080974 A1 | 7/2010 |
| WO | WO 2010/088481 A1 | 8/2010 |

OTHER PUBLICATIONS

Michael S. Kavic, M.D., "Natural Orifice Translumenal Endoscopic Surgery: "NOTES"", JSLS, vol. 10, pp. 133-134 (2006).
Ethicon, Inc., "Wound Closure Manual: Chapter 3 (The Surgical Needle)," 15 pages, (1994).
Guido M. Sclabas, M.D., et al., "Endoluminal Methods for Gastrotomy Closure in Natural Orifice TransEnteric Surgery (NOTES)," Surgical Innovation, vol. 13, No. 1, pp. 23-30, Mar. 2006.
Fritscher-Ravens, et al., "Transgastric Gastropexy and Hiatal Hernia Repair for GERD Under EUS Control: a Porcine Model," Gastrointestinal Endoscopy, vol. 59, No. 1, pp. 89-95, 2004.
Ogando, "Prototype Tools That Go With the Flow," Design News, 2 pages, Jul. 17, 2006.
Edd, et al., "In Vivo Results of a New Focal Tissue Ablation Technique: Irreversible Electroporation," IEEE Trans Biomed Eng, vol. 53, pp. 1409-1415, 2006.
Kennedy, et al., "High-Burst-Strength, Feedback-Controlled Bipolar Vessel Sealing," Surgical Endoscopy, vol. 12, pp. 876-878 (1998).
Collins et al., "Local Gene Therapy of Solid Tumors with GM-CSF and B7-1 Eradicates Both Treated and Distal Tumors," Cancer Gene Therapy, vol. 13, pp. 1061-1071 (2006).
K. Sumiyama et al., "Transesophageal Mediastinoscopy by Submucosal Endoscopy With Mucosal Flap Safety Value Technique," Gastrointest Endosc., Apr. 2007, vol. 65(4), pp. 679-683 (Abstract).
K. Sumiyama et al., "Submucosal Endoscopy with Mucosal Flap Safety Valve," Gastrointest Endosc. Apr. 2007, vol. 65(4) pp. 694-695 (Abstract).
K. Sumiyama et al., "Transgastric Cholecystectomy: Transgastric Accessibility to the Gallbladder Improved with the SEMF Method and a Novel Multibending Therapeutic Endoscope," Gastrointest Endosc., Jun. 2007, vol. 65(7), pp. 1028-1034 (Abstract).
K. Sumiyama et al., "Endoscopic Caps," Tech. Gastrointest. Endosc., vol. 8, pp. 28-32, 2006.
"Z-Offset Technique Used in the Introduction of Trocar During Laparoscopic Surgery," M.S. Hershey NOTES Presentation to EES NOTES Development Team, Sep. 27, 2007.
F.N. Denans, Nouveau Procede Pour La Guerison Des Plaies Des Intestines. Extrait Des Seances De La Societe Royale De Medecine De Marseille, Pendant Le Mois De Decembre 1825, et le Premier Tremestre De 1826, Séance Du 24 Fevrier 1826. Recueil De La Societe Royale De Medecin De Marseille. Marseille: Impr. D'Achard, 1826; 1:127-31. (with English translation).
I. Fraser, "An Historical Perspective on Mechanical Aids in Intestinal Anastamosis," Surg. Gynecol. Obstet. (Oct. 1982), vol. 155, pp. 566-574.
M.E. Ryan et al., "Endoscopic Intervention for Biliary Leaks After Laparoscopic Cholecystectomy: A Multicenter Review," Gastrointest. Endosc., vol. 47(3), 1998, pp. 261-266.
C. Cope, "Creation of Compression Gastroenterostomy by Means of the Oral, Percutaneous, or Surgical Introduction of Magnets: Feasibility Study in Swine," J. Vasc Intery Radiol, (1995), vol. 6(4), pp. 539-545.
J.W. Hazey et al., "Natural Orifice Transgastric Endoscopic Peritoneoscopy in Humans: Initial Clinical Trial," Surg Endosc, (Jan. 2008), vol. 22(1), pp. 16-20.
N. Chopita et al., "Endoscopic Gastroenteric Anastamosis Using Magnets," Endoscopy, (2005), vol. 37(4), pp. 313-317.
C. Cope et al., "Long Term Patency of Experimental Magnetic Compression Gastroenteric Anastomoses Achieved with Covered Stents," Gastrointest Endosc, (2001), vol. 53, pp. 780-784.
H. Okajima et al., "Magnet Compression Anastamosis for Bile Duct Stenosis After Duct to Duct Biliary Reconstruction in Living Donor Liver Transplantation," Liver Transplantation (2005), pp. 473-475.
A. Fritscher-Ravens et al., "Transluminal Endosurgery: Single Lumen Access Anastamotic Device for Flexible Endoscopy," Gastrointestinal Endosc, (2003), vol. 58(4), pp. 585-591.
G.A. Hallenbeck, M.D. et al., "An Instrument for Colorectal Anastomosis Without Sutrues," Dis Col Rectum, (1963), vol. 5, pp. 98-101.
T. Hardy, Jr., M.D. et al., "A Biofragmentable Ring for Sutureless Bowel Anastomosis. An Experimental Study," Dis Col Rectum, (1985), vol. 28, pp. 484-490.
P. O'Neill, M.D. et al., "Nonsuture Intestinal Anastomosis," Am J. Surg, (1962), vol. 104, pp. 761-767.
C.P. Swain, M.D. et al., "Anastomosis at Flexible Endoscopy: An Experimental Study of Compression Button Gastrojejunostomy," Gastrointest Endosc, (1991), vol. 37, pp. 628-632.
J.B. Murphy, M.D., "Cholecysto-Intestinal, Gastro-Intestinal, Entero-Intestinal Anastomosis, and Approximation Without Sutures (original research)," Med Rec, (Dec. 10, 1892), vol. 42(24), pp. 665-676.
USGI® EndoSurgical Operating System—g-Prox® Tissue Grasper/Approximation Device; [online] URL: http://www.usgimedical.com/eos/components-gprox.htm—accessed May 30, 2008 (2 pages).
Printout of web page—http://www.vacumed.com/zcom/product/Product.do?compid=27&prodid=852, #51XX Low-Cost Permanent Tubes 2MM ID, Smooth Interior Walls, VacuMed, Ventura, California, Accessed Jul. 24, 2007.
Endoscopic Retrograde Cholangiopancreatogram (ERCP); [online] URL: http://www.webmd.com/digestive-disorders/endoscopic-retrograde-cholangiopancreatogram-ercp.htm; last updated: Apr. 30, 2007; accessed: Feb. 21, 2008 (6 pages).
ERCP; Jackson Siegelbaum Gastroenterology; [online] URL: http://www.gicare.com/pated/epdgs20.htm; accessed Feb. 21, 2008 (3 pages).
D.G. Fong et al., "Transcolonic Ventral Wall Hernia Mesh Fixation in a Porcine Model," Endoscopy 2007; 39: 865-869.
B. Rubinsky, Ph.D., "Irreversible Electroporation in Medicine," Technology in Cancer Research and Treatment, vol. 6, No. 4, Aug. (2007), pp. 255-259.
D.B. Nelson, MD et al., "Endoscopic Hemostatic Devices," Gastrointestinal Endoscopy, vol. 54, No. 6, 2001, pp. 833-840.
CRE™ Pulmonary Balloon Dilator; [online] URL: http://www.bostonscientific.com/Device.bsci?page=HCP_Overview &navRe1Id=1000.1003&method=D . . . , accessed Jul. 18, 2008 (4 pages).
J.D. Paulson, M.D., et al., "Development of Flexible Culdoscopy," The Journal of the American Association of Gynecologic Laparoscopists, Nov. 1999, vol. 6, No. 4, pp. 487-490.
H. Seifert, et al., "Retroperitoneal Endoscopic Debridement for Infected Peripancreatic Necrosis," The Lancet, Research Letters, vol. 356, Aug. 19, 2000, pp. 653-655.
K.E. Mönkemüller, M.D., et al., "Transmural Drainage of Pancreatic Fluid Collections Without Electrocautery Using the Seldinger Technique," Gastrointestinal Endoscopy, vol. 48, No. 2, 1998, pp. 195-200, (Received Oct. 3, 1997; Accepted Mar. 31, 1998).
D. Wilhelm et al., "An Innovative, Safe and Sterile Sigmoid Access (ISSA) for NOTES," Endoscopy 2007, vol. 39, pp. 401-406.
Nakazawa et al., "Radiofrequency Ablation of Hepatocellular Carcinoma: Correlation Between Local Tumor Progression After Ablation and Ablative Margin," AJR, 188, pp. 480-488 (Feb. 2007).
Miklavčič et al., "A validated model of in vivo electric field distribution in tissues for electrochemotherapy and for DNA electrotransfer for gene therapy," Biochimica et Biophysica Acta, 1523, pp. 73-83 (2000).
Evans, "Ablative and cathether-delivered therapies for colorectal liver metastases (CRLM)," EJSO, 33, pp. S64-S75 (2007).
Wong et al., "Combined Percutaneous Radiofrequency Ablation and Ethanol Injection for Hepatocellular Carcinoma in High-Risk Locations," AJR, 190, pp. W187-W195 (2008).
Heller et al., "Electrically mediated plasmid DNA delivery to hepatocellular carcinomas in vivo," Gene Therapy, 7, pp. 826-829 (2000).
Widera et al., "Increased DNA Vaccine Delivery and Immunogenicity by Electroporation in Vivo," The Journal of Immunology, 164, pp. 4635-4640 (2000).

(56) References Cited

OTHER PUBLICATIONS

Weaver et al., "Theory of electroporation: A review," Bioelectrochemistry and Bioenergetics, 41, pp. 135-160 (1996).

Mulier et al., "Radiofrequency Ablation Versus Resection for Resectable Colorectal Liver Metastases: Time for a Randomized Trial?" Annals of Surgical Oncology, 15(1), pp. 144-157 (2008).

Link et al., "Regional Chemotherapy of Nonresectable Colorectal Liver Metastases with Mitoxanthrone, 5-Fluorouracil, Folinic Acid, and Mitomycin C May Prolong Survival," Cancer, 92, pp. 2746-2753 (2001).

Guyton et al., "Membrane Potentials and Action Potentials," W.B. Sanders, ed. Textbook of Medical Physiology, p. 56 (2000).

Guyton et al., "Contraction of Skeletal Muscle," Textbook of Medical Physiology, pp. 82-84 (2000).

"Ethicon Endo-Surgery Novel Investigational Notes and SSL Devices Featured in 15 Presentations at Sages," Apr. 22, 2009 Press Release; URL http://www.jnj.com/connect/news/all/20090422_152000; accessed Aug. 28, 2009 (3 pages).

"Ethicon Endo-Surgery Studies Presented at DDW Demonstrate Potential of Pure NOTES Surgery With Company's Toolbox," Jun. 3, 2009 Press Release; URL http://www.jnj.com/connect/news/product/20090603_120000; accessed Aug. 28, 2009 (3 pages).

Castellvi et al., "Hybrid Transvaginal NOTES Sleeve Gastrectomy in a Porcine Model Using a Magnetically Anchored Camera and Novel Instrumentation," Abstract submitted along with Poster at SAGES Annual Meeting in Phoenix, AZ, Apr. 22, 2009 (1 page).

Castellvi et al., "Hybrid Transvaginal NOTES Sleeve Gastrectomy in a Porcine Model Using a Magnetically Anchored Camera and Novel Instrumentation," Poster submitted along with Abstract at SAGES Annual Meeting in Phoenix, AZ, Apr. 22, 2009 (1 page).

OCTO Port Modular Laparoscopy System for Single Incision Access, Jan. 4, 2010; URL http://www.medgadget.com/archives/2010/01/octo_port_modular_laparo . . . ; accessed Jan. 5, 2010 (4 pages).

Hakko Retractors, obtained Aug. 25, 2009 (5 pages).

Zadno et al., "Linear Superelasticity in Cold-Worked Ni—Ti," Engineering Aspects of Shape Memory Alloys, pp. 414-419 (1990).

How Stuff Works "How Smart Structures Will Work," http://science.howstuffworks.com/engineering/structural/smart-structure1.htm; accessed online Nov. 1, 2011 (3 pages).

Instant Armor: Science Videos—Science News—ScienCentral; http://www.sciencentral.com/articles./view.php3?article_id=218392121; accessed online Nov. 1, 2011 (2 pages).

Stanway, Smart Fluids: Current and Future Developments. Material Science and Technology, 20, pp. 931-939, 2004; accessed online Nov. 1, 2011 at http://www.dynamics.group.shef.ac.uk/smart/smart.htm (7 pages).

Jolly et al., Properties and Applications of Commercial Magnetorheological Fluids. SPIE 5th Annual Int. Symposium on Smart Structures and Materials, 1998 (18 pages).

U.S. Appl. No. 13/013,131, filed Jan. 25, 2011.
U.S. Appl. No. 13/013,147, filed Jan. 25, 2011.
U.S. Appl. No. 13/036,895, filed Feb. 28, 2011.
U.S. Appl. No. 13/267,251, filed Oct. 6, 2011.
U.S. Appl. No. 13/325,791, filed Dec. 14, 2011.
U.S. Appl. No. 13/399,358, filed Feb. 17, 2012.
U.S. Appl. No. 13/420,805, filed Mar. 15, 2012.
U.S. Appl. No. 13/420,818, filed Mar. 15, 2012.
U.S. Appl. No. 13/425,103, filed Mar. 20, 2012.

International Search Report for PCT/US2012/026049, Jun. 21, 2012 (5 pages).

Rutala et al. "Guideline for Disinfection and Sterilization in Healthcare Facilities, 2008" (available at http://www.cdc.gov/hicpac/Disinfection_Sterilization/13_11sterilizingPractices.html).

Bewlay et al., "Spinning" in ASM Handbook, vol. 14B, Metalworking: Sheet Forming (2006).

\* cited by examiner

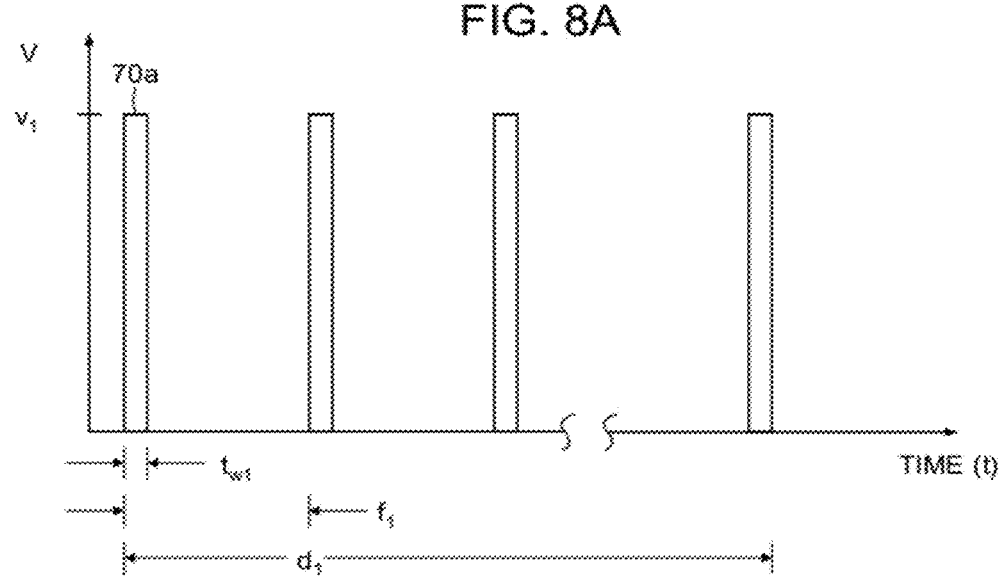
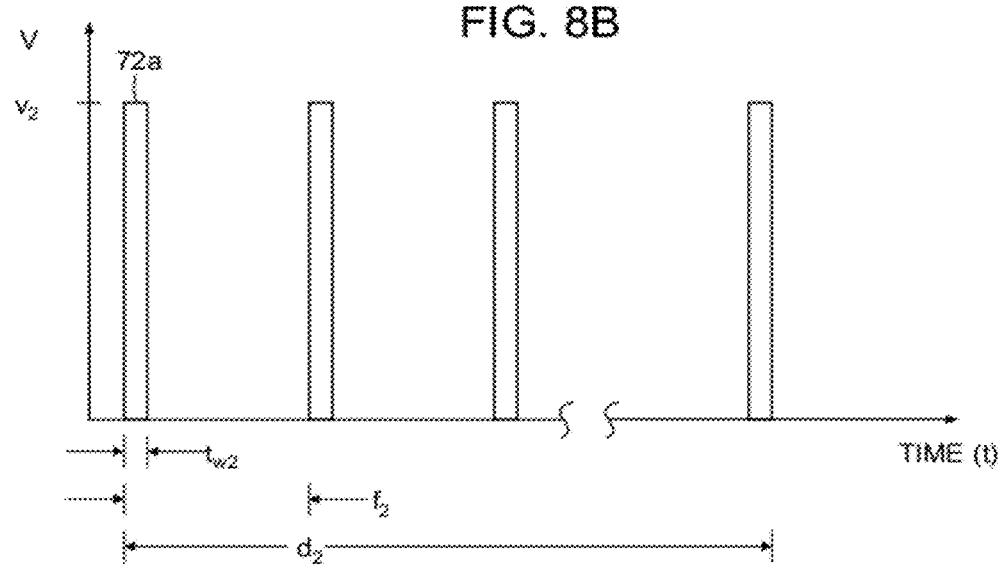

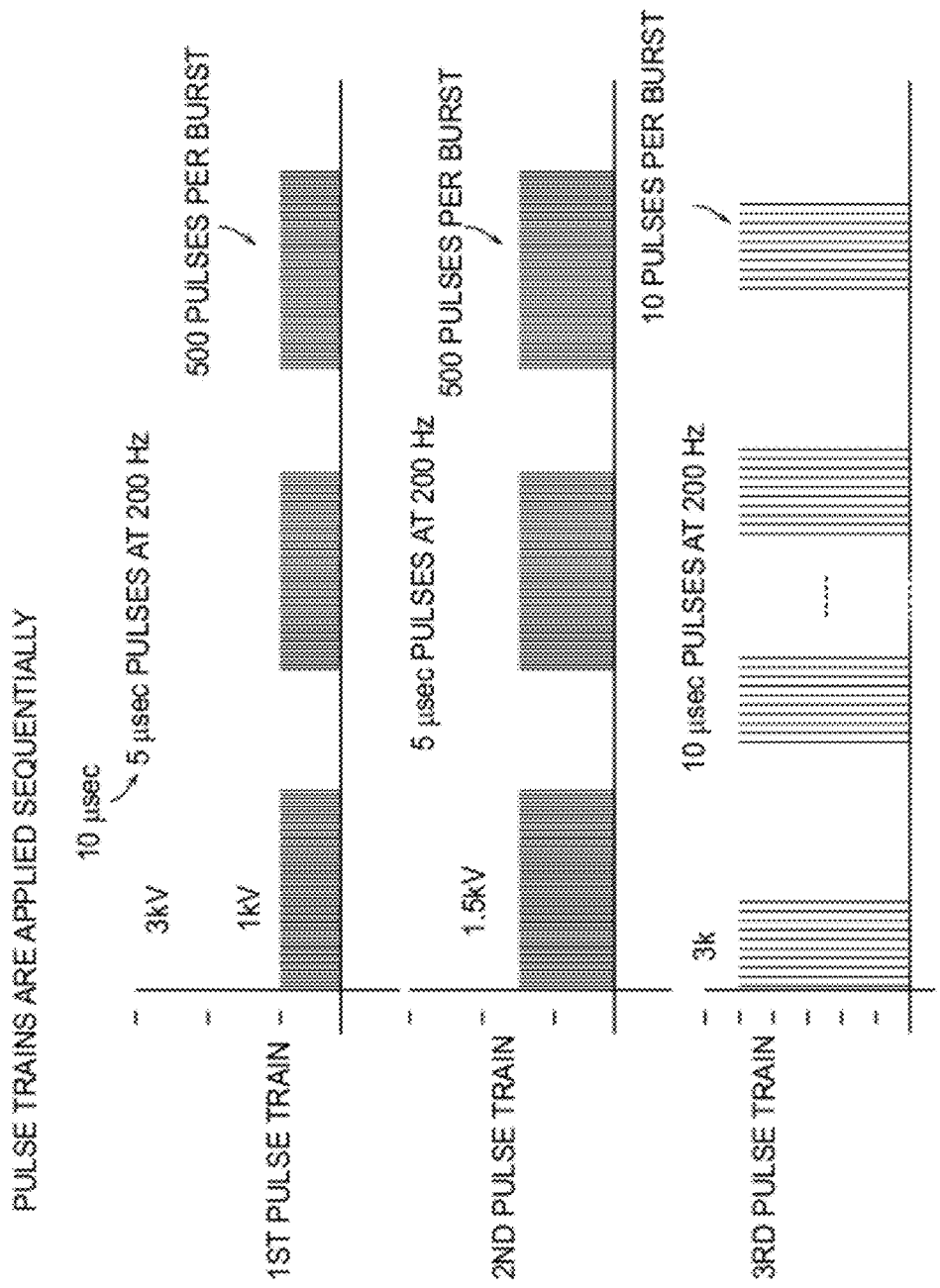

ELECTRICAL ABLATION DEVICES AND METHODS

CROSS-REFERENCE TO RELATED APPLICATIONS

This application is a continuation-in-part application of U.S. application Ser. No. 13/036,908, filed Feb. 28, 2011, titled "ELECTRICAL ABLATION DEVICES AND METHODS", which is incorporated herein by reference in its entirety.

BACKGROUND

Electrical ablation therapy has been used in medicine for the treatment of undesirable tissue, such as, for example, diseased tissue, cancer, malignant and benign tumors, masses, lesions, and other abnormal tissue growths. Apparatuses, systems, and methods for conventional ablation therapies may include electrical ablation therapies, such as, for example, high temperature thermal therapies including, focused ultrasound ablation, radiofrequency (RF) ablation, and interstitial laser coagulation, chemical therapies in which chemical agents are injected into the undesirable tissue to cause ablation, surgical excision, cryotherapy, radiation, photodynamic therapy, Moh's micrographic surgery, topical treatments with 5-fluorouracil, and laser ablation. Conventional electrical ablation therapies may suffer from some of the following limitations: cost, length of recovery, and extraordinary pain inflicted on the patient. In particular, one drawback of conventional electrical ablation therapies may be any permanent damage to healthy tissue surrounding the undesirable tissue due to detrimental thermal effects resulting from exposing the tissue to thermal energy generated by the electrical ablation device. For example, permanent damage to surrounding healthy tissue may occur when using high temperature thermal therapies to expose undesirable tissue to electric potentials sufficient to cause cell necrosis.

Additionally, conventional electrical ablation therapies to treat large masses of undesirable tissue may comprise treating a first portion of the tissue treatment region, repositioning the electrical ablation device, and treating the remaining portion of the tissue treatment region. Conventional electrical ablation therapies to treat large masses of undesirable tissue may suffer from some of the following additional limitations: small tissue treatment regions, repositioning the ablation apparatus, and multiple procedures. In particular, the surgeon or clinician may need to reposition the electrical ablation apparatus within the tissue treatment region and begin the process anew to treat large masses of undesirable tissue. Accordingly, more efficient electrical ablation apparatuses, systems, and methods for the treatment of undesirable tissue having reduced or no detrimental thermal effects to surrounding healthy tissue are desirable.

FIGURES

The various embodiments of electrical ablation devices and methods thereof described herein may be better understood by considering the following description in conjunction with the accompanying drawings.

FIGS. 8A-B are graphical representations of a series of electrical pulses that may be applied to undesirable tissue.

Figure 9:
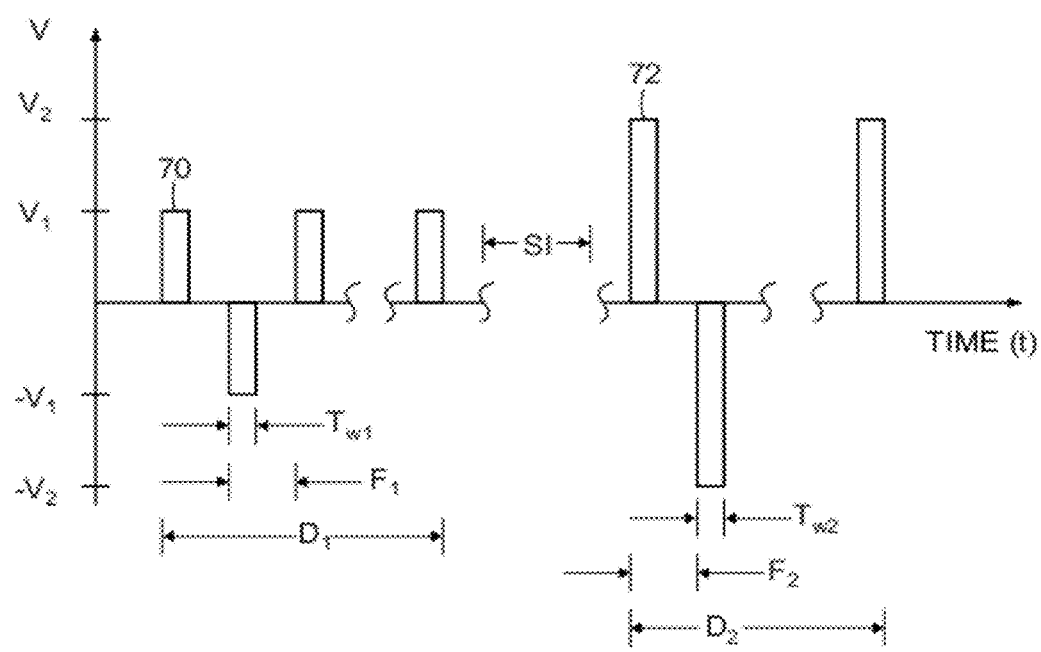

FIG. 9 is a graphical representation of a series of biphasic electrical pulses that may be applied to undesirable tissue to induce irreversible electroporation according to certain embodiments described herein.

Figure 10A:
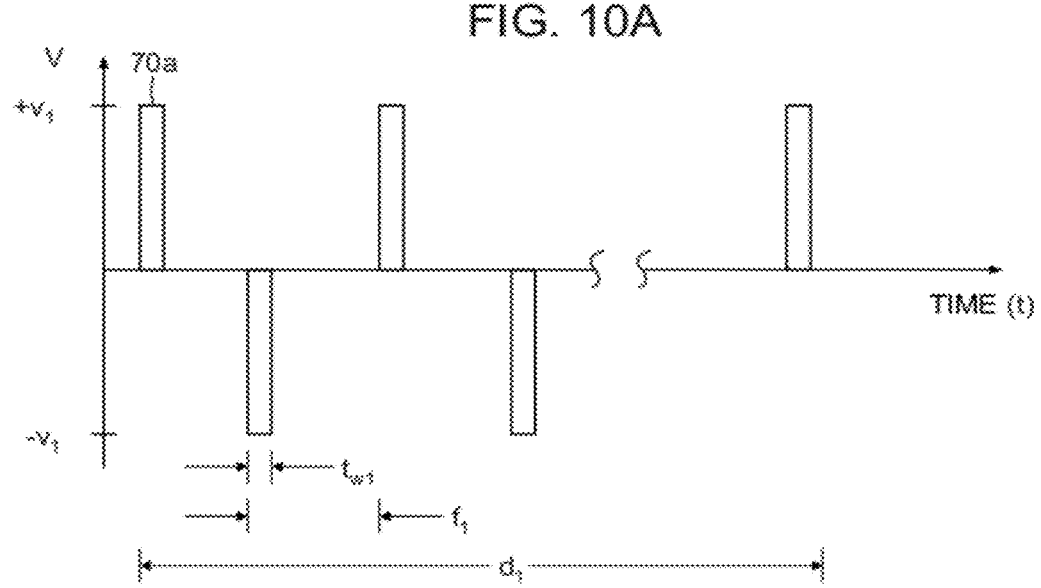
Figure 10B:
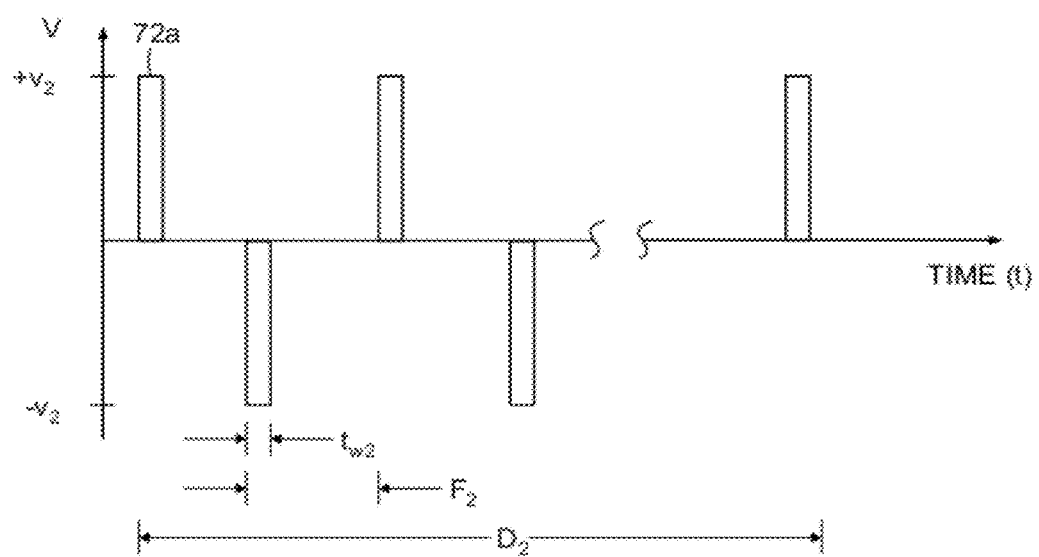

FIGS. 10A-B are graphical representations of a series of biphasic electrical pulses that may be applied to undesirable tissue.

Figure 11:
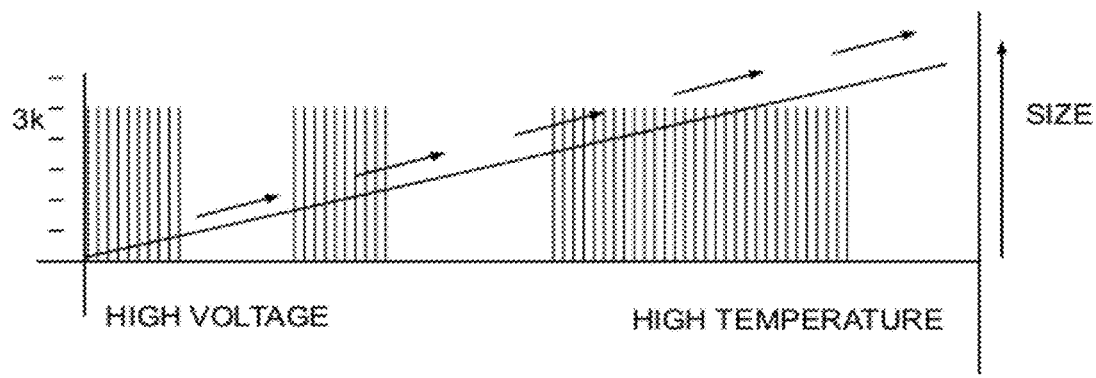

FIG. 11 is a graphical representation of a series of electrical pulses that may be applied to undesirable tissue.

Figure 12:
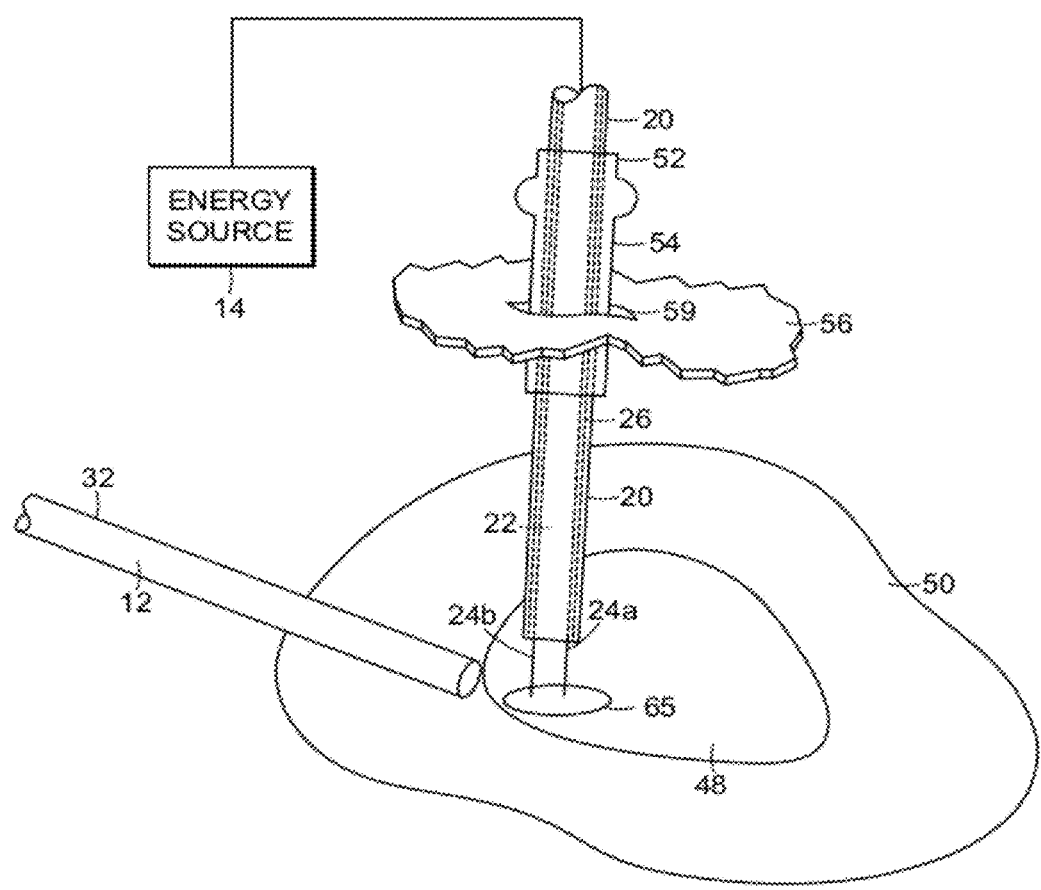

FIG. 12 illustrates the use of an electrical ablation system according to certain embodiments described herein.

Figure 13:
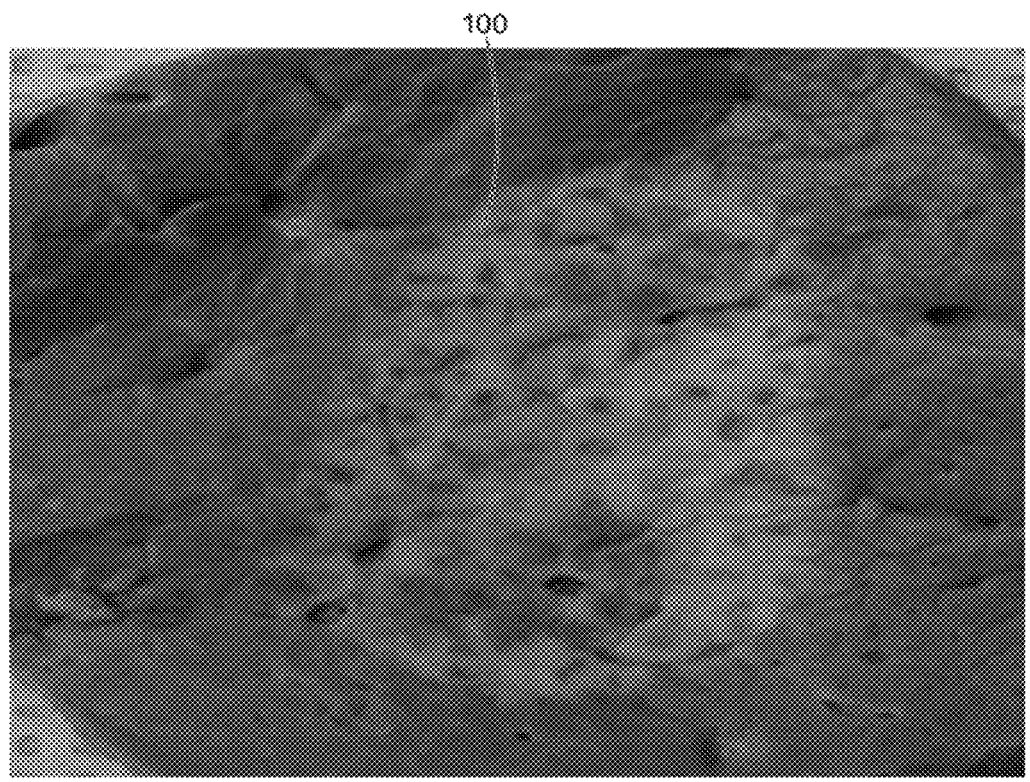

FIG. 13 is a photograph of a porcine liver after receiving a series of electrical pulses that may be applied to undesirable tissue to induce irreversible electroporation according to certain embodiments described herein.

Figure 14:
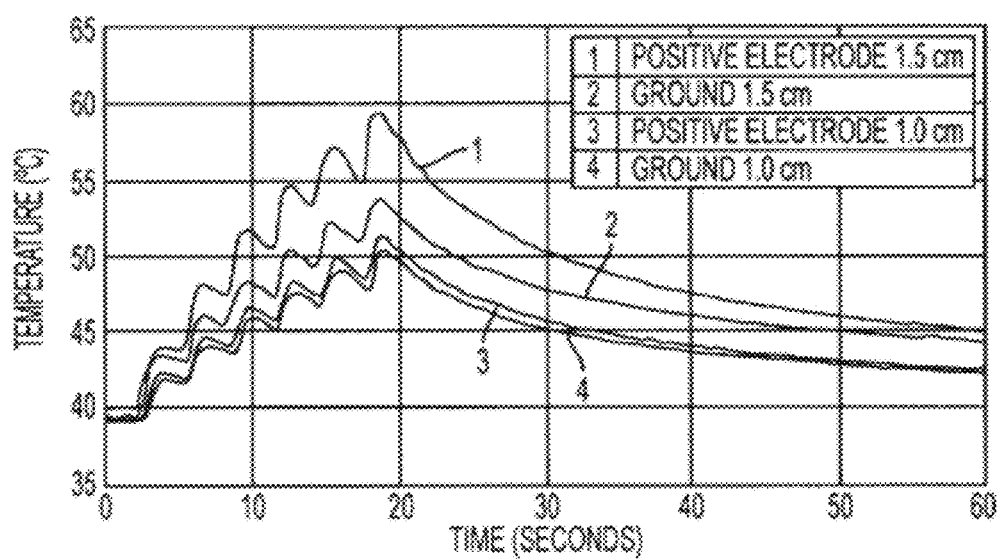

FIG. 14 is a graphical representation of electrode temperature during a series of electrical pulses that may be applied to undesirable tissue to induce irreversible electroporation according to certain embodiments described herein.

FIGS. 15A-D include photographs of porcine liver after receiving a series of electrical pulses that may be applied to undesirable tissue to induce irreversible electroporation according to certain embodiments described herein.

FIG. 16 is a graphical representation of a series of electrical pulses that may be applied to undesirable tissue.

Figure 17:
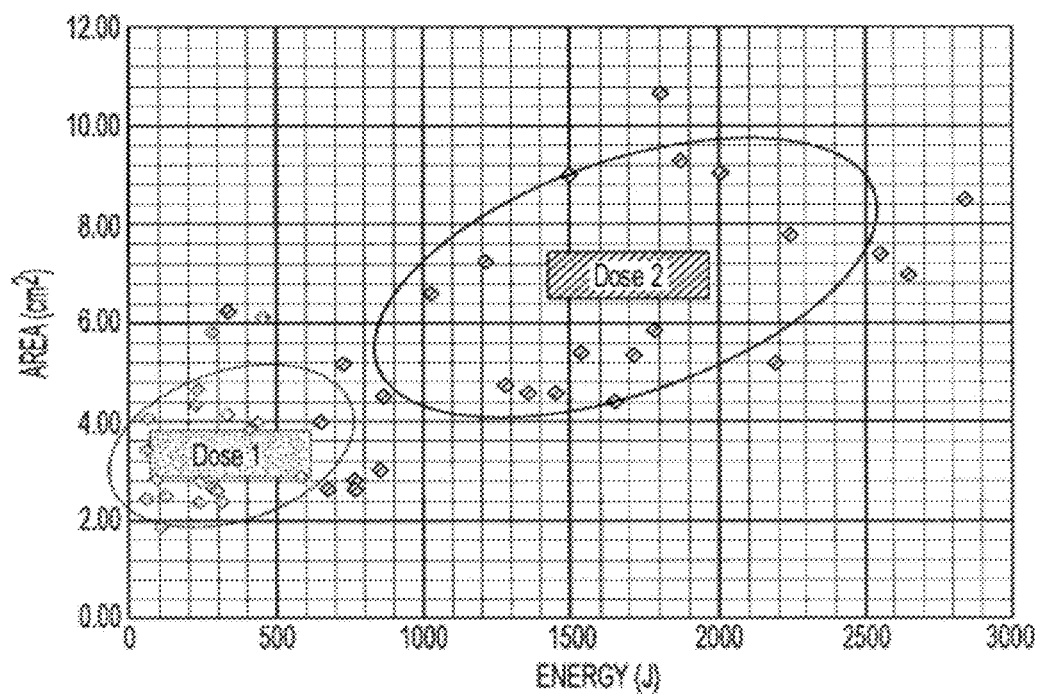

FIG. 17 is a graph illustrating the area of the necrotic zone of a porcine liver after receiving a series of electrical pulses that may be applied to undesirable tissue to induce irreversible electroporation according to certain embodiments described herein.

Figure 18A:
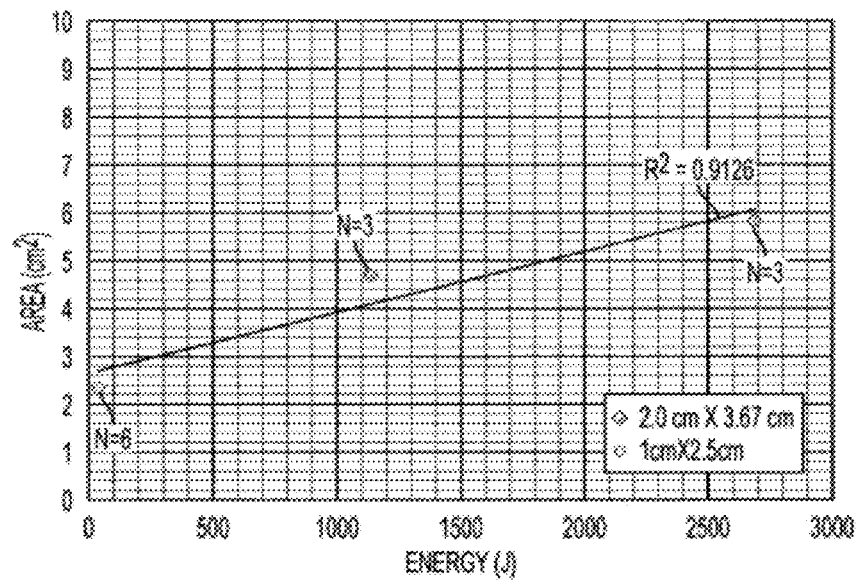

FIG. 18A is a graph illustrating the average area of the necrotic zone of a porcine liver after receiving a series of electrical pulses that may be applied to undesirable tissue to induce irreversible electroporation according to certain embodiments described herein.

Figure 18B:
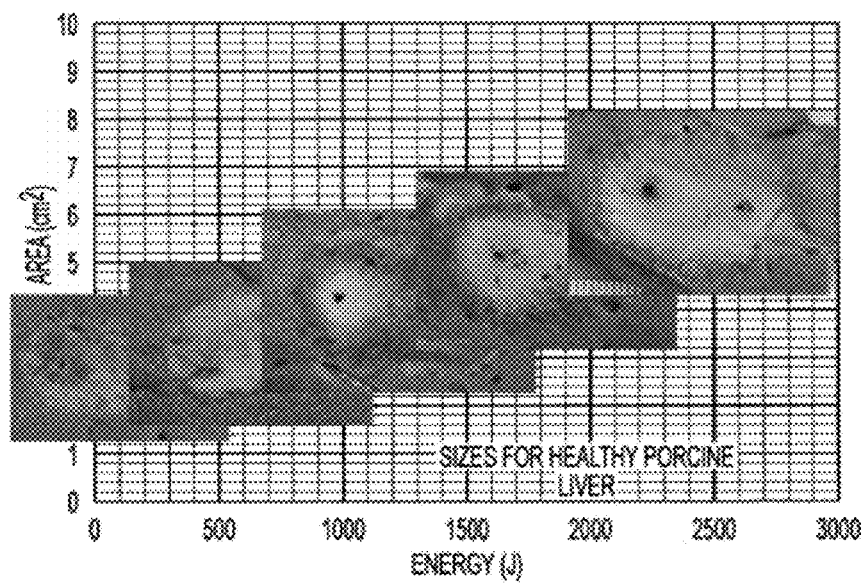

FIG. 18B includes photographs of porcine livers after receiving a series of electrical pulses that may be applied to undesirable tissue to induce irreversible electroporation according to certain embodiments described herein.

Figure 19:
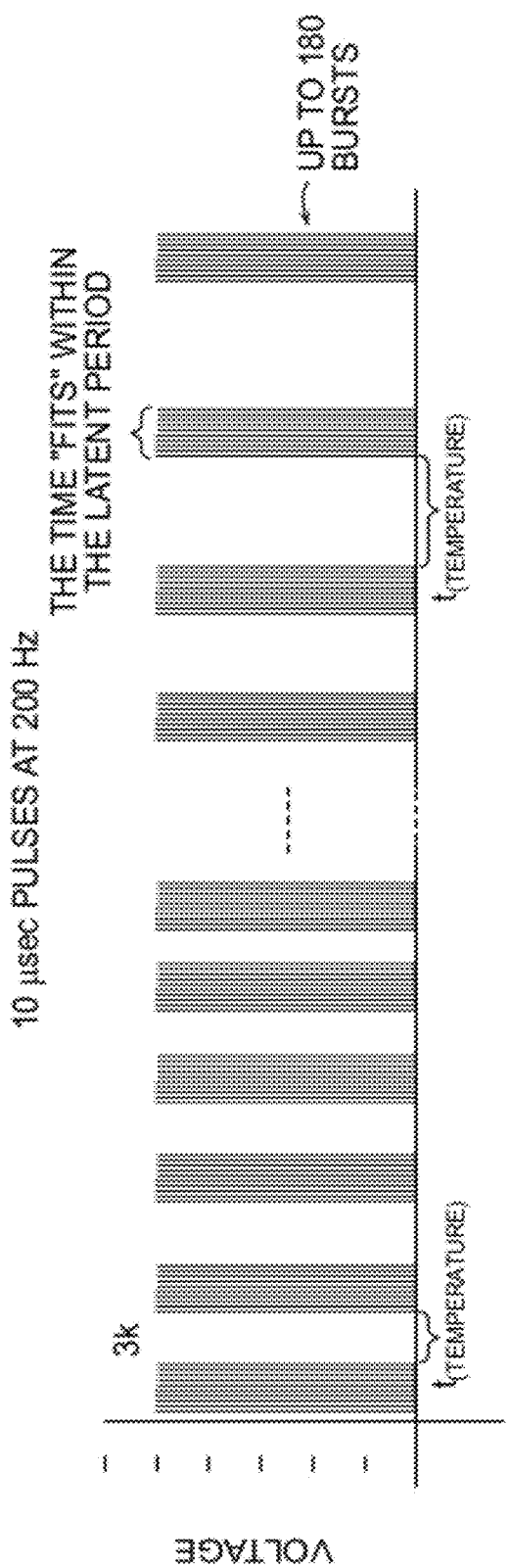

FIG. 19 is a graphical representation of a series of electrical pulses that may be applied to undesirable tissue.

Figure 20A:
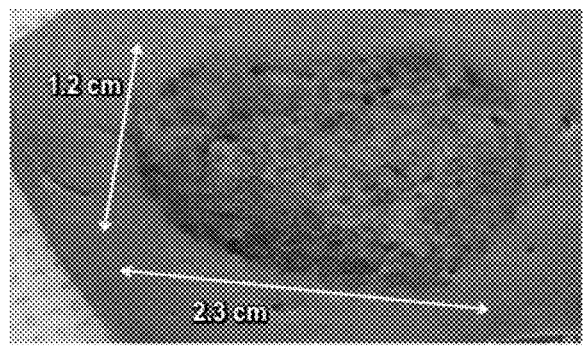
Figure 20B:
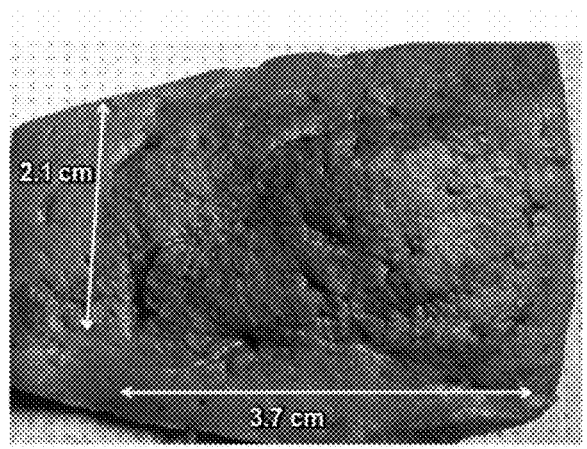
Figure 20C:
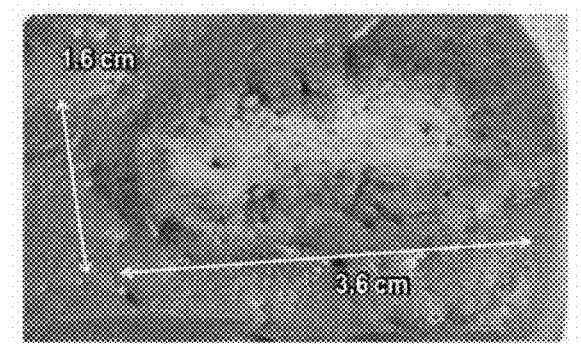

FIGS. 20A-C include photographs of porcine livers after receiving a series of electrical pulses that may be applied to undesirable tissue to induce irreversible electroporation according to certain embodiments described herein.

FIGS. 21-24 are graphs illustrating the electrode temperature in porcine liver after receiving a series of electrical pulses that may be applied to undesirable tissue to induce irreversible electroporation according to certain embodiments described herein.

Figure 25A:
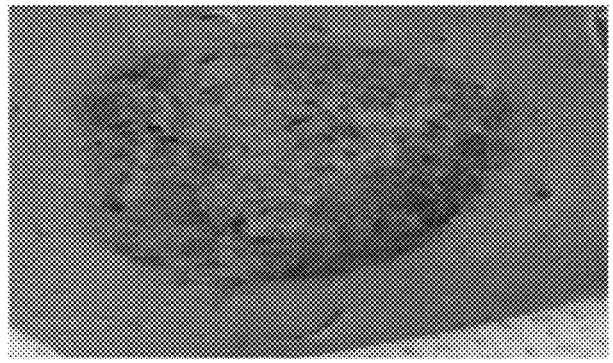
Figure 25B:
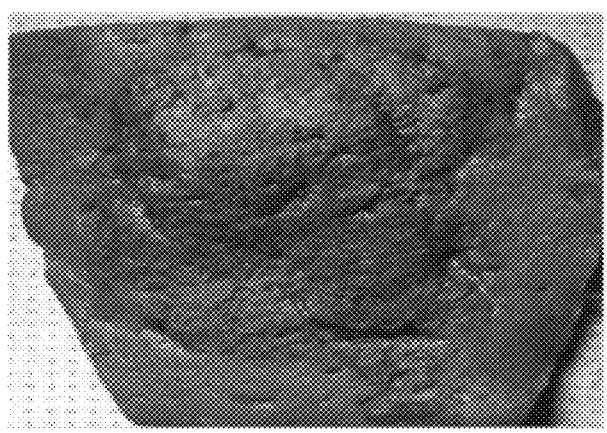
Figure 25C:
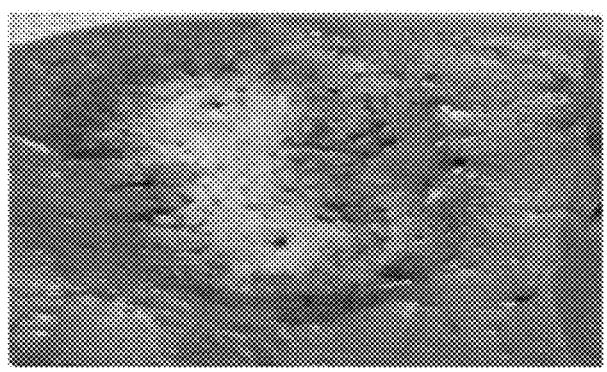

FIGS. 25A-C include photographs of porcine livers after receiving a series of electrical pulses that may be applied to undesirable tissue to induce irreversible electroporation according to certain embodiments described herein.

FIGS. 26A-F are graphical representations of simulated necrotic zones and thermal zones of porcine livers after receiving a series of electrical pulses that may be applied to undesirable tissue to induce irreversible electroporation according to certain embodiments described herein.

Figure 27:
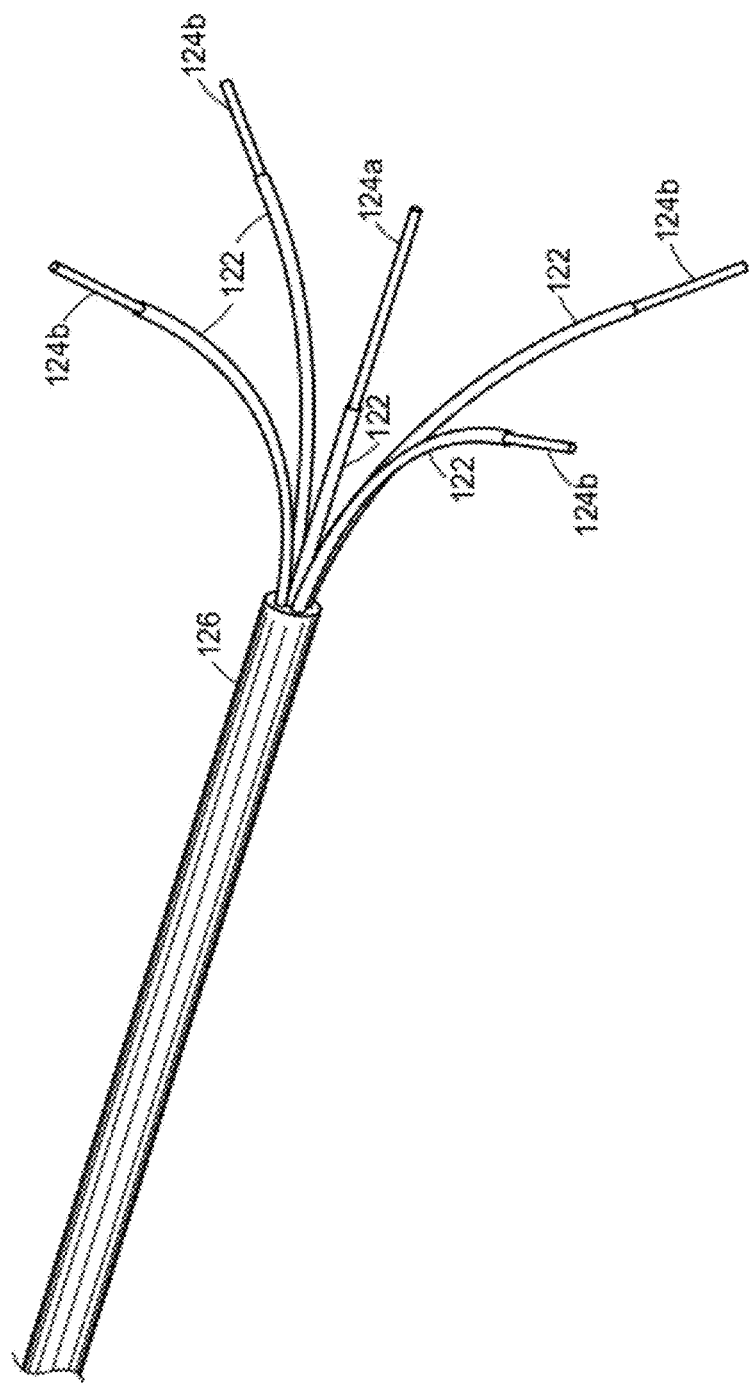

FIG. 27 illustrates an electrical ablation system, in a deployed state, according to certain embodiments described herein.

Figure 28A:
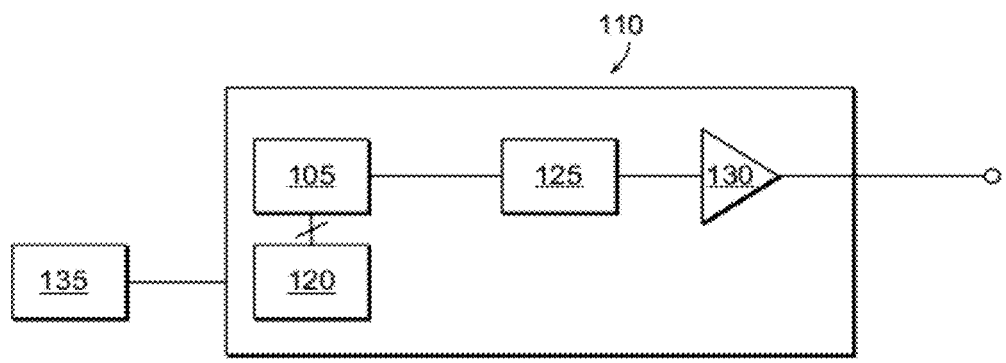
Figure 28B:
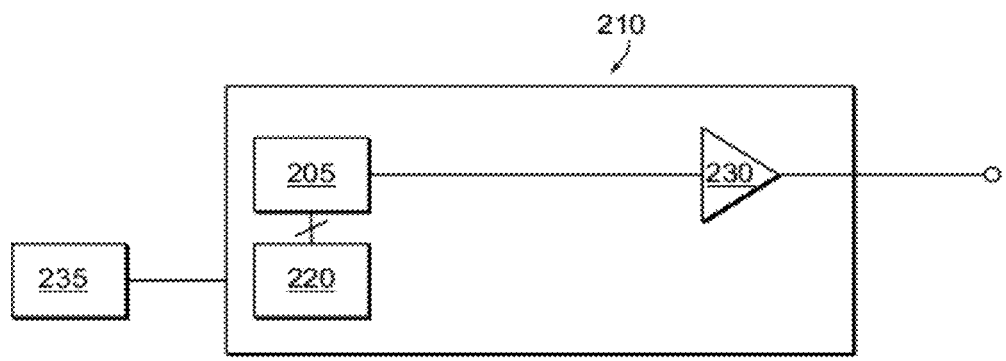
Figure 28C:
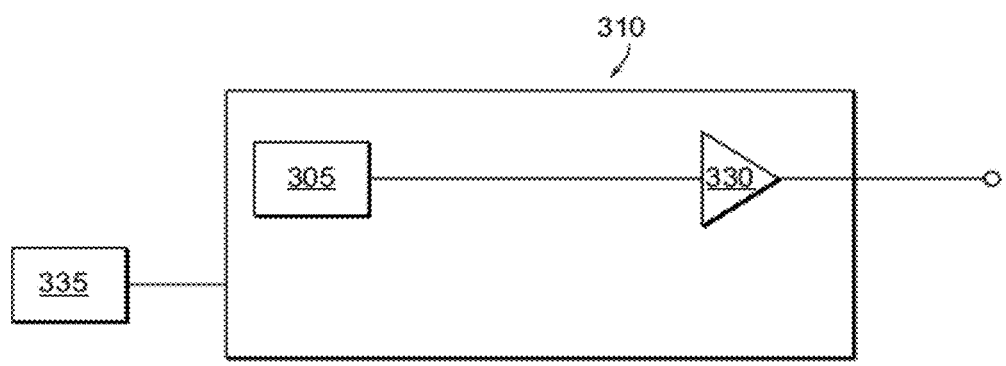

FIGS. 28A-C illustrates electrical ablation systems comprising a controller according to certain embodiments described herein.

Figure 29A:
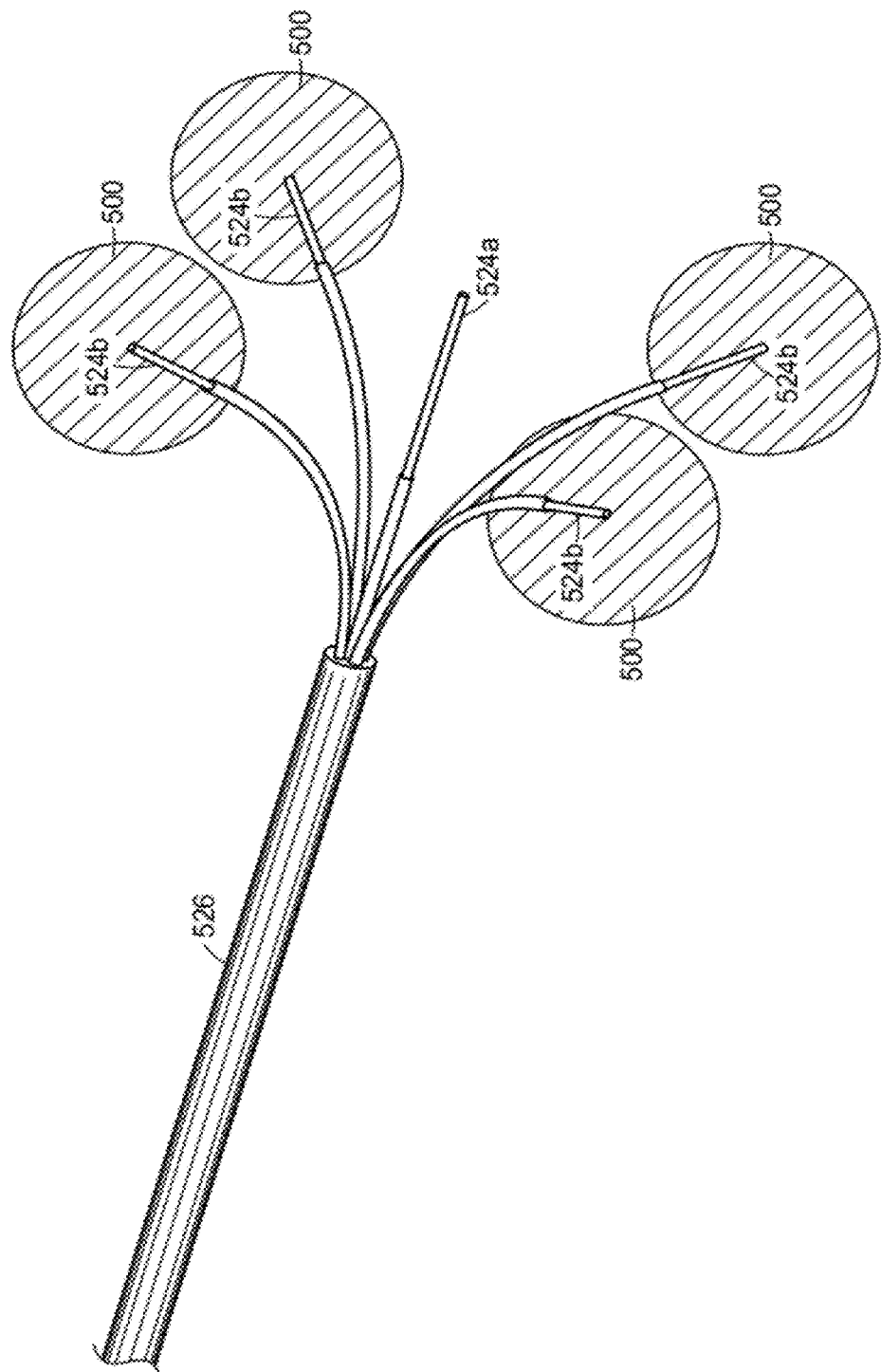
Figure 29B:
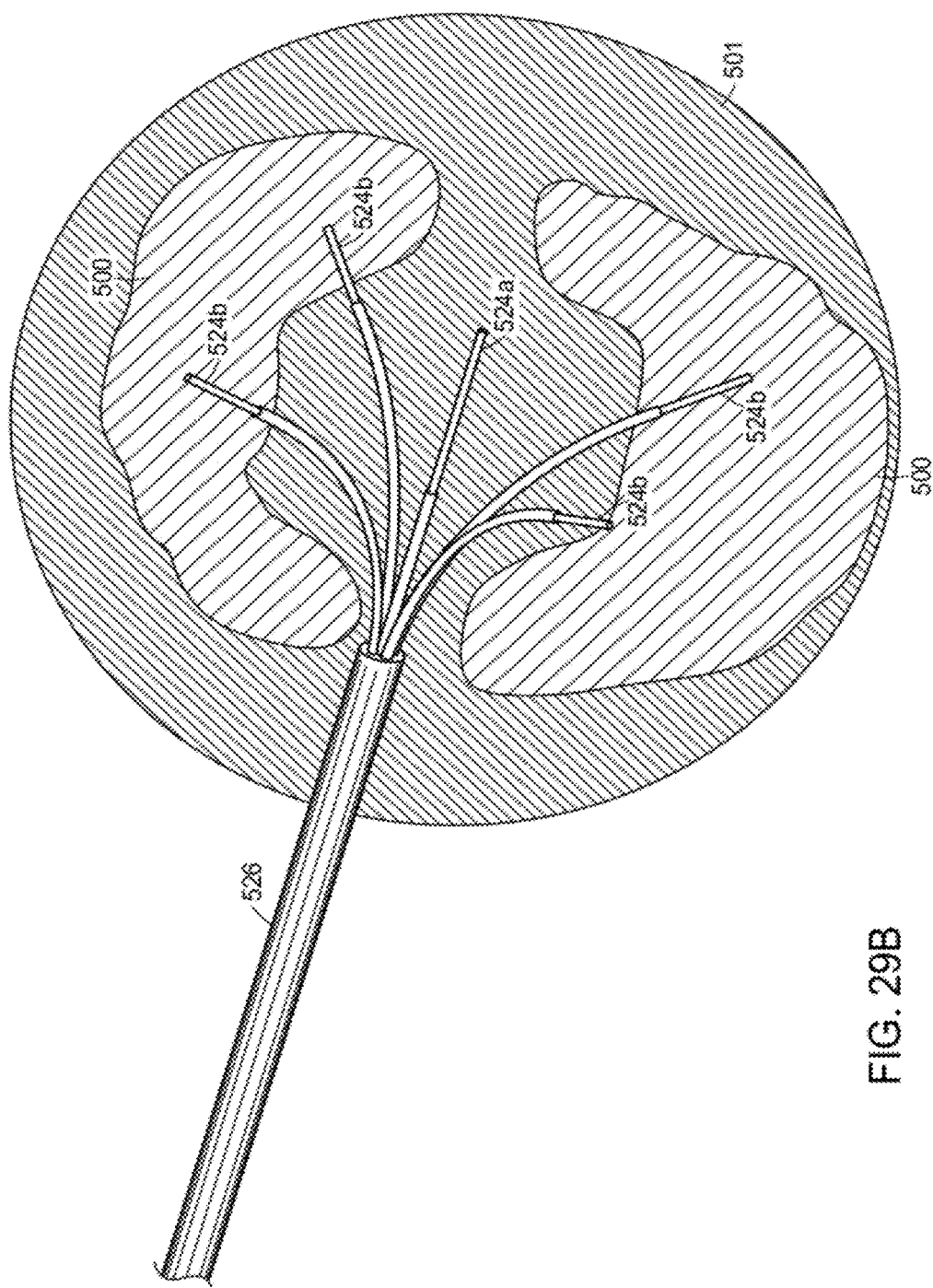

FIGS. 29A-B illustrate an electrical ablation system showing temperature zones according to certain embodiments described herein.

Figure 30:
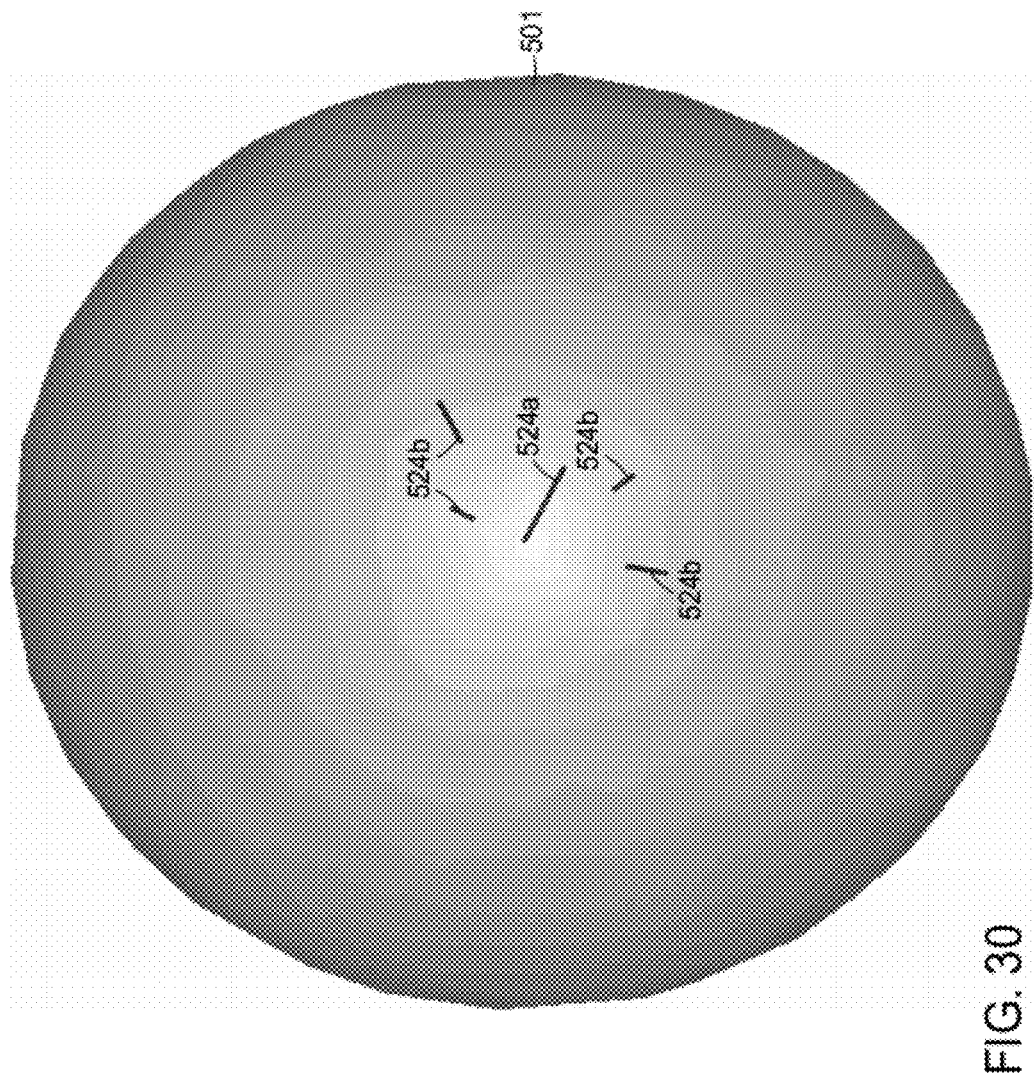

FIG. 30 is a finite element model of an electrical field in tissue of an electrical ablation system according to certain embodiments described herein.

Figure 31:
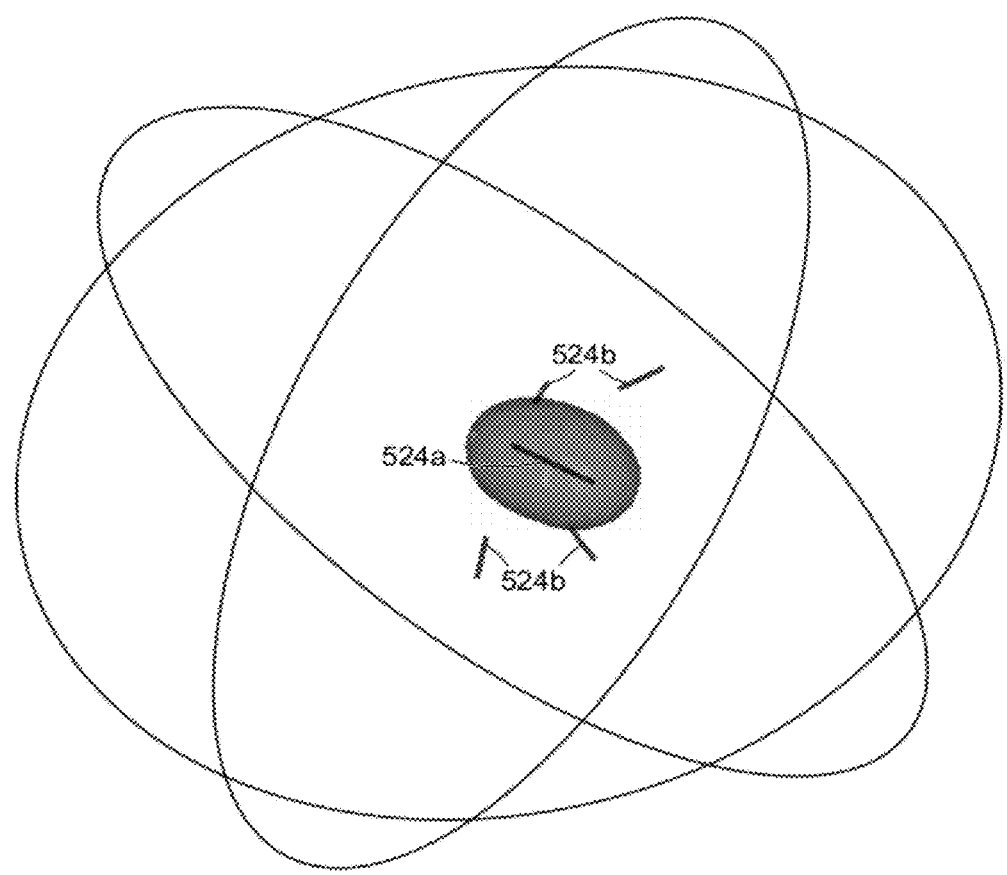

FIG. 31 is a graphical representation of an electric field strength sufficient to induce irreversible electroporation at body temperature (about 37° C.) according to certain embodiments described herein.

Figure 32:
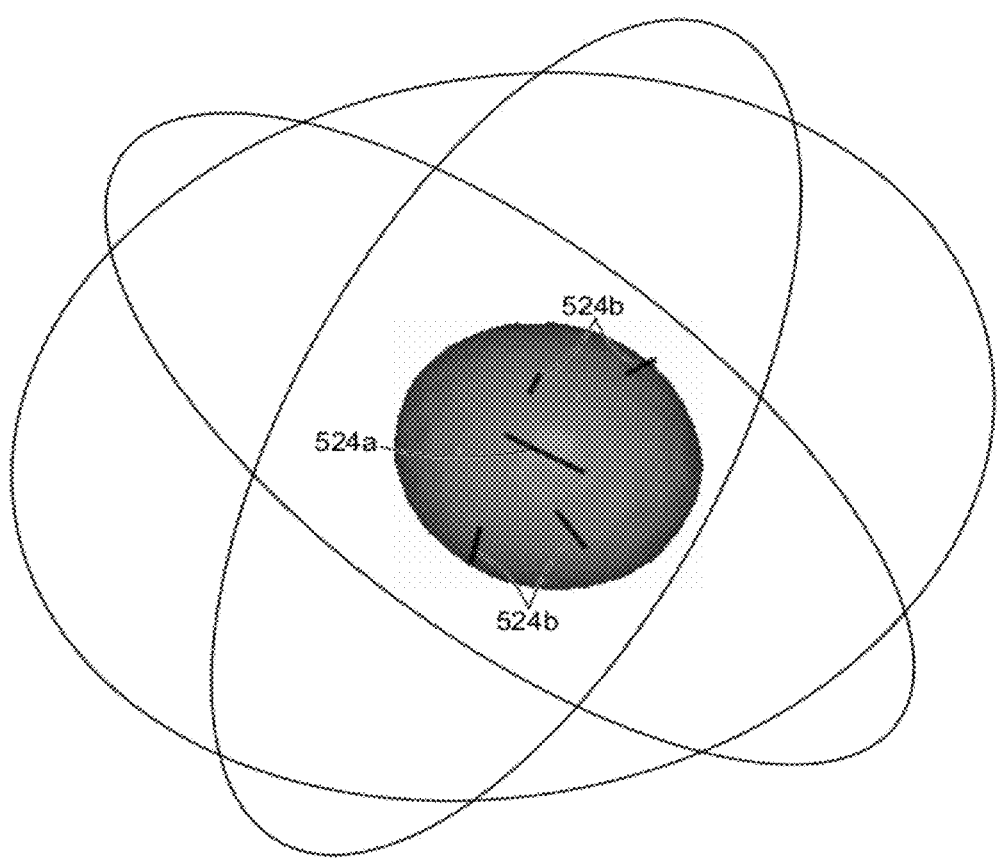

FIG. 32 is a graphical representation of an electric field strength sufficient to induce irreversible electroporation at an elevated temperature (about 55° C.) according to certain embodiments described herein.

Figure 33:
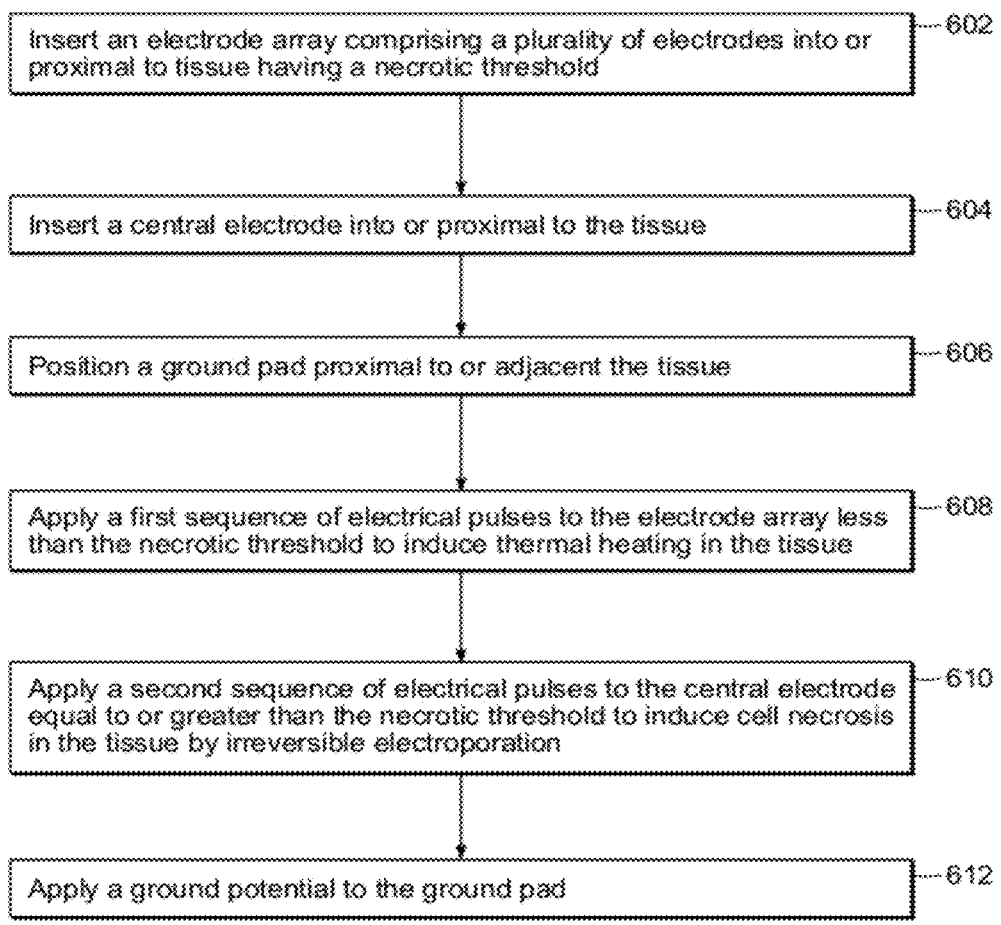

FIG. 33 is a flowchart illustrating an operation of an electrical ablation system according to certain embodiments described herein.

DESCRIPTION

Various embodiments are directed to electrical ablation apparatuses, systems, and methods for the treatment of undesirable tissue having reduced or no detrimental thermal effects to surrounding healthy tissue.

This disclosure describes various elements, features, aspects, and advantages of various embodiments of electrical ablation devices and methods thereof. It is to be understood that certain descriptions of the various embodiments have been simplified to illustrate only those elements, features and aspects that are relevant to a more clear understanding of the disclosed embodiments, while eliminating, for purposes of brevity or clarity, other elements, features and aspects. Any references to "various embodiments," "some embodiments," "one embodiment," or "an embodiment" generally means that a particular element, feature and/or aspect described in the embodiment is included in at least one embodiment. The phrases "in various embodiments," "in some embodiments," "in one embodiment," or "in an embodiment" may not refer to the same embodiment. Persons having ordinary skill in the art, upon considering the description herein, will recognize that various combinations or sub-combinations of the various embodiments and other elements, features, and aspects may be desirable in particular implementations or applications. However, because such other elements, features, and aspects may be readily ascertained by persons having ordinary skill in the art upon considering the description herein, and are not necessary for a complete understanding of the disclosed embodiments, a description of such elements, features, and aspects may not be provided. As such, it is to be understood that the description set forth herein is merely exemplary and illustrative of the disclosed embodiments and is not intended to limit the scope of the invention as defined solely by the claims.

All numerical quantities stated herein are approximate unless stated otherwise, meaning that the term "about" may be inferred when not expressly stated. The numerical quantities disclosed herein are to be understood as not being strictly limited to the exact numerical values recited. Instead, unless stated otherwise, each numerical value is intended to mean both the recited value and a functionally equivalent range surrounding that value. At the very least, and not as an attempt to limit the application of the doctrine of equivalents to the scope of the claims, each numerical parameter should at least be construed in light of the number of reported significant digits and by applying ordinary rounding techniques. Notwithstanding the approximations of numerical quantities stated herein, the numerical quantities described in specific examples of actual measured values are reported as precisely as possible.

All numerical ranges stated herein include all sub-ranges subsumed therein. For example, a range of "1 to 10" is intended to include all sub-ranges between and including the recited minimum value of 1 and the recited maximum value of 10. Any maximum numerical limitation recited herein is intended to include all lower numerical limitations. Any minimum numerical limitation recited herein is intended to include all higher numerical limitations.

As generally used herein, the terms "proximal" and "distal" generally refer to a clinician manipulating one end of an instrument used to treat a patient. The term "proximal" generally refers to the portion of the instrument closest to the clinician. The term "distal" generally refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

According to certain embodiments, an ablation apparatus may generally comprise first and second electrodes coupled to an energy source operative to generate and deliver a first sequence of electrical pulses and a second sequence of electrical pulses to tissue having a necrotic threshold, wherein the first sequence of electrical pulses delivers a first energy dose that is less than the necrotic threshold to induce thermal heating in the tissue and the second sequence of electrical pulses delivers a second energy dose equal to or greater than the necrotic threshold to induce cell necrosis in the tissue by irreversible electroporation. The necrotic threshold generally refers the electric field strength that induces cell necrosis by irreversible electroporation. The necrotic threshold may relate to at least the following parameters: cell type, temperature, electrical conductivity, pH and tissue perfusion. Table 1 illustrates the necrotic threshold for several cell types.

TABLE 1

| Cell Type | Necrotic Threshold |
|---|---|
| Hepatocyte (healthy porcine) | 800 V/cm |
| Renal cell (healthy porcine) | 1000 V/cm |

In certain embodiments, electrical ablation devices may generally comprise one or more electrodes configured to be positioned into or proximal to undesirable tissue in a tissue treatment region (e.g., a target site or a worksite). The tissue treatment region may have evidence of abnormal tissue growth. In general, the electrodes may comprise an electrically conductive portion (e.g., medical grade stainless steel, gold plated, etc.) and may be configured to electrically couple to an energy source. Once the electrodes are positioned into or proximal to the undesirable tissue, an energizing potential may be applied to the electrodes to create an electric field to which the undesirable tissue is exposed. The energizing potential (and the resulting electric field) may be characterized by various parameters, such as, for example, frequency, amplitude, pulse width (duration of a pulse or pulse length), and/or polarity. Depending on the diagnostic or therapeutic treatment to be rendered, a particular electrode may be configured either as an anode or a cathode, or a plurality of electrodes may be configured with at least one electrode configured as an anode and at least one other electrode configured as a cathode. Regardless of the initial polarity configuration, the polarity of the electrodes may be reversed by reversing the polarity of the output of the energy source.

In certain embodiments, a suitable energy source may comprise an electrical waveform generator. The electrical waveform generator may be configured to create an electric field that is suitable to induce thermal heating in the tissue without inducing cell necrosis in the tissue by irreversible electroporation at various electric field amplitudes and durations. The electrical waveform generator may be configured to create an electric field that is suitable to create irreversible electroporation in undesirable tissue at various electric field amplitudes and durations. The energy source may be configured to deliver electrical pulses in the form of direct-current (DC) and/or alternating-current (AC) voltage potentials (e.g., time-varying voltage potentials) to the electrodes. The energy source may also be configured to reverse the potential between the electrodes. The electrical pulses may be characterized by various parameters, such as, for example, frequency, amplitude, pulse width, polarity, total number of pulses, delay between pulses bursts, total number of pulses at a lower voltage, and total number of pulses at high voltage. The undesirable tissue may be heated by exposure to the electric potential difference across the electrodes. The undesirable tissue may be ablated by exposure to the electric potential difference across the electrodes.

In certain embodiments, the apparatuses, systems, and methods may be configured for minimally invasive ablation treatment of undesirable tissue through the use of irreversible electroporation. Minimally invasive ablation treatment of undesirable tissue may be characterized by the ability to ablate undesirable tissue in a controlled and focused manner having reduced or no thermally damaging effects to the surrounding healthy tissue. The apparatuses, systems, and methods may be configured to ablate undesirable tissue through the use of electroporation or electropermeabilization. Electroporation refers to the application of electric pulses to a cell membrane to cause an increase in the permeabilization of the cell membrane. The external electric field (i.e., electric potential/per unit length) applied to the cell may significantly increase the electrical conductivity and permeability of the plasma in the cell membrane.

More specifically, the apparatuses, systems, and methods may be configured to ablate undesirable tissue through the use of irreversible electroporation. Irreversible electroporation refers to the application of an electric field of a specific magnitude and duration to a cell membrane such that the permeabilization of the cell membrane cannot be reversed. One of the primary parameters affecting the transmembrane potential is the potential difference across the cell membrane.

The destabilizing potential may form pores in the cell membrane when the potential across the cell membrane exceeds its dielectric strength causing the cell to die under a process known as apoptosis and/or necrosis. Irreversible electroporation may induce localized heating of the tissue surrounding the electrodes. Irreversible electroporation may lead to cell death without inducing a significant amount of heat in the cell membrane.

The application of irreversible electroporation pulses to cells may be an effective way for ablating large volumes of undesirable tissue with no or minimal detrimental thermal effects to the surrounding healthy tissue. Without wishing to be bound to any particular theory, it is believed that irreversible electroporation destroys cells with no or minimal heat, and thus, may not destroy the cellular support structure or regional vasculature. A destabilizing irreversible electroporation pulse, suitable to cause cell death without inducing a significant amount of thermal damage to the surrounding healthy tissue, may have amplitude in the range of several hundred to several thousand volts and may be generally applied across biological membranes over a distance of several millimeters, for example, for a relatively long duration of 1 μs to 100 ms. Thus, the undesirable tissue may be ablated in-vivo through the delivery of destabilizing electric fields by quickly causing cell necrosis.

The apparatuses, systems, and methods for electrical ablation therapy may be adapted for use in minimally invasive surgical procedures to access the tissue treatment region in various anatomic locations, such as, for example, the brain, lungs, breast, liver, gall bladder, pancreas, prostate gland, and various internal body lumen defined by the esophagus, stomach, intestine, colon, arteries, veins, anus, vagina, cervix, fallopian tubes, and the peritoneal cavity. Minimally invasive electrical ablation devices may be introduced to the tissue treatment region though a small opening formed in the patient's body using a trocar or through a natural body orifice such as the mouth, anus, or vagina using translumenal access techniques known as Natural Orifice Translumenal Endoscopic Surgery (NOTES)™. Once the electrical ablation devices (e.g., electrodes) are located into or proximal to the undesirable tissue in the treatment region, electric field potentials may be applied by the energy source to the undesirable tissue. The electrical ablation devices may comprise portions that may be inserted into the tissue treatment region percutaneously (e.g., where access to inner organs or other tissue is done via needle-puncture of the skin). Other portions of the electrical ablation devices may be introduced into the tissue treatment region endoscopically (e.g., laparoscopically and/or thoracoscopically) through trocars or channels of the endoscope, through small incisions, or transcutaneously (e.g., where electric pulses are delivered to the tissue treatment region through the skin). An electrical ablation device is described in commonly owned U.S. Patent Publication No. 2010/0179530, entitled, "ELECTRICAL ABLATION DEVICES" filed Jan. 12, 2009.

Figure 1:
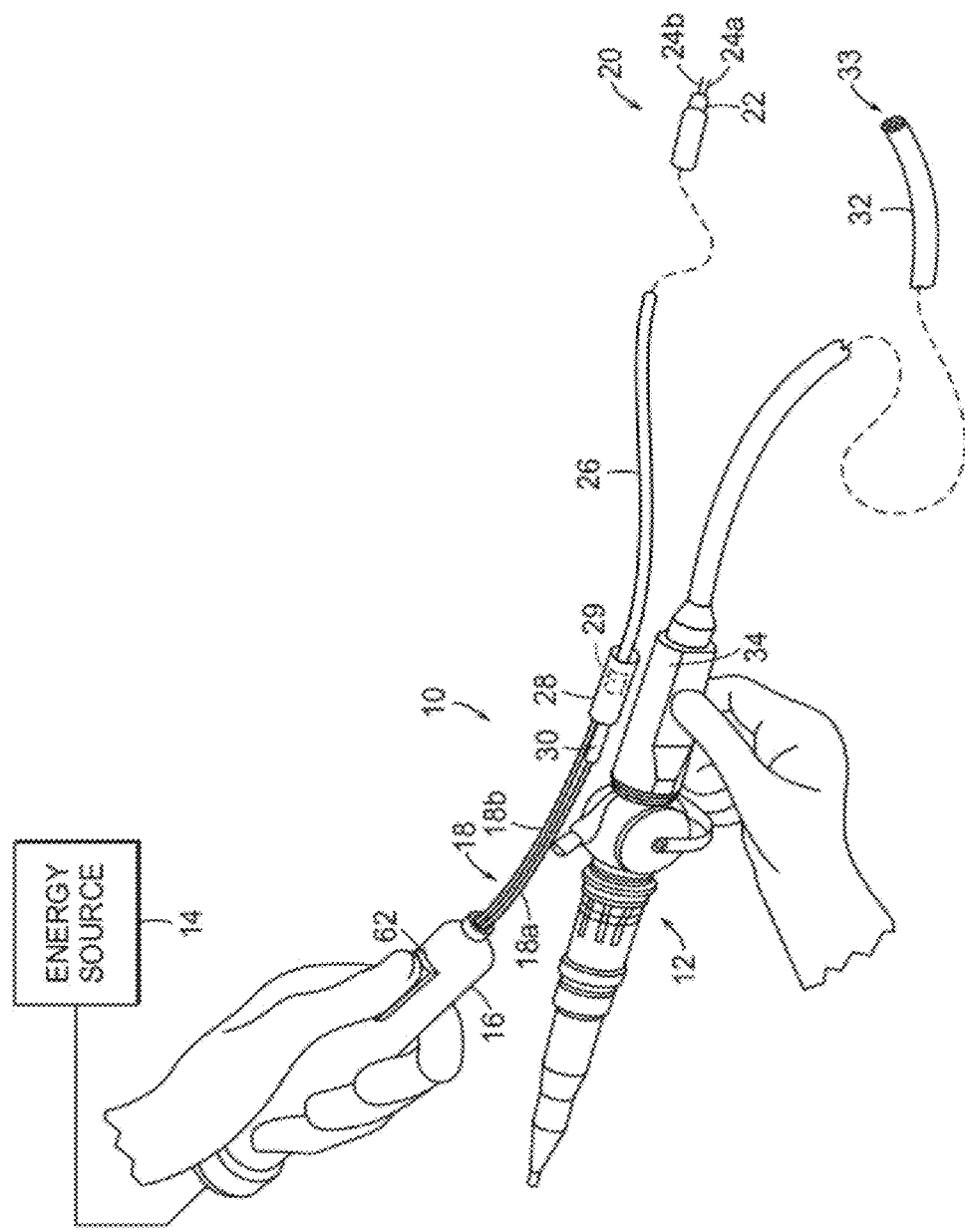
FIG. 1 illustrates an electrical ablation system according to certain embodiments described herein.

FIG. 1 illustrates one embodiment of an electrical ablation system 10. The electrical ablation system 10 may be employed to ablate undesirable tissue, such as, for example, diseased tissue, cancer, malignant and benign tumors, masses, lesions, and other abnormal tissue growths in a tissue treatment region using electrical energy. The electrical ablation system 10 may be configured to treat a number of lesions and ostepathologies comprising metastatic lesions, tumors, fractures, infected sites, and inflamed sites in a tissue treatment region using electrical energy. The electrical ablation system 10 may be configured to be positioned within a patient's natural body orifice, e.g., the mouth, anus, and vagina, and/or advanced through internal body lumen or cavities, e.g., the esophagus, stomach, intestines, colon, cervix, and urethra, to reach the tissue treatment region. The electrical ablation system 10 may be configured to be positioned and passed through a small incision or keyhole formed through the patient's skin or abdominal wall using a trocar to reach the tissue treatment region. The tissue treatment region may be located in the patient's brain, lung, breast, liver, gall bladder, pancreas, prostate gland, various internal body lumen defined by the esophagus, stomach, intestine, colon, arteries, veins, anus, vagina, cervix, fallopian tubes, and the peritoneal cavity. The electrical ablation system 10 may be used in conjunction with endoscopic, laparoscopic, thoracoscopic, open surgical procedures via small incisions or keyholes, percutaneous techniques, transcutaneous techniques, and/or external non-invasive techniques, and any combinations thereof.

Once positioned into or proximate the tissue treatment region, the electrical ablation system 10 may be actuated (e.g., energized) to ablate the undesirable tissue. In one embodiment, the electrical ablation system 10 may be configured to treat diseased tissue in the gastrointestinal tract, esophagus, lung, and/or stomach that may be accessed orally. In another embodiment, the electrical ablation system 10 may be adapted to treat undesirable tissue in the liver or other organs that may be accessible using translumenal access techniques, such as, for example, NOTES™ techniques where the electrical ablation devices may be initially introduced through a natural body orifice and then advanced to the tissue treatment site by puncturing the walls of internal body lumen. In various embodiments, the electrical ablation system 10 may be adapted to treat undesirable tissue in the brain, lung, breast, liver, gall bladder, pancreas, or prostate gland, using one or more electrodes positioned percutaneously, transcutaneously, translumenally, minimally invasively, and/or through open surgical techniques, or any combination thereof.

In one embodiment, the electrical ablation system 10 may be employed in conjunction with a flexible endoscope 12, as well as a rigid endoscope, laparoscope, or thoracoscope, such as the GIF-100 model available from Olympus Corporation. In one embodiment, the endoscope 12 may be introduced to the tissue treatment region trans-anally through the colon, trans-orally through the esophagus and stomach, trans-vaginally through the cervix, transcutaneously, or via an external incision or keyhole formed in the abdomen in conjunction with a trocar. The electrical ablation system 10 may be inserted and guided into or proximate the tissue treatment region using the endoscope 12. In other embodiments, the endoscope 12 is not utilized, and instead other techniques, such as, for example, ultrasound or a computerized tomography (CT) scan, may be used to determine proper instrument placement during the procedure.

In the embodiment illustrated in FIG. 1, the endoscope 12 comprises an endoscope handle 34 and an elongate relatively flexible shaft 32. The distal end of the flexible shaft 32 may comprise a light source and a viewing port. Optionally, the flexible shaft 32 may define one or more channels for receiving various instruments therethrough, such as, for example, electrical ablation devices. Images within the field of view of the viewing port may be received by an optical device, such as, for example, a camera comprising a charge coupled device (CCD) usually located within the endoscope 12, and transmitted to a display monitor (not shown) outside the patient. In one embodiment, the electrical ablation system 10 may comprise a plurality of electrical conductors 18, a hand piece 16 comprising an activation switch 62, and an energy source 14, such as, for example, an electrical waveform generator, electrically coupled to the activation switch 62 and the electrical ablation device 20. The electrical ablation device 20 may comprise a relatively flexible member or shaft 22 that may be introduced to the tissue treatment region using any of the techniques discussed above, such as, an open incision and a trocar, through one of more of the channels of the endoscope 12, percutaneously, or transcutaneously.

In one embodiment, one or more electrodes (e.g., needle electrodes, balloon electrodes), such as first and second electrodes 24*a,b* may extend out from the distal end of the electrical ablation device 20. In one embodiment, the first electrode 24*a* may be configured as the positive electrode and the second electrode 24*b* may be configured as the negative electrode. The first electrode 24*a* may be electrically connected to a first electrical conductor 18*a*, or similar electrically conductive lead or wire, which may be coupled to the positive terminal of the energy source 14 through the activation switch 62. The second electrode 24*b* may be electrically connected to a second electrical conductor 18*b*, or similar electrically conductive lead or wire, which may be coupled to the negative terminal of the energy source 14 through the activation switch 62. The electrical conductors 18*a,b* may be electrically insulated from each other and surrounding structures, except for the electrical connections to the respective electrodes 24*a,b*.

In certain embodiments, the electrical ablation device 20 may be configured to be introduced into or proximate the tissue treatment region using the endoscope 12 (laparoscope or thoracoscope), open surgical procedures, and/or external and non-invasive medical procedures. The electrodes 24*a,b* may be referred to herein as endoscopic or laparoscopic electrodes, although variations thereof may be inserted transcutaneously or percutaneously. In various embodiments, one or both electrodes 24*a,b* may be adapted and configured to slideably move in and out of a cannula, lumen, or channel defined within the flexible shaft 22.

When the electrodes 24*a,b* are positioned at the desired location into or proximate the tissue treatment region, the electrodes 24*a,b* may be connected to or disconnected from the energy source 14 by actuating or de-actuating the activation switch 62 on the hand piece 16. The activation switch 62 may be operated manually or may be mounted on a foot switch (not shown), for example. The electrodes 24*a,b* may deliver electric field pulses to the undesirable tissue. The electric field pulses may be characterized by various parameters, such as, for example, pulse shape, amplitude, frequency, pulse width, polarity, total number of pulses and duration. The electric field pulses may be sufficient to induce thermal heating in the undesirable tissue without inducing irreversible electroporation in the undesirable tissue. The electric field pulses may be sufficient to induce irreversible electroporation in the undesirable tissue. The induced potential may depend on a variety of conditions, such as, for example, tissue type, cell size, and electrical field pulse parameters. The transmembrane potential of a specific tissue type may primarily depend on the amplitude of the electric field and pulse width.

In certain embodiments, a protective sleeve or sheath 26 may be slidably disposed over the flexible shaft 22 and within a handle 28. In another embodiment, the sheath 26 may be slidably disposed within the flexible shaft 22 and the handle 28. The sheath 26 may be slideable and may be located over the electrodes 24*a,b* to protect the trocar and prevent accidental piercing when the electrical ablation device 20 is advanced therethrough. One or both of the electrodes 24*a,b* may be adapted and configured to slideably move in and out of a cannula, lumen, or channel formed within the flexible shaft 22. One or both of the electrodes 24a,b may be fixed in place. One of the electrodes 24a,b may provide a pivot about which the other electrode may be moved in an arc to other points in the tissue treatment region to treat larger portions of the diseased tissue that cannot be treated by fixing both of the electrodes 24a,b in one location. In one embodiment, one or both of the electrodes 24a,b may be adapted and configured to slideably move in and out of a working channel formed within a flexible shaft 32 of the endoscope 12 or may be located independently of the endoscope 12.

In one embodiment, the first and second electrical conductors 18a,b may be provided through the handle 28. The first electrode 24a may be slideably moved in and out of the distal end of the flexible shaft 22 using a slide member 30 to retract and/or advance the first electrode 24a. The second electrode 24b may be slideably moved in and out of the distal end of the flexible shaft 22 using the slide member 30 or a different slide member to retract and/or advance the second electrode 24b. One or both electrodes 24a,b may be coupled to the slide member 30, or additional slide members, to advance and retract the electrodes 24a,b and position the electrodes 24a,b. In this manner, the first and second electrodes 24a,b, which may be slidably movable within the cannula, lumen, or channel defined within the flexible shaft 22, may be advanced and retracted with the slide member 30. As shown in FIG. 1, the first electrical conductor 18a coupled to the first electrode 24a may be coupled to the slide member 30. In this manner, the first electrode 24a, which is slidably movable within the cannula, lumen, or channel within the flexible shaft 22, may be advanced and retracted with the slide member 30. In one embodiment, various slide members, such as the slide member 30, may be rotatable. Thus rotation of the slide member 30 may rotate the corresponding electrode(s) at the distal end of the electrical ablation device 20.

In various other embodiments, transducers or sensors 29 may be located in the handle 28 (or other suitable location) of the electrical ablation device 20 to sense the force with which the electrodes 24a,b penetrate the tissue in the tissue treatment region. This feedback information may be useful to determine whether one or both of the electrodes 24a,b have been properly inserted in the tissue treatment region. As is particularly well known, cancerous tumor tissue tends to be denser than healthy tissue, and thus greater force may be typically required to insert the electrodes 24a,b therein. The transducers or sensors 29 may provide feedback to the operator, surgeon, or clinician to physically sense when the electrodes 24a,b are placed within the cancerous tumor. The feedback information provided by the transducers or sensors 29 may be processed and displayed by circuits located either internally or externally to the energy source 14. The sensor 29 readings may be employed to determine whether the electrodes 24a,b have been properly located within the cancerous tumor thereby assuring that a suitable margin of error has been achieved in locating the electrodes 24a,b. The sensor 29 readings may also be employed to determine whether the pulse parameters need to be adjusted to achieve a desired result, such as, for example, reducing the intensity of muscular contractions in the patient.

Figure 2:
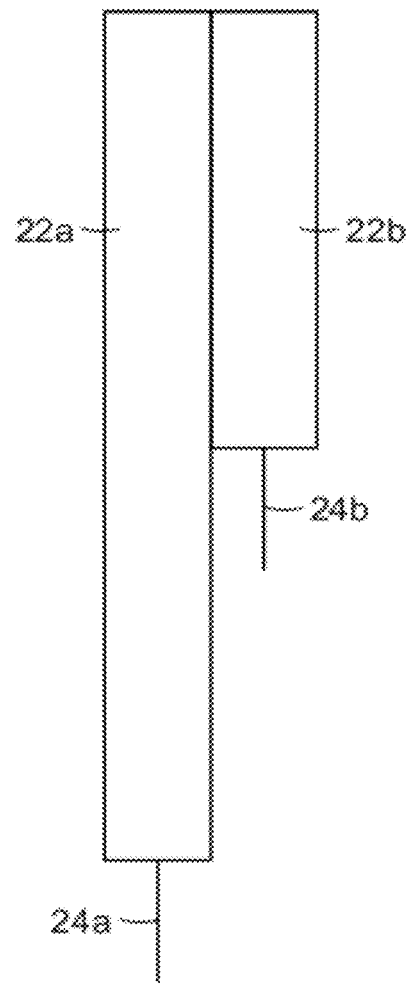
FIG. 2 illustrates a bipolar electrical ablation system according to certain embodiments described herein.

Referring to FIG. 2, in one embodiment, the electrical ablation device 20 may comprise a first flexible shaft 22a housing the first electrode 24a and a second flexible shaft 22b housing the second electrode 24b. The electrical ablation device 20 may comprise a first protective sleeve or sheath (not shown) disposed over at least one of the first flexible shaft 22a and second flexible shaft 22b. The electrical ablation device 20 may comprise a first protective sleeve or sheath (not shown) disposed over the first flexible shaft 22a and a second protective sleeve or sheath (not shown) disposed over the second flexible shaft 22b. The length of the first flexible shaft 22a may be different than the length of the second flexible shaft 22b. The length of the first flexible shaft 22a may be greater than or equal to the length of the second flexible shaft 22b. The length of the first protective sleeve or sheath may be different than the length of the second protective sleeve or sheath. The length of the first protective sleeve or sheath may be greater than or equal to the length of the second protective sleeve or sheath. In one embodiment, an electrical ablation device for biphasic pulses may have the first flexible shaft 22a disposed over the first electrode 24a having a positive polarity and the second flexible shaft 22b disposed over the second electrode 24b having a negative polarity, and wherein the length of the first flexible shaft 22a is greater than the length of the second flexible shaft 22b.

Figure 3:
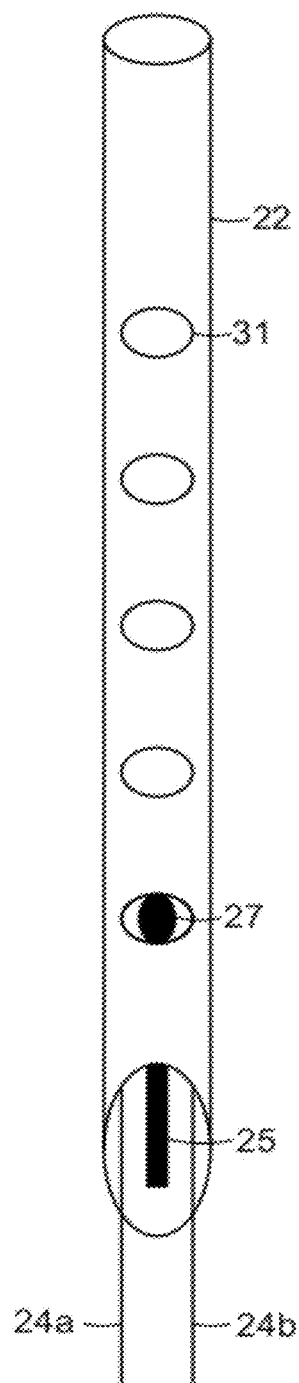
FIG. 3 illustrates an electrical ablation system including sensors according to certain embodiments described herein.
Figure 4:
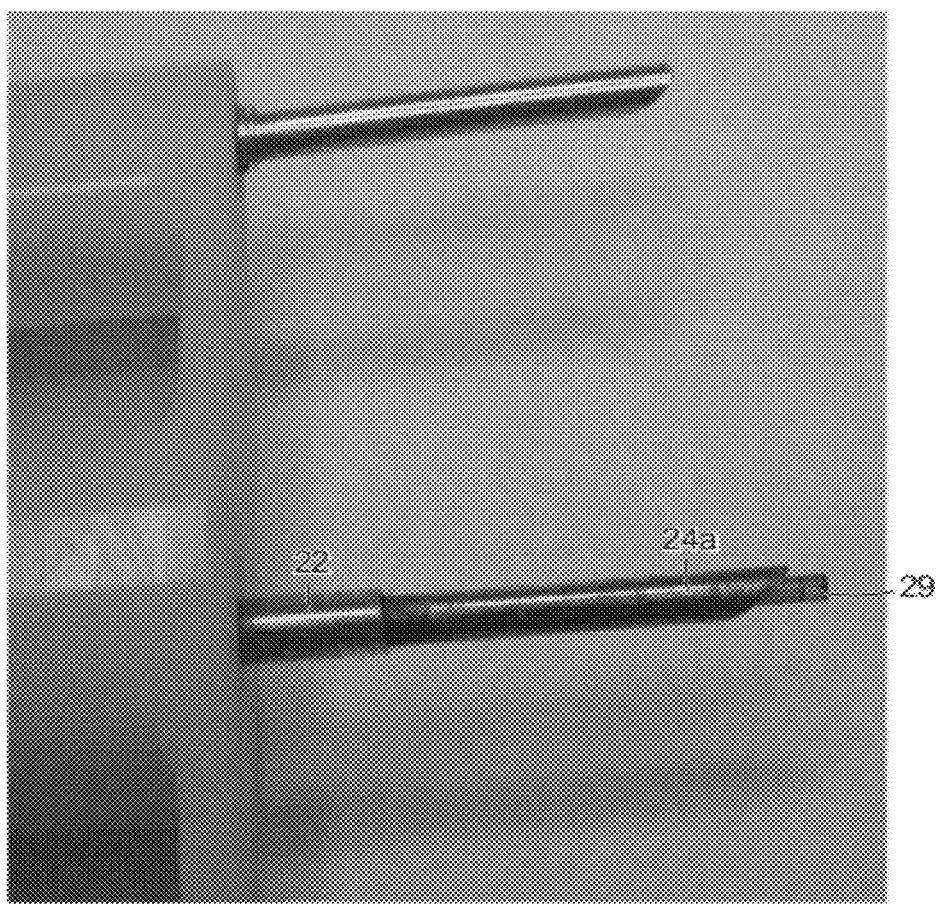
FIG. 4 illustrates an electrical ablation system including a temperature sensor according to certain embodiments described herein.

Referring to FIGS. 1 and 3, the electrical ablation device 20 may be configured to measure at least one of the temperature and pressure. The transducers or sensors 29 may comprise at least one of a temperature sensor and a pressure sensor. In certain embodiments, at least one of a temperature sensor and pressure sensor may be located in or proximate the electrical ablation system 10. The temperature sensor and/or pressure sensor may be located within the handle 28. The temperature sensor and/or pressure sensor may be located within the protective sleeve or sheath 26. The temperature sensor 25 and/or pressure sensor 27 may be located within the flexible shaft 22. The temperature sensor 25 and/or pressure sensor 27 may be located at the distal end of the flexible shaft 22. The protective sleeve or sheath 26 and/or the flexible shaft 22 may comprise one or more vents 31 configured for measuring at least one of the temperature and pressure of the tissue treatment region. The temperature sensor and/or pressure sensor may be located within the electrodes 24a,b. The pressure sensor 27 may be adjacent to at least one of the vents 31. In one embodiment, the pressure sensor 27 may be adjacent at least one of the vents 31 and the temperature sensor 25 may be located at the distal end of the flexible shaft 22. FIG. 4 is a photograph of an electrical ablation device comprising an optical temperature sensor 29 located in the electrode 24a at the distal end of the flexible shaft 22.

In certain embodiments, the temperature sensor and/or pressure sensor may be separate from the electrical ablation system 10. The electrical ablation device 20 may include the temperature sensor 25 and the pressure sensor may be separate from the electrical ablation system 10. The electrical ablation device 20 may include the pressure sensor 27 and the temperature sensor may be separate from the electrical ablation system 10.

According to certain embodiments, the temperature sensor may measure the temperature of the tissue treatment region. The temperature sensor may measure the temperature of the undesirable tissue. The temperature sensor may measure the temperature of the tissue surrounding the electrodes. The temperature sensor may measure the temperature before, during, and/or after treatment. The temperature sensor may measure the temperature before the first sequence of electrical pulses is delivered to the tissue. The temperature sensor may measure the temperature after the first sequence of electrical pulses is delivered to the tissue. The temperature sensor may measure the temperature before the second sequence of electrical pulses is delivered to the tissue. The temperature sensor may measure the temperature after the second sequence of electrical pulses is delivered to the tissue.

According to certain embodiments, the pressure sensor may measure the pressure of the tissue treatment region. The pressure sensor may measure the pressure of the space between the electrodes. The pressure sensor may measure the pressure surrounding the electrodes. The pressure sensor may measure the pressure before, during, and/or after treatment. The pressure sensor may measure the pressure before the first sequence of electrical pulses is delivered to the tissue. The pressure sensor may measure the pressure after the first sequence of electrical pulses is delivered to the tissue. The pressure sensor may measure the pressure before the second sequence of electrical pulses is delivered to the tissue. The pressure sensor may measure the pressure after the second sequence of electrical pulses is delivered to the tissue.

The temperature sensor and pressure sensor may provide feedback to the operator, surgeon, or clinician to apply an electric field pulse to the undesirable tissue. The pressure and/or temperature information may be useful to determine whether the undesirable tissue may be treated having reduced or no detrimental thermal effects to surrounding healthy tissue. The feedback information provided by the transducers or sensors 29 may be processed and displayed by circuits located either internally or externally to the energy source 14.

In one embodiment, the input to the energy source 14 may be connected to a commercial power supply by way of a plug (not shown). The output of the energy source 14 is coupled to the electrodes 24a,b, which may be energized using the activation switch 62 on the hand piece 16, or an activation switch mounted on a foot activated pedal (not shown). The energy source 14 may be configured to produce electrical energy suitable for thermal heating and/or electrical ablation.

In one embodiment, the electrodes 24a,b may be adapted and configured to electrically couple to the energy source 14 (e.g., generator, waveform generator). Once electrical energy is coupled to the electrodes 24a,b, an electric field may be formed at a distal end of the electrodes 24a,b. The energy source 14 may be configured to generate electric pulses at a predetermined frequency, amplitude, pulse width, and/or polarity that are suitable to induce thermal heating in the undesirable tissue in the treatment region. The energy source 14 may be configured to generate electric pulses at a predetermined frequency, amplitude, pulse width, and/or polarity that are suitable to induce irreversible electroporation to ablate substantial volumes of undesirable tissue in the treatment region. For example, the energy source 14 may be configured to deliver DC electric pulses having a predetermined frequency, amplitude, pulse width, and/or polarity suitable to induce thermal heating in the undesirable tissue in the treatment region. For example, the energy source 14 may be configured to deliver DC electric pulses having a predetermined frequency, amplitude, pulse width, and/or polarity suitable to induce irreversible electroporation to ablate substantial volumes of undesirable tissue in the treatment region. The DC pulses may be positive or negative relative to a particular reference polarity. The polarity of the DC pulses may be reversed or inverted from positive-to-negative or negative-to-positive a predetermined number of times to induce irreversible electroporation to ablate substantial volumes of undesirable tissue in the treatment region.

In one embodiment, a timing circuit may be coupled to the output of the energy source 14 to generate electric pulses. The timing circuit may comprise one or more suitable switching elements to produce the electric pulses. For example, the energy source 14 may produce a series of m electric pulses (where m is any positive integer) of sufficient amplitude and duration less than the necrotic threshold to induce thermal heating in the undesirable tissue when the m electric pulses are applied to the electrodes 24a,b and a series of n electric pulses (where n is any positive integer) of sufficient amplitude and duration to induce irreversible electroporation suitable for tissue ablation when the n electric pulses are applied to the electrodes 24a,b. In one embodiment, the electric pulses may have a fixed or variable pulse width, amplitude, and/or frequency.

Figure 5A:
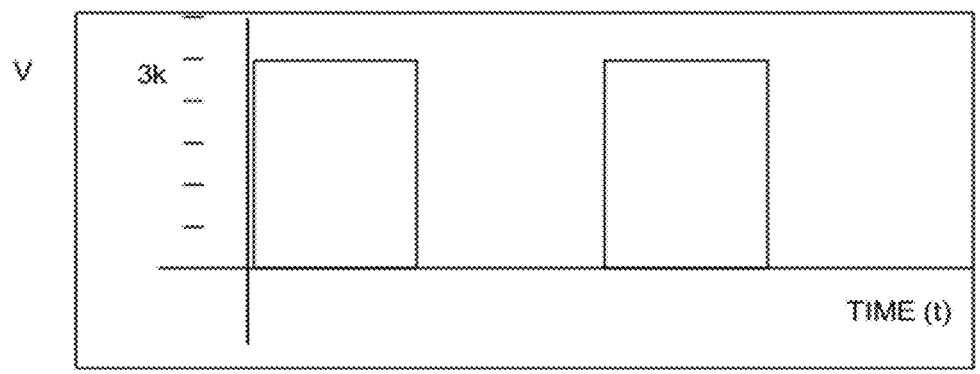
FIG. 5A is a graphical representation of a series of monophasic electrical pulses that may be applied to undesirable tissue.
Figure 6A:
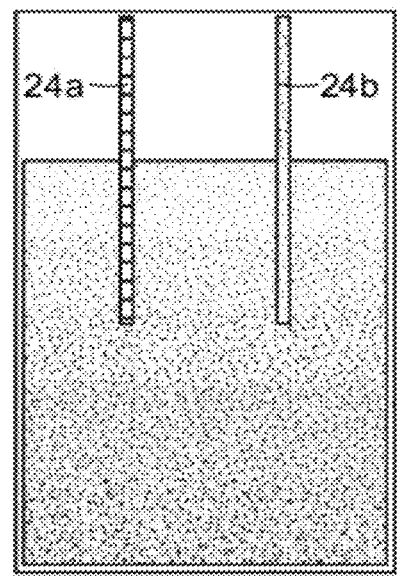
FIG. 6A illustrates two electrodes in a monophasic electrical ablation system according to certain embodiments described herein.

The electrical ablation device 20 may be operated either in bipolar mode, i.e., monophasic, or monopolar mode, i.e., biphasic. In monopolar mode, the surface area of the electrodes may be different, and a dispersive pad (i.e., a ground pad) may be positioned relatively far from the "active" electrode. In bipolar mode, the surface area of the electrodes may be similar, and electrodes may be positioned relatively close together. FIG. 5A is a graphical representation of a series of monophasic electrical pulses having the same polarity in which each pulse has an amplitude of +3,000 VDC. In other words, the polarity may not change between the electrodes for monophasic electrical pulses. FIG. 6A illustrates two electrodes 24a,b in a monophasic electrical ablation system in which the first electrode 24a has a positive polarity relative to the other electrode 24b. A ground pad may be substituted for one of the electrodes.

Figure 5B:
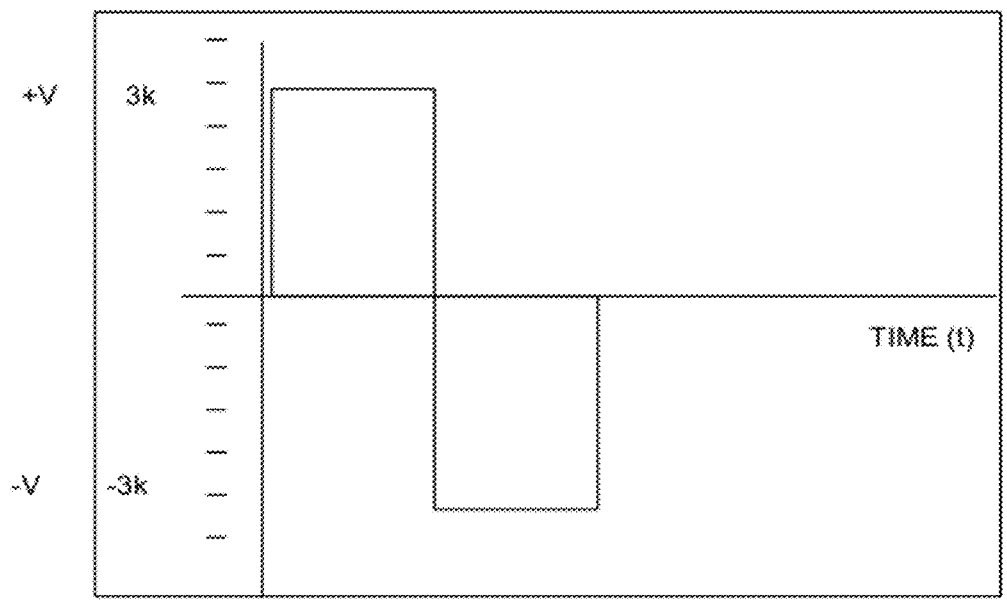
FIG. 5B is a graphical representation of a series of biphasic electrical pulses that may be applied to undesirable tissue.
Figure 6B:
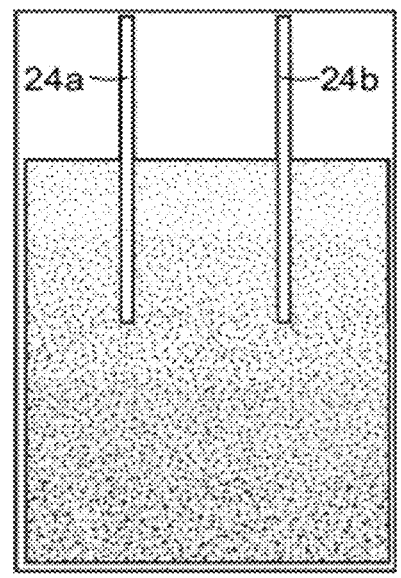
FIG. 6B illustrates two electrodes in a biphasic electrical ablation system according to certain embodiments described herein.

FIG. 5B is a graphical representation of a series of biphasic electrical pulses having opposite polarity in which the first electrical pulse has an amplitude of +3,000 VDC and the second electrical pulse has an amplitude of −3,000 VDC. FIG. 6B illustrates two electrodes 24a,b in a bipolar electrical ablation system in which the polarity of each electrodes 24a,b alternates. In bipolar mode, the first electrode 24a may be electrically connected to a first polarity and the second electrode 24b may be electrically connected to the opposite polarity. In monophasic mode, the first electrode 24a may be coupled to a prescribed voltage and the second electrode 24b may be set to ground. The energy source 14 may be configured to operate in either the biphasic or monophasic modes with the electrical ablation system 10. In biphasic mode, the first electrode 24a may be electrically connected to a prescribed voltage of one polarity and the second electrode 24b may be electrically connected to a prescribed voltage of the opposite polarity. The polarity may alternate between the electrodes for biphasic electrical pulses. When more than two electrodes are used, the polarity of the electrodes may be alternated so that any two adjacent electrodes may have either the same or opposite polarities. In bipolar mode, the negative electrode of the energy source 14 may be coupled to an impedance simulation circuit. According to certain embodiments, a monophasic output or a biphasic output may be applied to a monopolar electrode orientation or a bipolar electrode orientation.

In one embodiment, the energy source 14 may be configured to produce RF waveforms at predetermined frequencies, amplitudes, pulse widths, and/or polarities suitable for thermal heating and/or electrical ablation of cells in the tissue treatment region. One example of a suitable RF energy source may be a commercially available conventional, bipolar/monopolar electrosurgical RF generator, such as Model Number ICC 350, available from Erbe, GmbH. In one embodiment, the energy source may comprise a microwave energy source configured to produce microwave waveforms at predetermined frequencies, amplitudes, pulse widths, and/or polarities suitable for thermal heating and/or electrical ablation of cells in the tissue treatment region. The microwave power source, such as MicroThermx, available from Boston Scientific Corp., may be coupled to a microwave antenna providing microwave energy in the frequency range from 915 MHz to 2.45 GHz.

In one embodiment, the energy source 14 may be configured to produce destabilizing electrical potentials (e.g., fields) suitable to induce thermal heating and/or irreversible electroporation. The destabilizing electrical potentials may be in the form of biphasic/monophasic DC electric pulses suitable for inducing thermal heating and/or irreversible electroporation to ablate tissue undesirable tissue with the electrical ablation device 20. A commercially available energy source suitable for generating thermal heating and/or irreversible electroporation electric field pulses in bipolar or monopolar mode is a pulsed DC generator such as Model Number ECM 830, available from BTX Molecular Delivery Systems Boston, Mass. In bipolar mode, the first electrode 24a may be electrically coupled to a first polarity and the second electrode 25 may be electrically coupled to a second (e.g., opposite) polarity of the energy source 14. Biphasic/monophasic electric pulses may be generated at a variety of frequencies, amplitudes, pulse widths, and/or polarities. Unlike RF ablation systems, which may require high power and energy levels delivered into the tissue to heat and thermally destroy the tissue, irreversible electroporation may require very little energy applied to the tissue to heat and kill the cells of the undesirable tissue using electric field potentials rather than heat. Accordingly, irreversible electroporation systems may avoid the detrimental thermal effects caused by RF ablation systems.

In certain embodiments, the energy source may comprise a wireless transmitter to deliver energy to the electrodes using wireless energy transfer techniques via one or more remotely positioned antennas. Those skilled in the art will appreciate that wireless energy transfer or wireless power transmission refers to the process of transmitting electrical energy from an energy source to an electrical load without interconnecting wires. In one embodiment, the energy source 14 may be coupled to the first and second electrodes 24a,b by a wired or a wireless connection. In a wired connection, the energy source 14 may be coupled to the electrodes 24a,b by way of the electrical conductors 18a,b, as shown. In a wireless connection, the electrical conductors 18a,b may be replaced with a first antenna (not shown) coupled the energy source 14 and a second antenna (not shown) coupled to the electrodes 24a,b, wherein the second antenna may be remotely located from the first antenna. In one embodiment, the energy source may comprise a wireless transmitter to deliver energy to the electrodes using wireless energy transfer techniques via one or more remotely positioned antennas. As previously discussed, wireless energy transfer or wireless power transmission is the process of transmitting electrical energy from the energy source 14 to an electrical load, e.g., the abnormal cells in the tissue treatment region, without using the interconnecting electrical conductors 18a,b. An electrical transformer is the simplest example of wireless energy transfer. The primary and secondary circuits of a transformer may not be directly connected and the transfer of energy may take place by electromagnetic coupling through a process known as mutual induction. Power also may be transferred wirelessly using RF energy.

In one embodiment, the energy source 14 may be configured to generate DC electric pulses at frequencies in the range of about 1 Hz to about 10,000 Hz, amplitudes in the range of about ±100 VDC to about ±6,000 VDC, and pulse width in the range of about 1 μs to about 100 ms. The polarity of the electric potentials coupled to the electrodes 24a,b may be reversed during thermal heating and/or electrical ablation therapy. For example, initially, the electric pulses may have a positive polarity and an amplitude in the range of about +100 VDC to about +6,000 VDC. Subsequently, the polarity of the DC electric pulses may be reversed such that the amplitude is in the range of about −100 VDC to about −6,000 VDC. In one embodiment, the undesirable cells in the tissue treatment region may be electrically ablated with DC pulses suitable to induce irreversible electroporation at frequencies of about 10 Hz to about 100 Hz, amplitudes in the range of about +700 VDC to about +3,000 VDC, and pulse widths of about 10 μs to about 50 μs. In another embodiment, the abnormal cells in the tissue treatment region may be electrically ablated with an electrical waveform having an amplitude of about +500 VDC and pulse duration of about 20 μs delivered at a pulse period T or repetition rate, frequency $f=1/T$, of about 10 Hz. Without wishing to be bound to any particular theory, it is believed that an electric field strength of about 800 V/cm to 1,000 V/cm is suitable for destroying living tissue by inducing irreversible electroporation.

The electrodes 24a,b may have a diameter or radius from 0.5 mm to 1.5 mm, such as, for example, 0.5 mm, 0.75 mm, 1 mm, and 1.5 mm. In various embodiments, the diameter of the first electrode 24a may by different from the diameter of the second electrode 24b. The electrode spacing may be from 0.5 cm to 3 cm. In various embodiments, the distance from the first electrode 24a to the second electrode 24b may be from 0.5 cm to 3 cm, such as, for example, 1 cm, 1.5 cm, 2.0 cm, and 3 cm. In one embodiment, the electrical ablation device 20 may comprise multiple needle electrodes.

According to certain embodiments, the electrical ablation device 20 may be introduced into the tissue treatment region through a trocar, for example, or inserted to a tissue treatment region transcutaneously, percutaneously, or other suitable techniques. In one embodiment, the cannula, lumen, or channel defined within the flexible shaft 22 may comprise a cutting edge, such as a bevel or other sharp edge, to aid in the puncturing/piercing of tissue.

According to certain embodiments, a method of treating tissue may generally comprise obtaining an ablation apparatus comprising first and second electrodes coupled to an energy source operative to generate and deliver a first sequence of electrical pulses and a second sequence of electrical pulses to tissue having a necrotic threshold, wherein the first sequence of electrical pulses deliver a first energy dose that is less than the necrotic threshold to induce thermal heating in the tissue and the second sequence of electrical pulses deliver a second energy dose equal to or greater than the necrotic threshold to induce cell necrosis in the tissue by irreversible electroporation, inserting the first electrode into a mass of tissue having a necrotic threshold, applying a first sequence of electrical pulses to the first electrode less than the necrotic threshold to induce thermal heating, applying a second sequence of electrical pulses to the first electrode to induce cell necrosis by irreversible electroporation, and applying a ground potential to the second electrode, wherein the ablation apparatus is operative to reduce the necrotic threshold of the tissue relative to a corresponding ablation apparatus having an energy source configured to deliver a first sequence of electrical pulses to induce cell necrosis by irreversible electroporation.

In certain embodiments, the ablation apparatus may reduce the necrotic threshold of the cell membrane by 0-500 mV, such as, for example, 50-400 mV, 100-300 mV, and 150-250 mV relative to a corresponding ablation apparatus having an energy source configured to deliver a first sequence of electrical pulses to induce cell necrosis by irreversible electroporation. The ablation apparatus may reduce the necrotic threshold by 0-50%, such as, for example, 10%, 20%, 30%, and 40%, relative to a corresponding ablation apparatus having an energy source configured to deliver a first sequence of electrical pulses to induce cell necrosis by irreversible electroporation.

According to certain embodiments, a method of treating tissue may generally comprise applying a first sequence of electrical pulses to undesirable tissue to induce thermal heating and applying a second sequence of electrical pulses to undesirable tissue to induce cell necrosis by irreversible electroporation. The first energy dose may be less than the necrotic threshold, less than the critical membrane voltage, less than the threshold for muscle contraction, and/or less than the threshold for ventricular arrhythmia. The first energy dose may reduce the necrotic threshold of the tissue. The first energy dose may reduce the necrotic threshold of the cell membrane by 0-500 mV, such as, for example, 50-400 mV, 100-300 mV, and 150-250 mV. The first energy dose may reduce the necrotic threshold by 0-50%, such as, for example, 10%, 20%, 30%, and 40%. The first energy dose and/or second energy dose may be synchronized with the patient's cardiac cycle to prevent ventricular arrhythmia. According to certain embodiments, the ablation apparatus may reduce the risk of ventricular arrhythmia relative to a similar ablation apparatus comprising a first sequence of electrical pulses to induce cell necrosis in the tissue by irreversible electroporation.

In certain embodiments, a method of treating tissue may generally comprise inserting the first electrode into a mass of tissue having a membrane potential and a necrotic threshold, applying a first sequence of electrical pulses to the first electrode less than the necrotic threshold to induce thermal heating, applying a second sequence of electrical pulses to the first electrode to induce cell necrosis by irreversible electroporation, and applying a ground potential to the second electrode. In one embodiment, the method may comprise re-applying the sequence of electrical pulses to the first electrode. In one embodiment, the energy source may be operative to generate and deliver a sequence interval between the first sequence and second sequence. The first sequence of electrical pulses may comprise a series of first pulse trains each having a first pulse train amplitude, a first pulse train pulse width, and a first pulse train frequency, and the second sequence of electrical pulses may comprise a series of second pulse trains each comprising a second pulse train amplitude, a second pulse train pulse width, and a second pulse train frequency. The first pulse trains may comprise a plurality of first pulses each having a first amplitude, a first pulse width, and a first frequency, and each of the second pulse trains may comprise a plurality of second pulses each having a second amplitude, a second pulse width, and a second frequency. Each of the first pulses and the second pulses may independently have amplitudes in the range of about ±100 VDC to about ±10,000 VDC, pulse widths in the range of about 1 μs to about 100 ms, and frequencies in the range of about 1 Hz to about 10,000 Hz.

Figure 7:
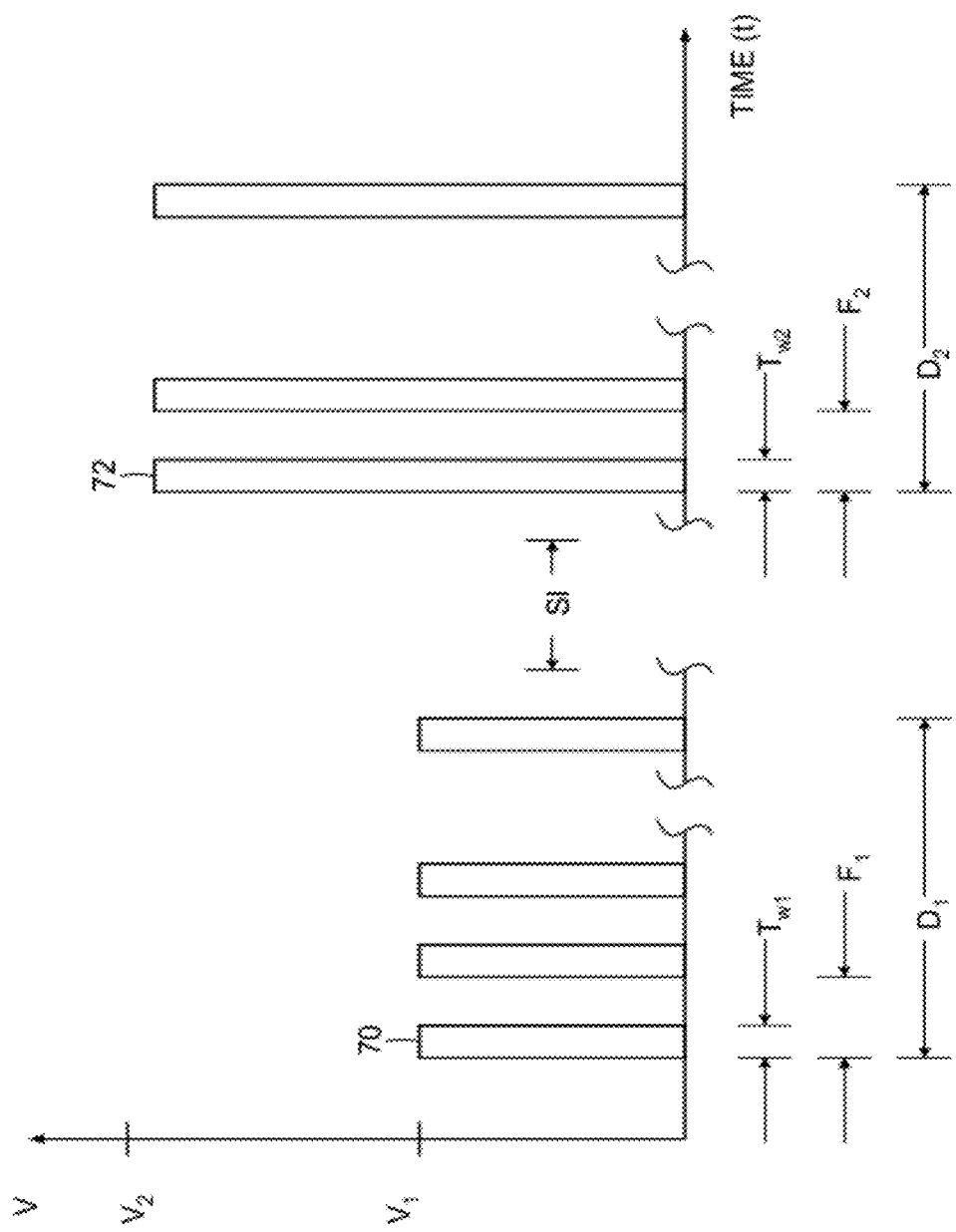
FIG. 7 is a graphical representation of a series of electrical pulses that may be applied to undesirable tissue to induce irreversible electroporation according to certain embodiments described herein.

FIG. 7 is a graphical representation of a first sequence of electrical pulses that deliver a first energy dose less than the necrotic threshold to induce thermal heating and a second sequence of electrical pulses that deliver a second energy dose to induce cell necrosis by irreversible electroporation. Time (t) is shown along the horizontal axis and voltage (VDC) is shown along the vertical axis. Initially, the undesirable tissue may be exposed to a series of first pulse trains 70 each having a first pulse train amplitude $V_1$, a first pulse train pulse width $T_{w1}$, and a first pulse train frequency $F_1$ sufficient to induce thermal heating in the tissue. When the tissue achieves a predetermined temperature and/or pressure, the undesirable tissue 48 may be exposed to a series of second pulse trains 72. The undesirable tissue may be exposed to a series of second pulse trains 72 each having a second pulse train amplitude $V_2$, a second pulse train pulse width $T_{w2}$, and a second pulse train frequency $F_2$ sufficient to induce thermal necrosis and/or irreversible electroporation in the tissue. The series of first pulse trains 70 may comprise at least one first pulse train and the series of second pulse trains 72 may comprise at least one second pulse train.

In certain embodiments, at least one of the first pulse train amplitude $V_1$, the first pulse train pulse width $T_{w1}$, and the first pulse train frequency $F_1$ may be greater than or equal to the second pulse train amplitude $V_2$, the second pulse train pulse width $T_{w2}$, and the second pulse train frequency $F_2$. The first pulse train amplitude $V_1$ may be less than or equal to the second pulse train amplitude $V_2$. The first pulse train pulse width $T_{w1}$ may be less than, greater than, or equal to the second pulse train pulse width $T_{w2}$. The first pulse train frequency $F_1$ may be greater than or equal to the second pulse train frequency $F_2$. The first sequence duration $D_1$ may be greater than or equal to the second sequence duration $D_2$. The total number of first pulse trains may be 70 may be greater than or equal to the total number of second pulse trains 72. In one embodiment, the first pulse train amplitude may be less than the second pulse train amplitude, the first pulse train pulse width may be equal to the second pulse train pulse width, and the first pulse train frequency may be greater than the second pulse train frequency. The energy source may operative to generate and deliver a sequence interval $S_I$ between the first sequence and second sequence. The sequence interval may be from 0 to 10 seconds, 1 second to 10 seconds, such as, for example, 0.5 seconds, 1 second, and 2 seconds.

FIGS. 8A-B are graphical representations of a first pulse train 70 and a second pulse train 72, respectively. Time (t) is shown along the horizontal axis and voltage (VDC) is shown along the vertical axis. Each of the first pulse trains 70 may comprise a plurality of first pulses 70a each having a first amplitude $v_1$, a first pulse width $t_{w1}$, and a first frequency $f_1$, and each of the second pulse trains 72 may comprise a plurality of second pulses 72a each having a second amplitude $v_2$, a second pulse width $t_{w2}$, and a second frequency $f_2$. The first pulses and the second pulses may be each independently characterized by first and second amplitudes in the range of about ±100 VDC to about ±10,000 VDC, first and second pulse widths in the range of about 1 μs to about 100 ms, and first and second frequencies in the range of about 1 Hz to about 10,000 Hz. In one embodiment, the energy source 14 may be configured to generate and deliver DC first pulses and the second pulses at frequencies in the range of 1 Hz to 10,000 Hz, amplitudes in the range of ±100 VDC to ±3000 VDC, and pulse width in the range of about 1 μs to about 100 ms. The first amplitude $v_1$ may be less than or equal to the second amplitude $v_2$. The first pulse width $t_{w1}$ may be less than, greater than, or equal to the second pulse width $t_{w2}$. The first frequency $f_1$ may be greater than or equal to the second frequency $f_2$. The total number of first pulses may be greater than or equal to the total number of second pulses. In one embodiment, the first amplitude may be less than the second amplitude, the first pulse width may be equal to the second pulse width, and the first frequency may be equal to the second frequency.

In one embodiment, a first pulse train 70 comprising high-voltage DC electrical pulses having a first pulse train amplitude $V_1$ of 500 VDC and a first pulse train pulse width $T_{w1}$ of 50 μs may be applied to the first and second electrodes 24a,b by the energy source 14 to induce thermal heating in the tissue. A second pulse train 72 comprising higher high-voltage DC electrical pulses having a second pulse train amplitude $V_2$ of 1000 V and a second pulse train pulse width $T_{w2}$ of 50 μs may be applied to the first and second electrodes 24a,b by the energy source 14 to induce cell necrosis in the tissue by irreversible electroporation. In one embodiment, the polarity of at least one of the first pulse train 70 and the second pulse train 72 may be inverted or reversed by the energy source 14 during the thermal heating and/or ablation processes.

In one embodiment, the series of first pulses 70 may comprises a single pulse 70a or multiple pulses having a first amplitude $v_1$ of 500 VDC, a first pulse width $t_{w1}$ of 10 μs to 15 μs, and a period $t_1$ of about 100 ms ($f_1$=10 Hz) sufficient to induce thermal heating in the tissue proximate the electrode-tissue-interface immediately surrounding the respective electrodes 24a,b. In one embodiment, the series of second pulses 72 may comprise 20 to 40 electric pulses 72a having a second amplitude $v_2$ of 1000 VDC, a second pulse width $t_{w2}$ of 10 μs to 15 μs, and a period $t_2$ of 100 μs ($f_2$=10,000 Hz) sufficient to induce irreversible electroporation. In one embodiment, the series of second pulses 72 may comprise multiple electrical pulses, for example, 20 to 40 electric pulses, having a second amplitude $v_2$ of 1500 to 3000 VDC, a second pulse width $t_{w2}$ of 10 μs to 50 μs, and a period $t_2$ of 10 μs. In one embodiment, the undesirable cells in the tissue treatment region may be electrically ablated with DC pulses suitable to induce irreversible electroporation at frequencies of about 10 Hz to about 100 Hz, amplitudes in the range of about +700 VDC to about +1500 VDC, and pulse widths of about 10 μs to about 50 μs. In another embodiment, the abnormal cells in the tissue treatment region may be heated with an electrical waveform having an amplitude of about +500 VDC and pulse duration of about 20 ms delivered at a pulse period or repetition rate, frequency f=1/T, of about 10 Hz.

In certain embodiments, a total dose average power may comprise the average power of the first sequence of electrical pulses, the average power of the second sequence of electrical pulses, and the sequence interval. The first energy dose may have an average power from 5 Watts to 10 Watts. The second first energy dose may have an average power from 10 Watts to 15 Watts. The total dose average power may be 1 Watt to 5 Watts. In one embodiment, a total dose average power from 5 Watts to 10 Watts may cause thermal coagulation. The first and second sequences of electrical pulses may be configured to reduce or eliminate thermal coagulation at the electrode/tissue interface.

In certain embodiments, the polarity of the electric potentials coupled to the electrodes 24a,b may be reversed during the electrical ablation therapy. As shown in FIG. 9, the series of first pulse trains 70 may comprise multiple biphasic pulse trains each having a positive first pulse train amplitude $+V_1$ or a negative first pulse train amplitude $-V_1$, a first pulse train pulse width $T_{w1}$, and a first pulse train frequency $F_1$, and the series of second pulse trains 72 may comprise multiple biphasic pulse trains each having a positive second pulse train amplitude $+V_2$ or a negative second pulse train amplitude $-V_2$, a second pulse train pulse width $T_{w2}$, and a second pulse train frequency $F_2$. The first pulses and the second pulses may be each independently characterized by first and second amplitudes in the range of about ±100 VDC to about ±10,000 VDC, first and second pulse widths in the range of about 1 μs to about 100 ms, and first and second frequencies in the range of about 1 Hz to about 10,000 Hz. In one embodiment, the first sequence of electrical pulses and the second sequence of electrical pulses may comprise biphasic pulses. In one embodiment, the first sequence of electrical pulses may comprise biphasic pulses and the second sequence of electrical pulses may not comprise biphasic pulses. In one embodiment, the first sequence of electrical pulses may not comprise biphasic pulses and the second sequence of electrical pulses may comprise biphasic pulses.

As shown in FIGS. 10A-B, each of the first pulse trains may comprise a plurality of first pulses 70a each having a positive first amplitude $+v_1$ or a negative first amplitude $-v_1$, a first pulse width $t_{w1}$, and a first frequency $f_1$, and each of the second pulse trains comprises a plurality of second pulses 72a each having a positive second amplitude $+v_2$ or a negative second amplitude $-v_2$, a second pulse width $t_{w2}$, and a second frequency $f_2$. In one embodiment, the first sequence of electrical pulses and the second sequence of electrical pulses may comprise biphasic pulses. In one embodiment, the plurality of first pulses may comprise biphasic pulses and the plurality of second pulses may not comprise biphasic pulses. In one embodiment, the plurality of first pulses may not comprise biphasic pulses and the plurality of second pulses may comprise biphasic pulses.

In one embodiment, the energy source 14 may be configured to generate and deliver DC first pulses and the second pulses at frequencies in the range of 1 Hz to 10,000 Hz, amplitudes in the range of ±100 VDC to ±3000 VDC, and pulse width in the range of about 1 μs to about 100 ms. In one embodiment, the first pulse trains may comprise a plurality of DC first pulses having a positive polarity and an amplitude in the range of about +100 VDC to about +6000 VDC and a negative polarity and an amplitude in the range of about −100 VDC to about −6000 VDC, the second pulse trains may comprise a plurality of second pulses having a positive polarity and an amplitude in the range of about +100 VDC to about +6000 VDC and a negative polarity and an amplitude in the range of about −100 VDC to about −6000 VDC. In one embodiment, the method may comprise applying a sequence of electrical pulses having a first polarity to induce cell thermal heating and applying a sequence of electrical pulses having an opposite polarity to induce cell necrosis by irreversible electroporation.

Without wishing to be bound to any particular theory, it is believed that biphasic pulses may reduce the skeletal muscle contractions by reducing or eliminating the action potential caused by a positive monophasic pulse. Biphasic pulses may reduce or eliminate skeletal muscle contractions and cardiac events. A person skilled in the art will understand that poration of the cell membrane occurs when the pulse increases the membrane voltage. A person skilled in the art may expect the poration to be reversed by a negative going pulse. Without wishing to be bound to any particular theory, however, it is believed that hyperpolarization occurs on each side of the cell. For example, the opposite side of the cell membrane may be hyperpolarized when the electric field switches orientation due to a negative-going pulse. In other words, the polarization of the cell may be dependent on the orientation of the electric field.

According to certain embodiments, the method of treating tissue may comprise heating the tissue by applying an electric field that is less than the necrotic threshold to lower the necrotic threshold before inducing cell necrosis. The method may comprise lowering the necrotic threshold by heating the tissue by applying an electric field that is less than about 700 V/cm, such as, for example, less than about 500 V/cm and less than about 300 V/cm. The method may comprise lowering the necrotic threshold by 30% by heating the tissue by applying an electric field that is less than about 700 V/cm. The method may comprise heating the tissue by applying an electric field that is less than the necrotic threshold to lower the necrotic threshold and inducing cell necrosis by irreversible electroporation by applying an electric filed that is greater than or equal to the necrotic threshold. The method may comprise heating the tissue by applying an electric field that is less than 700 V/cm to lower the necrotic threshold and inducing cell necrosis by irreversible electroporation by applying an electric filed that is greater than about 700 V/cm.

According to certain embodiment, the method of treating tissue may comprise applying a sequence of electrical pulses to increase a membrane potential to less than the necrotic threshold and applying a sequence of electrical pulses to increase a membrane potential to greater than or equal to the necrotic threshold. The method may comprise applying a sequence of electrical pulses to increase a membrane potential from less than zero to greater than zero, applying a sequence of electrical pulses to increase a membrane potential from greater than zero to less than the necrotic threshold, and applying a sequence of electrical pulses to increase a membrane potential from less than the necrotic threshold to the necrotic threshold. The method may comprise applying a sequence of electrical pulses to increase a membrane potential from less than zero to 100 mV, applying a sequence of electrical pulses to increase a membrane potential from 100 mV to 500 mV, and applying a sequence of electrical pulses to increase a membrane potential from 500 mV to the necrotic threshold.

In one embodiment, the first sequence of electrical pulses may have a pulse width of 50 µm or less and subsequent pulses may have higher voltages and pulse widths less than 50 µm. The pulses may increase the membrane potential from −70 mV to +100 mV, the next sequence of pulses may increase the membrane potential from 100 mV to 500 mV, and the final sequence of pulses may have pulse width of 1 µs to increase the membrane potential to cause cell necrosis. Without wishing to be bound to any particular theory, it is believed that the synergistic effect of applying the first sequence of pulses to induce thermal heating and applying the second sequence of pulses to induce cell necrosis by irreversible electroporation may decrease the membrane threshold from 1 V to 0.7 V.

According to certain embodiments, the method may comprise forming a pre-heated zone in the undesirable tissue by applying an electric field that is less than the necrotic threshold. The method may comprise forming a pre-heated zone in the undesirable tissue by applying an electric field that is less than the necrotic threshold and forming a necrotic zone by applying an electric field that is equal to or greater than the necrotic threshold to induce cell necrosis by irreversible electroporation. The method may comprise forming a pre-heated zone by applying an electric field that is less than about 700 V/cm and forming a necrotic zone by applying an electric filed that is equal to or greater than about 700 V/cm.

FIG. 11 is a graphical representation of a series of electrical pulses that may be applied to undesirable tissue. FIG. 11 illustrates the relationship between the pulse parameters and electrode temperature and the size and proportion of the necrotic zone. As shown in FIG. 11, the size and proportion of the necrotic zone may generally increase as the voltage and/or temperature increases. The size and proportion of the necrotic zone and thermal zone may be related to the pulse parameters, such as, for example, energy, peak power, and average power, and electrode spacing. The contribution of voltage and temperature to the size and proportion of the necrotic zone and thermal zone may be related to the peak pulsed power and average power.

In one embodiment, a pre-heated thermal zone may be formed in the tissue immediately surrounding the electrodes 24a,b at the tissue-electrode-interface by applying an electric field less than the necrotic threshold. Without wishing to be bound to any particular theory, it is believed that increasing the temperature of the tissue may reduce the electric field necessary to cause cell necrosis in the undesirable tissue 48.

Thus, the method of treating tissue may comprise applying a combination of a series of first electrical pulses 70 having substantially lower voltage (in the range of 1000 V to 2000 V) and a series of second electrical pulses 72 having a higher voltage to induce cell necrosis. In one embodiment, a first series of pulses 70 may be applied to create a pre-heated thermal zone to increase the temperature of the tissue and then a second series of pulses 72 to induce cell necrosis at a lower voltage then otherwise would be necessary without the thermal heating of the tissue before inducing irreversible electroporation. In one embodiment, the method of treating tissue may comprise applying a combination of a series of first electrical pulses 70 having substantially lower voltage to increase the size of the pre-heated thermal zone at the same voltage.

Once positioned by the user, the electrodes may be energized to form a pre-heated zone having a first shape in the tissue treatment region. The shape of the pre-heated zone may be dependent on the position of the first and second electrodes. When the electrodes are re-energized, a necrotic zone having a second shape may be formed in the tissue treatment region. The size of the pre-heated zone may be less than or equal to the size of the necrotic zone. This process may be repeated as often as necessary to create any number of necrotic zones using the electrical ablation apparatus. Various parameters, such as, for example, pressure, temperature, and duration, may be altered or adjusted according to the type of tissue in the tissue treatment region and the desired size of the pre-heated zone and/or necrotic zone. In one embodiment, the ablation apparatus may increase the size of the necrotic zone relative to a similar ablation apparatus comprising a first sequence of electrical pulses to induce cell necrosis in the tissue by irreversible electroporation. At anytime, the surgeon or clinician may reposition the electrical ablation apparatus within the tissue treatment region and begin the process anew.

According to certain embodiments, the method of treating tissue may comprise applying a first sequence of electrical pulses to induce thermal heating and applying a second sequence of electrical pulses to induce cell necrosis by irreversible electroporation, wherein the first and second sequences of electrical pulses create a ratio of thermal volume to non-thermal volume of 5 to 1. The thermal volume may comprise the volume of the pre-heated zone. In one embodiment, at least one of the first sequence of electrical pulses, the second sequence of electrical pulses, and sequence interval may be configured to create a ratio of thermal volume to non-thermal volume of 2 to 1. In one embodiment, at least one of the first sequence of electrical pulses, the second sequence of electrical pulses, and sequence interval may be configured to create a ratio of thermal zone volume to necrotic zone volume of 1 to 1.

According to certain embodiments, the method may comprise measuring at least one of temperature and pressure of the tissue treatment region. The method may comprise measuring at least one of temperature and pressure of the undesirable tissue. The method may comprise measuring at least one of temperature and pressure adjacent at least one of the first and second electrodes. The method may comprise measuring at least one of temperature and pressure adjacent at least one of the first and second electrodes and applying a sequence of electrical pulses when at least one of a predetermined temperature and a predetermined pressure is achieved. The method may comprise measuring at least one of temperature and pressure adjacent at least one of the first and second electrodes and stopping a sequence of electrical pulses when at least one of a predetermined temperature and a predetermined pressure is achieved. The method may comprise measuring at least one of temperature and pressure adjacent at least one of the first and second electrodes and applying a sequence of electrical pulses to achieve at least one of a predetermined temperature and a predetermined pressure.

Without wishing to be bound to any particular theory, it is believed that the critical membrane voltage of a cell is inversely proportional to the cell's temperature. In other words, the cell's critical membrane voltage may decrease as the cell's temperature increases. As a result, a lower electric field may be applied to pre-heated undesirable tissue to induce cell necrosis by irreversible electroporation than to the same undesirable tissue without pre-heating. The predetermined temperature may be 40° C. to 50° C. For example, an electrical pulse or sequence of electrical pulses may be applied when the temperature of the tissue falls below 50° C. The method may comprise stopping a sequence of electrical pulses when at least one of a predetermined temperature and a predetermined pressure is achieved. For example, an electrical pulse or sequence of electrical pulses may be stopped when the temperature of the tissue reaches 60° C. In one embodiment, the first and second sequences of electrical pulses may be configured to maintain the tissue at a temperature sufficient to induce thermal coagulation. For example, the first and second sequences of electrical pulses may be configured to maintain the tissue at a temperature between 50-60° C. The predetermined pressure may be atmospheric pressure.

According to certain embodiments, the ablation apparatus may reduce the risk of an electrical arc relative to a similar ablation apparatus comprising a first sequence of electrical pulses to induce cell necrosis in the tissue by irreversible electroporation. Under certain conditions, an arc may form between the two electrodes. For example, high voltage may cause a breakdown in air in the space between the un-insulated conductive portions of the electrodes that are not fully embedded in the tissue. An electrical arc at high voltages (>10 kVDC) may occur when the un-insulated conductive portions of the two electrodes are not fully embedded into the tissue or the tissue moves away from the electrode tip and the high voltage causes an electrical breakdown of the gas surrounding the electrode tip. The first and second sequences of electrical pulses may be configured to reduce or eliminate the creation of an arc. As described in commonly owned U.S. patent application Ser. No. 12/651,181, a gel may be continuously supplied to the space to displace the air in the space and prevent an arc from forming. The gel may be any water-based, water-soluble lubricant, such as, for example, KY® Jelly available from Johnson & Johnson.

FIG. 12 illustrates one embodiment of the electrical ablation system 10 shown in FIG. 1 in use to treat undesirable tissue 48 located on the surface of the liver 50. The undesirable tissue 48 may be representative of diseased tissue, cancer, malignant and benign tumors, masses, lesions, and other abnormal tissue growths. In use, the electrical ablation device 20 may be introduced into or proximate the tissue treatment region through a port 52 of a trocar 54. The trocar 54 may be introduced into the patient via a small incision 59 formed in the skin 56. The endoscope 12 may be introduced into the patient trans-anally through the colon, trans-orally down the esophagus and through the stomach using translumenal techniques, or through a small incision or keyhole formed through the patient's abdominal wall (e.g., the peritoneal wall). The endoscope 12 may be employed to guide and locate the distal end of the electrical ablation device 20 into or proximate the undesirable tissue 48. Prior to introducing the flexible shaft 22 through the trocar 54, the sheath 26 may be slid over the flexible shaft 22 in a direction toward the distal end thereof to cover the electrodes 24a,b until the distal end of the electrical ablation device 20 reaches the undesirable tissue 48.

Once the electrical ablation device 20 has been suitably introduced into or proximate the undesirable tissue 48, the sheath 26 may be retracted to expose the electrodes 24a,b to treat the undesirable tissue 48. The treat the undesirable tissue 48, the operator initially may locate the first electrode 24a at a first position and the second electrode 24b at a second position using endoscopic visualization and maintaining the undesirable tissue 48 within the field of view of the flexible endoscope 12. The first position may be near a perimeter edge of the undesirable tissue 48. Once the electrodes 24a,b are located into or proximate the undesirable tissue 48, the electrodes 24a,b may be energized with a first sequence of electrical pulses to deliver a first energy dose that is less than the necrotic threshold to induce thermal heating in the tissue surrounding the electrode/tissue interface. Once the temperature and/or pressure of the undesirable tissue 48 achieves a predetermined threshold, the electrodes 24a,b may be energized with a second sequence of electrical pulses to deliver a second energy dose equal to or greater than the necrotic threshold to induce cell necrosis in the tissue by irreversible electroporation to create a necrotic zone 65. For example, once the first and second electrodes 24a,b are located in the desired positions, the undesirable tissue 48 may be exposed to an electric field generated by energizing the first and second electrodes 24a,b with the energy source 14.

The electric field created by the first sequence of electrical pulses may have a magnitude, frequency, pulse width suitable to increase the temperature of the undesirable tissue to a predetermined threshold. The electric field created by the second sequence of electrical pulses may have a magnitude, frequency, and pulse width suitable to induce irreversible electroporation in the undesirable tissue 48 within the necrotic zone 65. Without wishing to be bound to any particular theory, it is believed that increasing the temperature of the undesirable tissue to a predetermined threshold may reduce the magnitude, frequency, and/or pulse width of the electric field suitable to induce irreversible electroporation in the undesirable tissue 48. The size of the necrotic zone may be substantially dependent on the size and separation of the electrodes 24a,b. The treatment time may be defined as the time that the electrodes 24a,b are activated or energized to generate the electric pulses suitable for inducing thermal heating and/or irreversible electroporation in the undesirable tissue 48.

This procedure may be repeated to destroy relatively larger portions of the undesirable tissue 48. At anytime, the surgeon or clinician may reposition the first and second electrodes 24a,b and begin the process anew. In other embodiments, the electrical ablation device may comprise multiple needle electrodes that may be employed to treat the undesirable tissue 48. Those skilled in the art will appreciate that similar techniques may be employed to ablate any other undesirable tissues that may be accessible trans-anally through the colon, and/or orally through the esophagus and the stomach using translumenal access techniques.

The embodiments of the electrical ablation devices described herein may be introduced inside a patient using minimally invasive or open surgical techniques. In some instances it may be advantageous to introduce the electrical ablation devices inside the patient using a combination of minimally invasive and open surgical techniques. Minimally invasive techniques may provide more accurate and effective access to the treatment region for diagnostic and treatment procedures. To reach internal treatment regions within the patient, the electrical ablation devices described herein may be inserted through natural openings of the body such as the mouth, anus, and/or vagina, for example. Minimally invasive procedures performed by the introduction of various medical devices into the patient through a natural opening of the patient are known in the art as NOTES™ procedures. Surgical devices, such as an electrical ablation devices, may be introduced to the treatment region through the channels of the endoscope to perform key surgical activities (KSA), including, for example, electrical ablation of tissues using irreversible electroporation energy. Some portions of the electrical ablation devices may be introduced to the tissue treatment region percutaneously or through small-keyhole-incisions.

Endoscopic minimally invasive surgical and diagnostic medical procedures are used to evaluate and treat internal organs by inserting a small tube into the body. The endoscope may have a rigid or a flexible tube. A flexible endoscope may be introduced either through a natural body opening (e.g., mouth, anus, and/or vagina). A rigid endoscope may be introduced via trocar through a relatively small-keyhole-incision incisions (usually 0.5 cm to 1.5 cm). The endoscope can be used to observe surface conditions of internal organs, including abnormal or diseased tissue such as lesions and other surface conditions and capture images for visual inspection and photography. The endoscope may be adapted and configured with channels for introducing medical instruments to the treatment region for taking biopsies, retrieving foreign objects, and/or performing surgical procedures.

Once an electrical ablation device is inserted in the human body internal organs may be reached using trans-organ or translumenal surgical procedures. The electrical ablation device may be advanced to the treatment site using endoscopic translumenal access techniques to perforate a lumen, and then, advance the electrical ablation device and the endoscope into the peritoneal cavity. Translumenal access procedures for perforating a lumen wall, inserting, and advancing an endoscope therethrough, and pneumoperitoneum devices for insufflating the peritoneal cavity and closing or suturing the perforated lumen wall are well known. During a translumenal access procedure, a puncture must be formed in the stomach wall or in the gastrointestinal tract to access the peritoneal cavity. One device often used to form such a puncture is a needle knife which is inserted through the channel of the endoscope, and which utilizes energy to penetrate through the tissue. A guidewire is then feed through the endoscope and is passed through the puncture in the stomach wall and into the peritoneal cavity. The needle knife is removed, leaving the guidewire as a placeholder. A balloon catheter is then passed over the guidewire and through the channel of the endoscope to position the balloon within the opening in the stomach wall. The balloon can then be inflated to increase the size of the opening, thereby enabling the endoscope to push against the rear of the balloon and to be feed through the opening and into the peritoneal cavity. Once the endoscope is positioned within the peritoneal cavity, numerous procedures can be performed through the channel of the endoscope.

The endoscope may be connected to a video camera (single chip or multiple chips) and may be attached to a fiber-optic cable system connected to a "cold" light source (halogen or xenon), to illuminate the operative field. The video camera provides a direct line-of-sight view of the treatment region. If working in the abdomen, the abdomen may be insufflated with carbon dioxide ($CO_2$) gas to create a working and viewing space. The abdomen is essentially blown up like a balloon (insufflated), elevating the abdominal wall above the internal organs like a dome. $CO_2$ gas is used because it is common to the human body and can be removed by the respiratory system if it is absorbed through tissue.

Once the electrical ablation devices are located at the target site, the diseased tissue may be electrically ablated or destroyed using the various embodiments of electrodes discussed herein. The placement and location of the electrodes can be important for effective and efficient electrical ablation therapy. For example, the electrodes may be positioned proximal to a treatment region (e.g., target site or worksite) either endoscopically or transcutaneously (percutaneously). In some implementations, it may be necessary to introduce the electrodes inside the patient using a combination of endoscopic, transcutaneous, and/or open techniques. The electrodes may be introduced to the tissue treatment region through a channel of the endoscope, an overtube, or a trocar and, in some implementations, may be introduced through percutaneously or through small-keyhole-incisions.

Preferably, the various embodiments of the devices described herein will be processed before surgery. First, a new or used instrument is obtained and if necessary cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that the device is sterilized prior to use. This can be done by any number of ways known to those skilled in the art including beta or gamma radiation, ethylene oxide, steam.

The various embodiments described herein may be better understood when read in conjunction with the following representative examples. The following examples are included for purposes of illustration and not limitation.

An ablation apparatus comprising two electrodes coupled to a energy source and a temperature sensor according to certain embodiments was used to deliver a series of electrical pulses ex vivo to healthy porcine liver to induce irreversible electroporation (Dose 1). In one embodiment, the Dose 1 pulse parameters may include a 3,000 V amplitude, a 10 μs pulse width, 10 total number of pulses per burst, a frequency of 200 Hz, 6 total number of bursts, and a 3 s delay between each burst. Dose 1 is generally characterized by low energy and high voltage. Dose 1 was not suitable for synchronizing to a patient's cardiac cycle. FIG. 13 is a photograph of the porcine liver after receiving Dose 1. The necrotic zone 100 is generally indicated by the discoloration of the tissue. The temperature was monitored using the temperature sensor illustrated in FIG. 4. FIG. 14 is a graphical representation of temperature during Dose 1. Without wishing to be bound to any particular theory, it is believed that temperature is related to the distance between the electrodes. As shown in FIG. 14, an electrode spacing of 1.5 cm generated a maximum temperature of about 51° C. at the positive electrode and an electrode spacing of 1.0 cm generated a maximum temperature of about 59° C. at the positive electrode. As shown in FIG. 14, the temperature increases as the distance between the electrodes decreases.

Figure 15A:
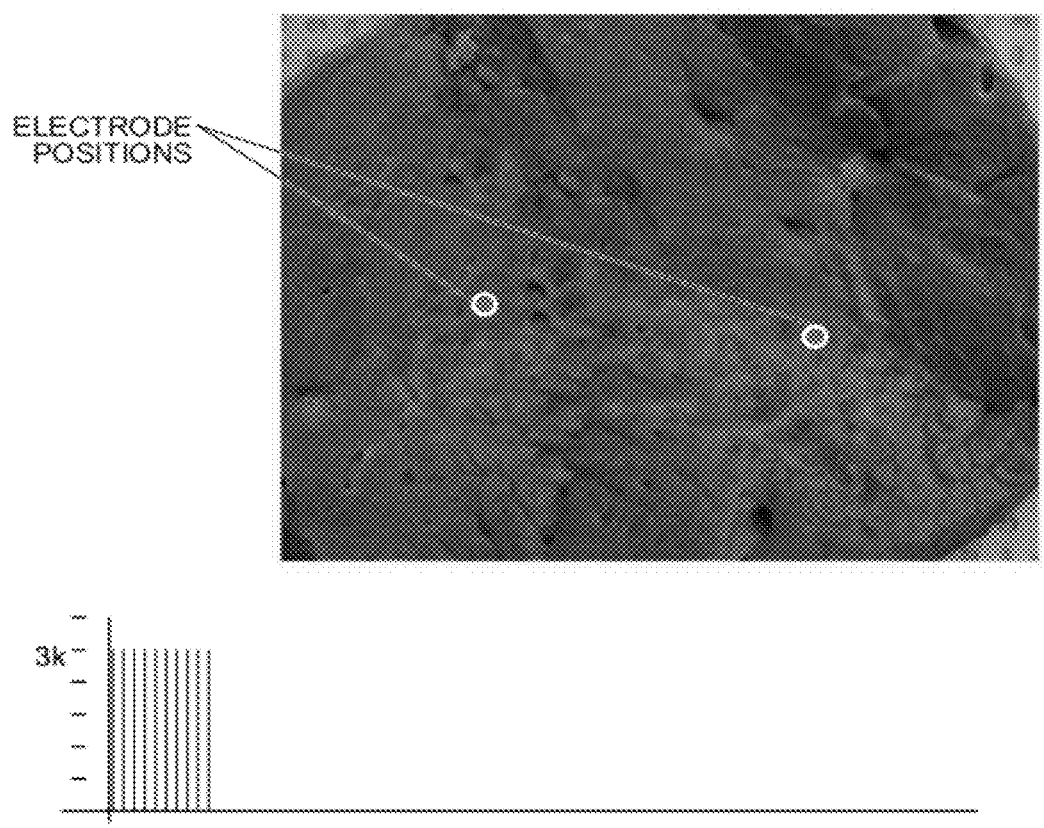
Figure 15B:
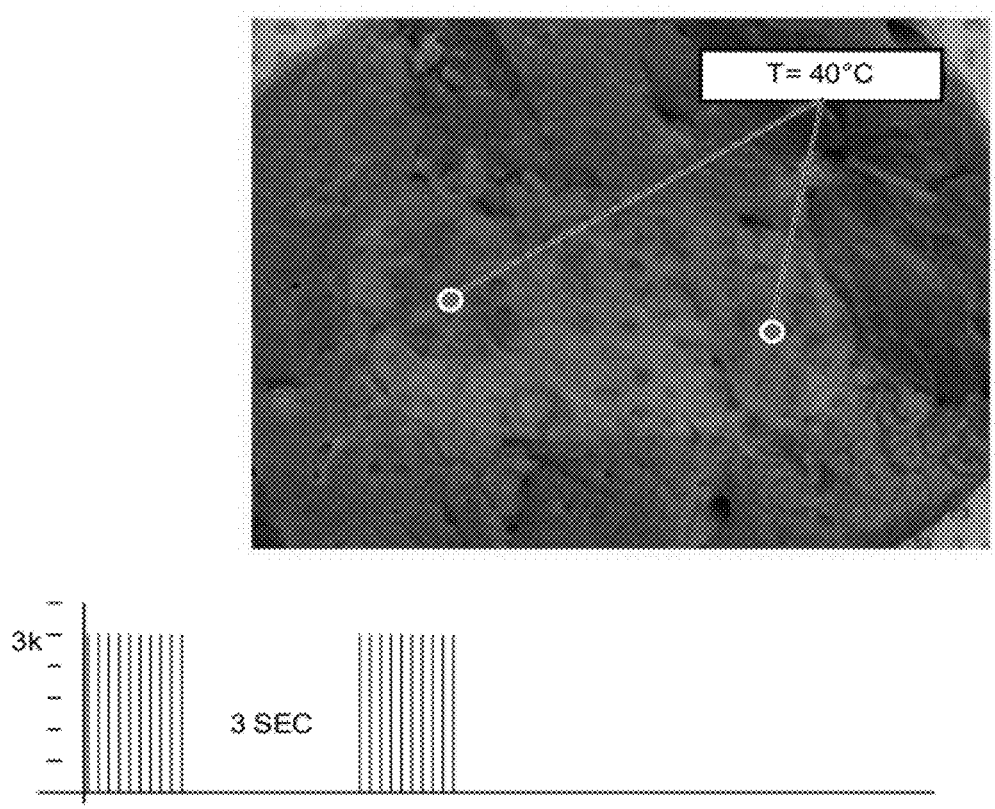
Figure 15C:
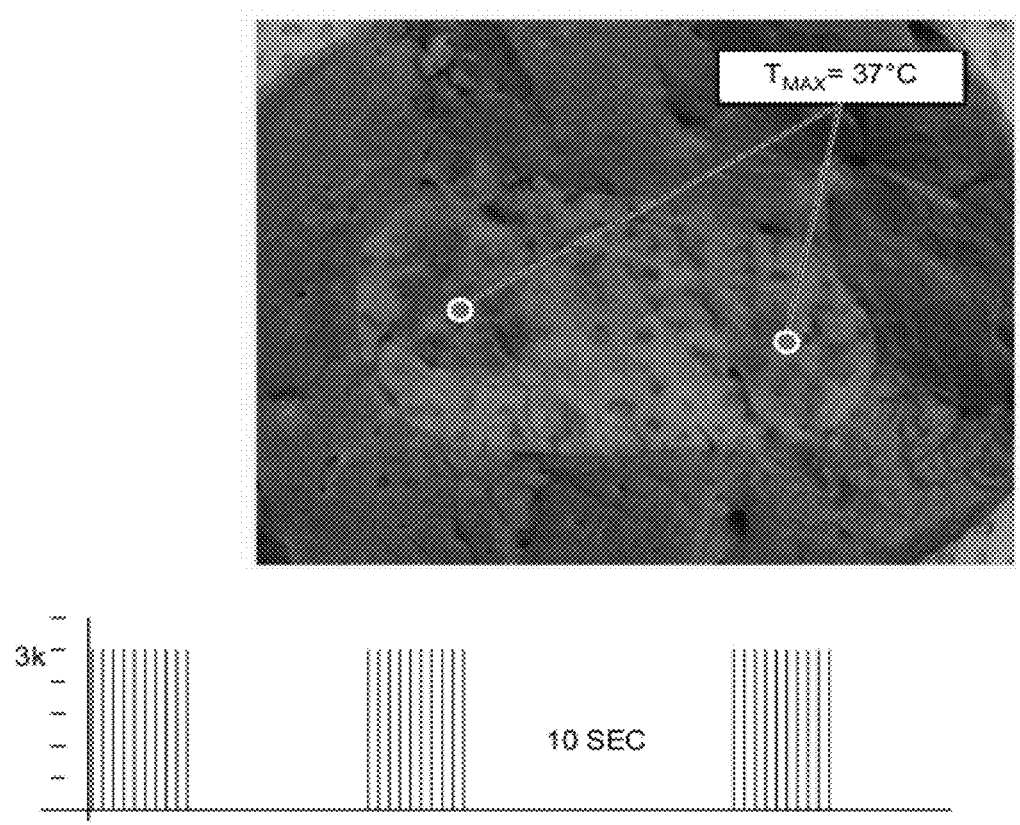
Figure 15D:
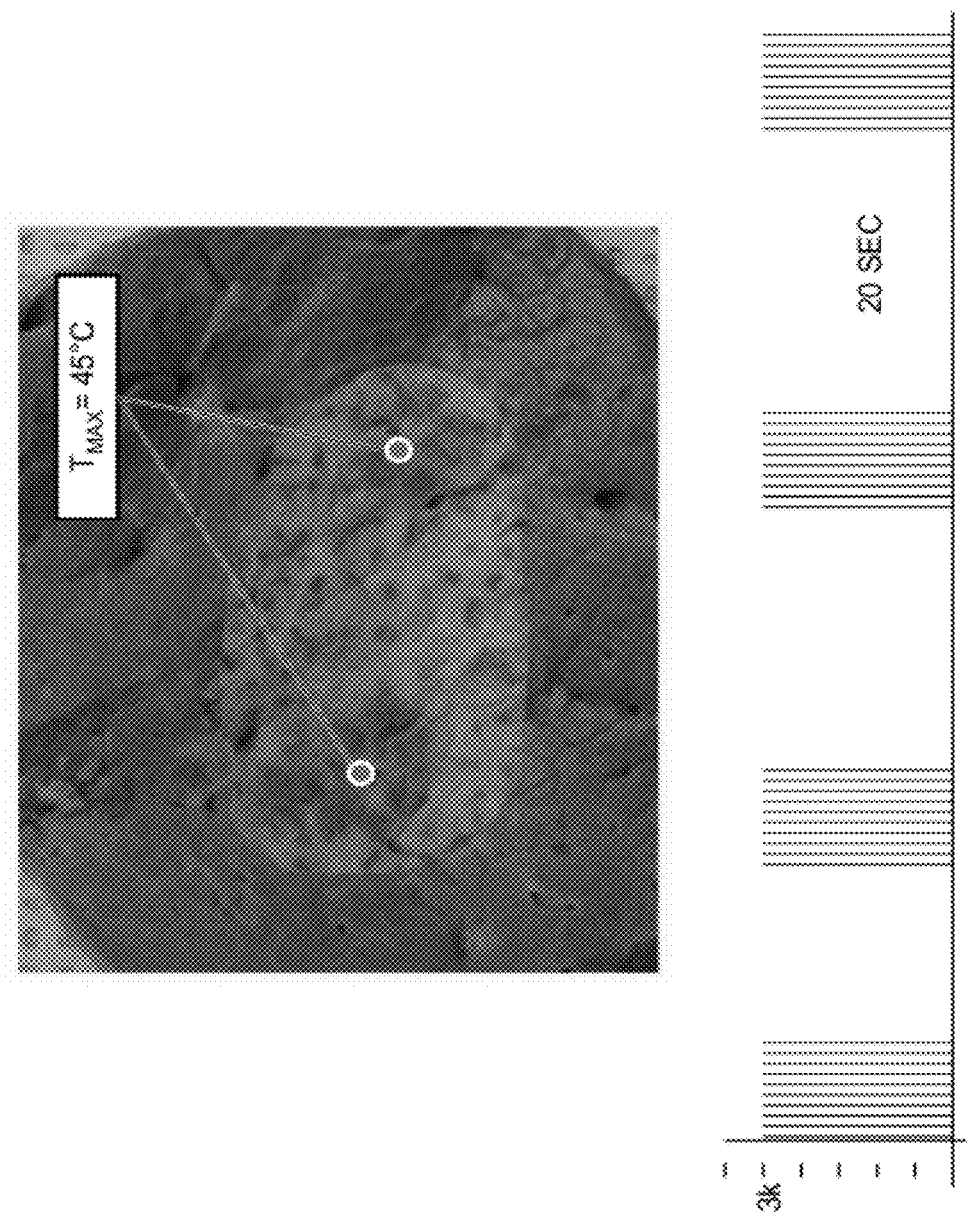

FIGS. 15A-D include photographs of porcine liver after receiving a series of electrical pulses having an amplitude of 3 kV that may be applied to undesirable tissue to induce irreversible electroporation. FIG. 15A is a photograph of porcine liver after receiving a first sequence of electrical pulses. FIG. 15B is a photograph of the porcine liver after receiving the second sequence of electrical pulses. The temperature of the porcine tissue after the second sequence of electrical pulses was 40° C. FIG. 15C is a photograph of the porcine liver after receiving the third sequence of electrical pulses. The temperature of the porcine tissue after the third sequence of electrical pulses was 37° C. FIG. 15D is a photograph of the porcine liver after receiving the fourth sequence of electrical pulses. The temperature of the porcine tissue after the fourth sequence of electrical pulses was 45° C. The necrotic zone caused by each sequence of electrical pulses is generally indicated by the discoloration of the tissue. The sequence interval between each series of electrical pulses was 5 seconds. The total dose time was 20 seconds.

An ablation apparatus comprising two electrodes coupled to a energy source and a temperature sensor according to certain embodiments was used to deliver a series of electrical pulses ex vivo to healthy porcine liver to induce irreversible electroporation (Dose 2). In one embodiment, the Dose 2 parameters may include a first series of bursts including a 1000 V amplitude, a 5 μs pulse width, 500 total number of pulses per burst, a total of 30 first series bursts, a 0.1 s delay between each burst followed by a second series of bursts pulses including a 1500 V amplitude, a 5 μs pulse width, 500 total number of pulses per burst, a total of 20 second bursts, a 0.1 s delay between each burst followed by a third series of bursts including a 3000 V amplitude, a 10 μs pulse width, 10 total number of pulses per burst, a total of 10 third series bursts, a 3 s delay between each burst. The frequency may be 200 Hz. Dose 2 is generally characterized by a multi-train dose at a higher energy than Dose 1. Dose 2 was not suitable for synchronizing to a patient's cardiac cycle. As shown in FIG. 16, the first pulse train included 500 pulses per burst at a pulse width of 5 μs, a frequency of 200 Hz, and an amplitude of 1 kV, the second pulse train included 500 pulses per burst at a pulse width of 5 μs, a frequency of 200 Hz, and an amplitude of 1.5 kV, and the third pulse train included 10 pulses per burst at a pulse width of 10 μs, a frequency of 200 Hz, and an amplitude of 3 kV.

The size and area of the necrotic zone of Dose 1 was compared to the size and area of the necrotic zone of Dose 2. FIG. 17 is a graph illustrating the average area of the necrotic zone for Dose 1 and the average area of the necrotic zone for Dose 2. As shown in FIG. 17, Dose 1 exhibited a smaller average area of the necrotic zone than Dose 2. FIG. 18A is a graph illustrating the average area of the necrotic zone for Dose 1 and the average area of the necrotic zone for Doses 2a,b. As shown in FIG. 18A, the average necrotic zone dimensions and area for Dose 1 was 1 cm×2.5 cm and 2.5 cm$^2$, respectively. The average necrotic zone dimensions and area for Dose 2 was 2.0 cm×3.67 cm and 7.34 cm$^2$, respectively. FIG. 18B includes photographs of the necrotic zone produced by Doses 1, 2a, and 2b. As shown in FIGS. 17 and 18, the size and area of the necrotic zone generally increases as the energy increases.

FIG. 19 is a graphical representation of a series of electrical pulses that may be delivered to undesirable tissue to induce irreversible electroporation. The multi-train electrical sequence may be synchronized with a patient's cardiac cycle. As shown in FIG. 19, the pulse train may include up to 180 pulses per burst at a pulse width of 10 μs, a frequency of 200 Hz, and an amplitude of 3 kV. The total burst time of each burst may fit within the latent period, or the period of electrical inactivity of the cardiac cycle. The latent period may also be known as the refractory period. The temperature may be measured between each burst. In one embodiment, the pulse parameters and maximum temperature may be adjusted to achieve a non-thermal zone of cell death ("IRE Dose"). The IRE Dose may include a maximum temperature of 50° C. and a typical sequence time of about 1 minute. In one embodiment, for example, the IRE Dose parameters may include a 3,000 V amplitude, a 10 μs pulse width, 15 total number of pulses per burst, frequency of each 10 μs pulse within the bursts of 200 Hz, a 3 s delay between each burst, and 20 total number of bursts. The IRE Dose may be characterized by no or reduced thermal damage to the tissue surrounding the electrode. In one embodiment, the pulse parameters and maximum temperature may be adjusted to slowly increase the temperature of the tissue ("IRE+ Dose"). The IRE+ Dose may increase the temperature of a large volume of tissue by a few degrees, such as, for example, 0-10° C. and 1-5° C., over a relatively longer period of time. The IRE+ Dose may include a typical sequence time of about 8 minutes. For example, the IRE+ Dose parameters may include a 3,000 V amplitude, a 10 μs pulse width, 20 total number of pulses per burst, frequency of each 10 μs pulse within the bursts of 200 Hz, a 3 s delay between each burst, and 90 total number of bursts at a maximum temperature of 60° C. The electrode spacing may be 2 cm. The IRE+ Dose may be characterized by a large necrosis zone. In one embodiment, the pulse parameters and maximum temperature may be adjusted to rapidly increase the temperature of the tissue ("IRE+Heat Dose"). The IRE+Heat Dose may increase the temperature of a large volume of tissue by a few degrees, such as, for example, 0-10° C. and 1-5° C., over a relatively shorter period of time. The IRE+Heat Dose may include a typical sequence time of about 4 minutes. In one embodiment, for example, the IRE+Heat Dose parameters may include a 3,000 V amplitude, a 10 μs pulse width, 20 total number of pulses per burst, frequency of each 10 μs pulse within the bursts of 200 Hz, a 0.1 s delay between each burst, and 90 total number of bursts at a maximum temperature of 60° C. The higher temperature in the tissue surrounding the electrodes may cause thermal coagulation. Without wishing to be bound to any particular theory, it is believed that thermal coagulation may occur at a higher average power and same energy. The IRE+Heat Dose may be characterized by a larger necrotic zone than the IRE Dose and a shorter time than the IRE+ Dose.

FIGS. 20A-C are photographs of a healthy porcine liver after receiving the IRE Dose, IRE+ Dose, and IRE+Heat Dose, respectively. As shown in the FIG. 20A, the IRE Dose has a necrotic zone having a size of 1.2 cm×2.3 cm and an area of 2.76 cm$^2$. As shown in the FIG. 20B, the IRE+ Dose has a necrotic zone having a size of 2.1 cm×3.7 cm and an area of 7.77 cm$^2$. As shown in the FIG. 20C, the IRE+Heat Dose has a necrotic zone having a size of 1.6 cm×3.6 cm and an area of 5.76 cm$^2$. The IRE+Heat Dose has a thermal zone located within the necrotic zone. The size and area of the thermal zone (lighter area) is smaller than the size and area of the necrotic zone.

Figure 21:
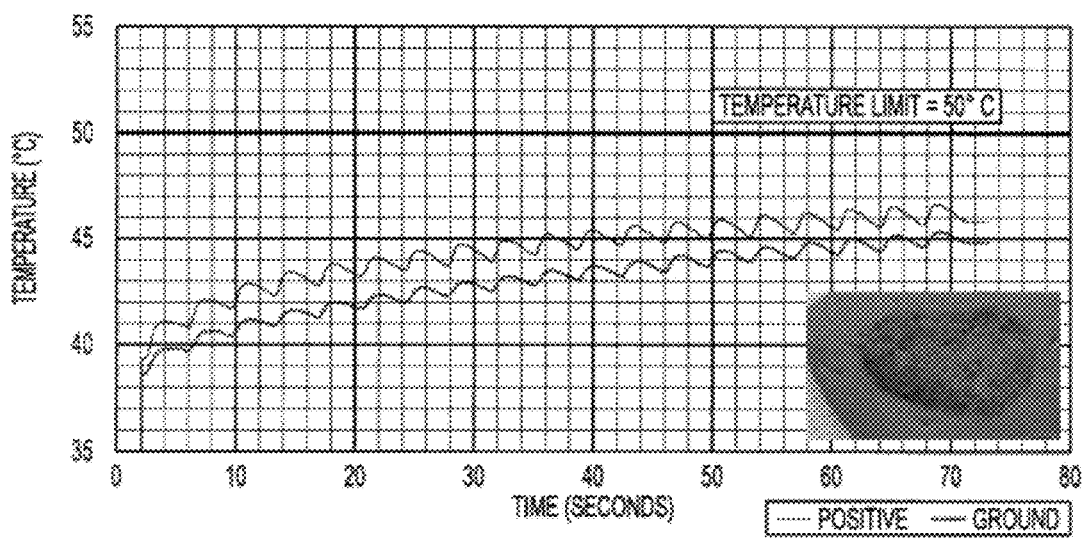
Figure 22:
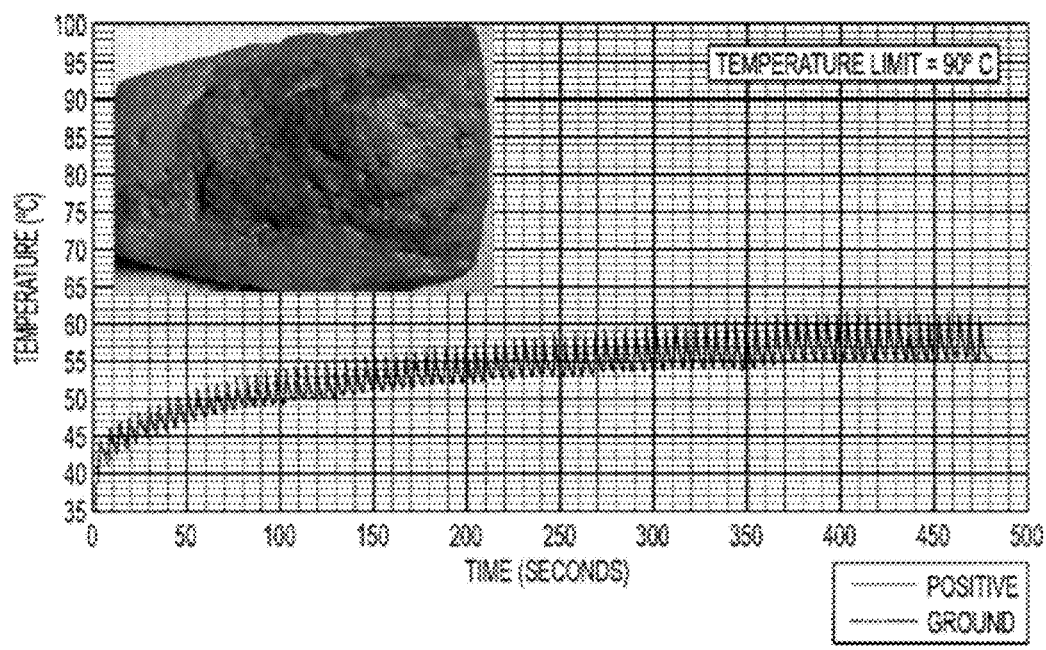
Figure 23:
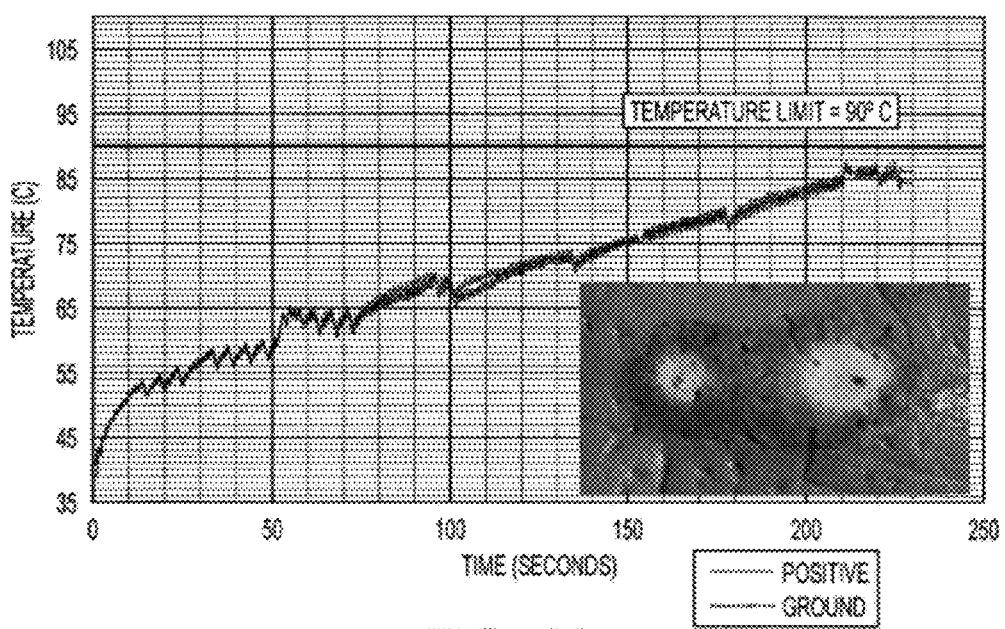
Figure 24:
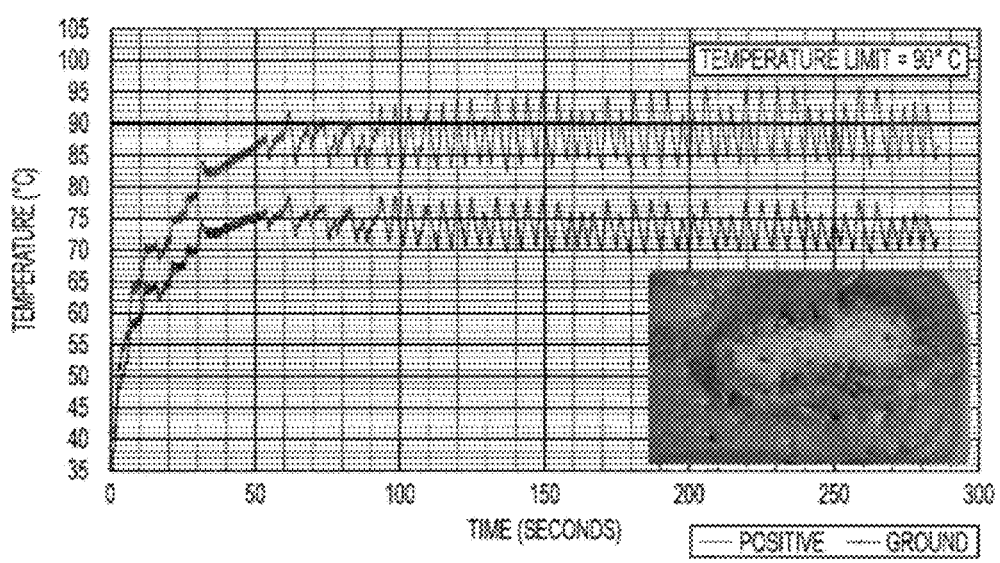

FIG. 21 is a graphical representation of the electrode temperature during the IRE Dose having a maximum temperature limit of 50° C. As shown in FIG. 21, the maximum temperature at the positive electrode was about 47° C. at 69 seconds. FIG. 22 is a graphical representation of the temperature during the IRE+ Dose having a maximum temperature limit of 90° C. As shown in FIG. 22, the maximum temperature at the positive electrode was about 62° C. at about 430 seconds. FIG. 23 is a graphical representation of the temperature during the IRE+Heat Dose having a maximum temperature limit of 90° C. As shown in FIG. 23, the maximum temperature at the positive electrode was about 88° C. at about 220 seconds. FIG. 24 is a graphical representation of the temperature during the IRE+Heat Dose having a maximum temperature limit of 90° C. As shown in FIG. 24, the maximum temperature at the positive electrode was about 96° C. at about 259 seconds.

The size and proportion of the necrosis zone may be also related to electrode spacing. FIGS. 25A-C include photographs of healthy porcine liver after receiving an IRE Dose having an electrode spacing of 1.5 cm, an IRE+ Dose having an electrode spacing of 2.0 cm, an IRE+Heat Dose having an electrode spacing of 2.0 cm. As shown in FIGS. 25A-C, the IRE+ Dose has the largest necrotic zone and the IRE Dose has the smallest necrotic zone. The IRE+Heat Dose has a necrotic zone intermediate the IRE Dose and IRE+ Dose. The IRE+ Heat Dose has a thermal zone (lighter area) is smaller than the necrotic zone.

Figure 26A:
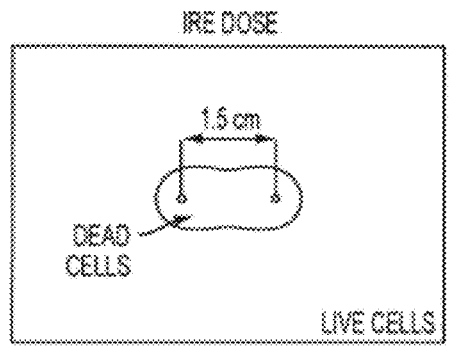
Figure 26B:
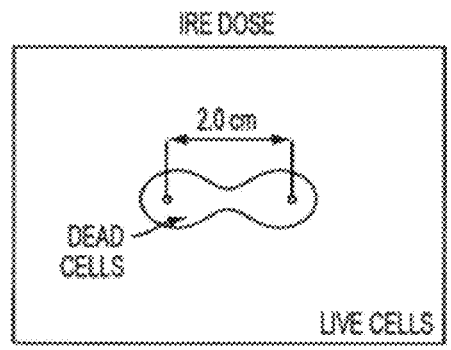
Figure 26C:
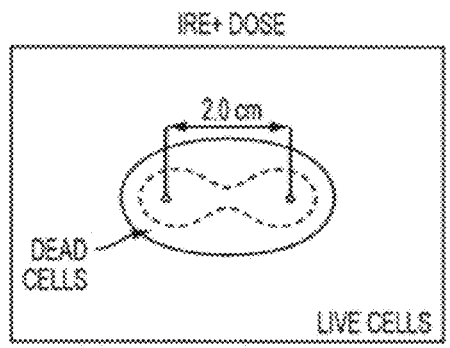
Figure 26D:
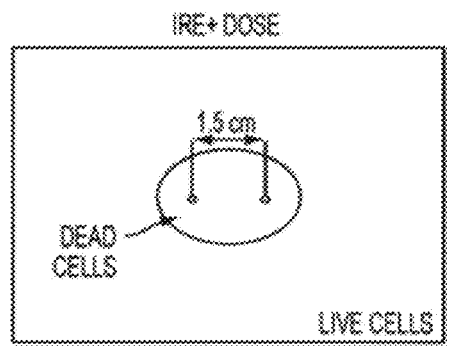
Figure 26E:
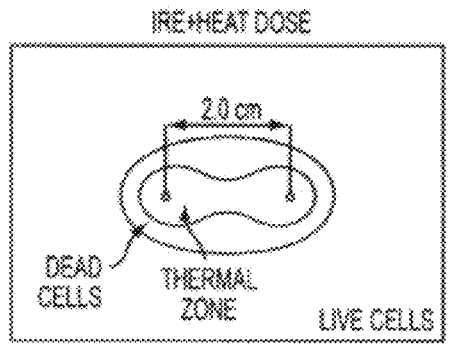
Figure 26F:
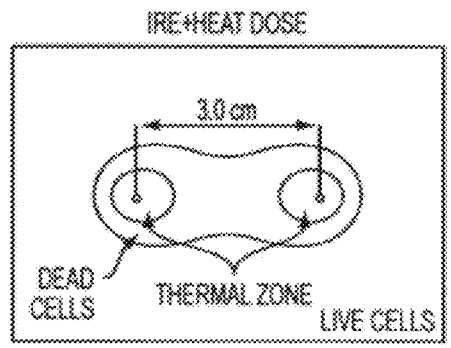

FIGS. 26A-F are graphical representations of simulated necrotic zones (white) and thermal zones (gray) of porcine livers (black) after receiving a series of electrical pulses that may be applied to undesirable tissue to induce irreversible electroporation according to certain embodiments described herein. FIGS. 26A,B include computer simulation of an IRE Dose having an electrode spacing of 1.5 cm and 2.0 cm, respectively. A necrotic zone of 2.3 cm×1.02 cm is predicted for an IRE Dose having an electrode spacing of 1.5 cm. A necrotic zone of 2.8 cm wide is predicted for an IRE Dose having an electrode spacing of 2.0 cm. FIGS. 26C,D include computer simulation of an IRE+ Dose having an electrode spacing of 1.5 cm and 2.0 cm, respectively. A necrotic zone of 3.4 cm×2.09 cm is predicted for an IRE+ Dose having an electrode spacing of 2.0 cm and a 400 V/cm threshold. A necrotic zone of 2.92 cm×2.04 cm is predicted for an IRE+ Dose having an electrode spacing of 1.5 cm and a 400 V/cm threshold. Without wishing to be bound to any particular theory, it is believed that decreasing the necrotic threshold may increase the size of the necrotic zone. As shown in FIGS. 26A,C, the size of the necrotic zone in FIG. 26A is smaller than the size of the necrotic zone in FIG. 26C. FIGS. 26E,F include computer simulation of an IRE+Heat Dose having an electrode spacing of 2.0 cm and 3.0 cm, respectively. As shown in FIG. 26E, an IRE+Heat Dose having an electrode spacing of 2.0 cm produces a thermal zone (gray region). The width of the necrotic zone of an IRE+Heat Dose having an electrode spacing of 2.0 cm is less than the width of the necrotic zone of an IRE+ Dose having an electrode spacing of 2.0 cm. As shown in FIG. 26F, an IRE+Heat Dose having an electrode spacing of 3.0 cm produces thermal zones around each electrode. The width of the necrotic zone of an IRE+ Heat Dose having an electrode spacing of 3.0 cm is less than the width of the necrotic zone of an IRE+Heat Dose having an electrode spacing of 2.0 cm. Without wishing to be bound to any particular theory, it is believed that the ratio of the necrotic zone length and necrotic zone width generally corresponds to the electric field pattern. The electric field pattern generally becomes long and narrow as the electrode spacing increases.

According to certain embodiments, the electrical ablation system may be configured to treat larger masses of tissue. As described above, the ablation apparatus may generally comprise a one or more electrodes, such as, for example, two, three, four, and five electrodes, configured to be positioned into or proximal to undesirable tissue in a tissue treatment region. The ablation apparatus may comprise a central electrode and an electrode array comprising a plurality of electrodes. The electrodes may be coupled to an energy source operative to independently generate and deliver a first sequence of electrical pulses to the electrode array and a second sequence of electrical pulses to the central electrode. The first sequence of electrical pulses to the electrode array may deliver a first energy dose that is less than the necrotic threshold to induce thermal heating in the tissue. The second sequence of electrical pulses to the central electrode may deliver a second energy dose equal to or greater than the necrotic threshold to induce cell necrosis in the tissue. In certain embodiments, the electrode array and central electrode may induce thermal heating and/or cell necrosis in larger masses of tissue relative to conventional electrical ablation therapies.

In various embodiments, the electrode array and central electrode may reduce the pain, trauma, and/or hemorrhaging associated with treating larger masses of undesirable tissue relative to conventional electrical ablation therapies. For example, in various embodiments, the electrode array may spread the heating more rapidly than conventional electrical ablation therapies by creating multiple heat sources. The surgeon or clinician may not need to reposition the electrical ablation apparatus within the tissue treatment region to treat large masses of undesirable tissue. Further, the relative positions and orientations of electrode array and central electrode may induce thermal heating and/or cell necrosis in larger masses of tissue of various shapes and sizes relative to conventional electrical ablation therapies.

In certain embodiments, an electrical ablation system may comprise an electrical ablation device comprising a relatively flexible member or shaft that may be introduced to the tissue treatment region using any of the techniques discussed above, such as, for example, an open incision and a trocar, through one or more of the channels of an endoscope, percutaneously, or transcuteously. The electrical ablation system may comprise an electrical ablation device comprising a central electrode and an electrode array. Referring to FIG. 27, in one embodiment, the central electrode 124a and the electrode array comprising a plurality of electrodes 124b may extend out from the distal end of the shaft 122 of the electrical ablation device. A sheath 126 may be slid over the flexible shaft 122. One or more of the plurality of electrodes of the electrode array and central electrode may be adapted and configured to slideably move in and out of a cannula, lumen, or channel formed with a flexible shaft, a working channel formed within a flexible shaft of the endoscope, or may be independently located independently of the endoscope. As described above, one or more of the electrodes may be fixed in place or provide a pivot about which other electrode(s) may be moved to other points in the tissue treatment region. As shown in FIG. 27, in a deployed state, an electrical ablation system comprising a central electrode 124a and the electrode array comprising a plurality of electrodes 124b may engage a greater area than an electrical ablation system comprising two electrodes.

When the electrode array and/or central electrode is positioned at the desired location into or proximate the tissue treatment region, the electrodes may be connected to or disconnected from the energy source by actuating or de-actuating an activation switch on the hand piece. The electrode array and central electrode may deliver electric field pulses to the undesirable tissue. As described above, the electrical field pulses may be characterized by various parameters, such as, for example, pulse shape, amplitude, frequency, pulse width, polarity, total number of pulses and duration. The electric field pulses delivered by the electrode array may be sufficient to induce thermal heating in the undesirable tissue without inducing irreversible electroporation in the undesirable tissue. The electric field pulses delivered by the central electrode may be sufficient to induce irreversible electroporation in the undesirable tissue. A ground pad may be positioned proximal to the tissue. A ground pad may be positioned adjacent to the tissue. The ground pad may serve as a return path for current from the generator through the electrodes.

In certain embodiments, the ablation system may comprise an energy source, as discussed above. The electrode array and central electrode may be coupled to the energy source. Once the energy source is coupled the electrode array and central electrode, an electric field may be independently formed at a distal end of one or more of the electrodes. The energy source may be configured to produce electrical energy suitable for thermal heating and/or electrical ablation. The energy source may be configured to independently produce electrical waveforms, such as, for example, RF waveforms, microwave waveforms, and/or ultrasonic waveforms, at predetermined frequencies, amplitudes, pulse widths and/or polarities suitable for thermal heating by the electrode array and electrical ablation by the central electrode. The energy source may be configured to produce destabilizing electrical potentials (e.g., fields) suitable to induce thermal heating by the electrode array and electrical ablation by the central electrode. The energy source may be configured to deliver electrical pulses in the form of DC and/or AC voltage potentials to the electrodes. As described above, a timing circuit may be coupled to the output of the energy source to generate electric pulses. As discussed above, the energy source may be configured to operate in either biphasic mode or monophasic mode. The energy source may comprise the controller.

In certain embodiments, the ablation system may comprise at least one controller configured to concurrently or sequentially operate the energy source. The controller may comprise a processor (e.g., a microprocessor), a central processing unit (CPU), a digital signal processor (DSP), an application-specific integrated circuit (ASIC), a field programmable gate array (FPGA) and any combinations thereof. The controller may comprise digital and/or analog circuit elements and electronics. In one embodiment, the controller may be configured to automatically control at least one parameter associated with the delivery of the electrical pulse. In one embodiment, the controller may be operably coupled to the energy source and configured to control at least one parameter associated with the delivery of the electrical pulse.

Referring to FIG. 28A, in certain embodiments, an electrical ablation system may comprise a controller 110 comprising a processor 105 and a memory 120. The controller 110 may comprise an analog-to-digital converter 125, an amplifier 130, and/or a pulse width modulator (not shown). The processor may be communicably coupled to the energy source (not shown) and configured to control at least one parameter associated with the delivery of the electrical pulse. The controller may execute instructions to implement the electrical ablation system. The electrical ablation system may comprise a general purpose computer 135 operably coupled to the controller 110 and programmed to control the controller 110.

Referring to FIG. 28B, in certain embodiments, an electrical ablation system may comprise a digital processing system 210. The digital processing system 210 may comprise a processor 205 and a memory 220. The digital processing system 210 may comprise an amplifier 230. The digital processing system 210 may comprise one or more embedded applications implemented as firmware, software, hardware, and any combination thereof. The digital processing system 210 may comprise various executable modules and/or blocks, such as, for example, software, programs, data, drivers, and application program interfaces. The digital processing system 210 may be communicably coupled to the energy source (not shown) and configured to control at least one parameter associated with the delivery of the electrical pulse. The digital processing system 210 may execute instructions to implement the electrical ablation system. The electrical ablation system may comprise a general purpose computer 235 operably coupled to the digital processing system 210 and programmed to control the digital processing system 210.

Referring to FIG. 28C, in certain embodiments, an electrical ablation system may comprise a controller 310 comprising an AC voltage source 305. The controller 310 may comprise an amplifier 330. The controller 310 may be communicably coupled to the energy source (not shown) and configured to control at least one parameter associated with the delivery of the electrical pulse. The controller 310 may execute instructions to implement the electrical ablation system. The electrical ablation system may comprise a general purpose computer 335 operably coupled to the controller 310 and programmed to control the controller 310.

In various embodiments, the controller and components thereof, such as the processor and memory, may comprise more than one separate functional element, such as various modules and/or blocks. Although certain modules and/or blocks may be described by way of example, it will be appreciated that a greater or lesser number of modules and/or blocks may be used and still fall within the scope of the embodiments. Further, although various embodiments may be described in terms of modules and/or blocks to facilitate the desired function, such modules and/or blocks may be implemented by one or more hardware components, e.g., processor, Complex Programmable Logic Device (CPLD), Digital Signal Processor (DSP), Programmable Logic Devices (PLD), Application Specific Integrated Circuit (ASIC), circuits, registers and/or software components, e.g., programs, subroutines, logic and/or combinations of hardware and software components.

In certain embodiments, an electrical ablation system may comprise one or more memories that, for example, store instructions or data, for example, volatile memory (e.g., Random Access Memory (RAM), Dynamic Random Access Memory (DRAM), or the like), non-volatile memory (e.g., Read-Only Memory (ROM), Electrically Erasable Programmable Read-Only Memory (EEPROM), Compact Disc Read-Only Memory (CD-ROM), or the like), persistent memory, or the like. Further non-limiting examples of one or more memories include Erasable Programmable Read-Only Memory (EPROM), flash memory, and the like. The one or more memories may be coupled to, for example, one or more controllers by one or more instruction, data, or power buses.

According to certain embodiments, a computer-implemented system for delivering energy to tissue having a necrotic threshold may generally comprise an electrode array comprising a plurality of electrodes, a central electrode, a ground pad, a processor, and a memory coupled to the processor and storing instructions to be executed by the processor to apply a first sequence of electrical pulses to the electrode array less than the necrotic threshold to induce thermal heating in the tissue, apply a second sequence of electrical pulses to the central electrode equal to or greater than the necrotic threshold to induce cell necrosis in the tissue by irreversible electroporation, and apply a ground potential to the ground pad. The ground pad may be adjacent to the tissue. The ground pad me be proximal to the tissue.

FIG. 27 shows one embodiment of an electrical ablation system after deploying the electrode array and central electrode. Each of the plurality of electrodes 124*b* may be spaced apart from the other of the plurality of electrodes 124*b*. The central electrode 124*a* may be positioned intermediate the plurality of electrodes 124*b*. The central electrode 124*a* may be centrally positioned intermediate the plurality of electrodes 124*b*. In various embodiments, the central electrode 124*a* may be aligned with the sheath 126. In other embodiments, the central electrode 124a may not be aligned with the sheath 126. In various embodiments, the distance from one or more of the plurality of electrodes 124b to the central electrode 124a may be from 0.1 cm to 5 cm, such as, for example, 1 cm, 1.5 cm, 2 cm, and 3 cm. In various embodiments, the distance from one or more of the plurality of electrodes 124b to one or more of the other of the plurality of electrodes 124b may be from 0.1 cm to 5 cm, such as, for example, 1 cm, 1.5 cm, 2 cm, and 3 cm. In various embodiments, the plurality of electrodes 124b of the electrode array may comprise outer electrodes and the central electrode 124a may comprise an inner electrode. The outer electrodes may surround the inner electrode. Each of the electrodes 124a,b may be spaced apart from the ground pad (not shown). In one embodiment, the ground pad may be replaced by one or more of the electrodes 124a,b.

In certain embodiments, the system may comprise an energy source coupled to the electrode array and the central electrode operative to generate and deliver the first sequence of electrical pulses and the second sequence of electrical pulses to tissue having a necrotic threshold. The electrode array and the central electrode may be independently adapted and configured to electrically couple to the energy source (e.g., generator, waveform generator). The energy source may comprise any of the energy sources described herein. The energy source may be configured to generate DC electric pulses at frequencies in the range of about 1 Hz to about 10,000 Hz, amplitudes in the range of about ±100 VDC to about ±6,000 VDC, and pulse width in the range of about 1 μs to about 100 ms. The energy source may be configured to generate electric pulses suitable to induce thermal heating and irreversible electroporation in the tissue. The energy source may be operated in biphasic mode and monophasic mode.

In certain embodiments, the system may comprise a controller, such as, for example, any of the controllers illustrated in FIGS. 28A-C. The controller may be coupled to the energy source and configured to control at least one parameter associated with the delivery of the electrical pulses. The at least one parameter may comprise frequency, amplitude, pulse width, polarity, voltage, total number of pulses, and delay between pulses bursts. For example, the controller may produce a series of m electric pulses of sufficient amplitude and duration less than the necrotic threshold to induce thermal heating in the tissue when m electric pulses are applied to the electrode array, and a series of n electric pulses of sufficient amplitude and duration to induce irreversible electroporation suitable for tissue ablation when n electric pulses are applied to the central electrode. In one embodiment, the energy source may comprise the controller.

In certain embodiments, the system may comprise instructions to be executed by the processor to deliver a first sequence of electrical pulses sufficient to create a thermal zone in a first portion of the tissue induced by thermal heating in an area near an electrode-tissue-interface of each of the plurality of electrodes of the electrode array, and a second sequence of electrical pulses sufficient to create a necrotic zone in a second portion of tissue induced by irreversible electroporation in an area surrounding both the central electrode and the plurality of electrodes of the electrode array. Referring to FIG. 29A, the first sequence of electrical pulses may create a thermal zone 500 in an area near the electrode-tissue-interface of one or more of the plurality of electrodes 524b of the electrode array. As shown in FIG. 29A, the plurality of electrodes 524b of the electrode array may comprise outer electrodes and the central electrode 524a may comprise an inner electrode aligned with the sheath 526. The current flowing from the outer electrodes 524b to the ground pad (i.e., return pad) may induce thermal heating in the tissue near the electrodes 524b. The thermal zone 500 of one of the electrodes 524b may not contact the thermal zone 500 of the other electrodes 524b. As shown in FIG. 29A, a thermal zone may not be created in an area near the electrode-tissue-interface of the central electrode 524a. In one embodiment, the system may comprise instructions to be executed by the processor to not deliver a sequence of electrical pulses to the central electrode to induce thermal heating when the electrical pulses are delivered to the electrode array. In one embodiment, the system may comprise instructions to be executed by the processor to deliver the first sequence of electrical pulses to the central electrode when the electrical pulses are delivered to the electrode array.

As shown in FIG. 29B, after a period of time, the thermal zone 500 of one or more of the electrodes 524b may contact the other electrodes 524b. In one embodiment, the thermal zone 500 of one or more of the electrodes 524b may contact the thermal zone 500 of one or more of the other electrodes 524b. The volume of the thermal zone 500 for one or more of the electrodes 524b may be from 1 cm$^3$ to 10 cm$^3$, 2 cm$^3$ to 8 cm$^3$, and 4 cm$^3$ to 6 cm$^3$. The total volume of the thermal zone 500 (i.e., the sum of each thermal zone) may be from 1 cm$^3$ to 50 cm$^3$, 4 cm$^3$ to 25 cm$^3$, and 10 cm$^3$ to 20 cm$^3$. The thermal zone 500 of one or more of the electrodes 524b may contact the central electrode 524a. The central electrode 524a may be positioned within the thermal zone 500. Referring to FIG. 29B, the central electrode 524a may be positioned into the tissue 501 outside the thermal zones 500. In certain embodiments, the central electrode 524a may be positioned into the tissue 501 within the thermal zone 500 even though the central electrode 524a did not induce the thermal zone 500. In various embodiments, the central electrode 524a may be positioned prior to forming the thermal zones 500 or after forming the thermal zones 500. The system may comprise instructions to be executed by the processor to not deliver a second sequence of electrical pulses to the electrode array sufficient to create a necrotic zone when the second sequence of electrical pulses is delivered to the central electrode.

In certain embodiments, the volume of the necrotic zone may be greater than or equal to the volume of the thermal zone. FIG. 30 is a finite element model of an electrical field in tissue 501 of an electrical ablation system according to certain embodiments. As shown in FIG. 30, the central electrode (524a) may comprise an inner electrode and the plurality of the electrodes (524b) may comprise outer electrodes. FIG. 31 is a graphical representation of an electric field strength of about 800 V/cm sufficient to induce irreversible electroporation at body temperature (about 37° C.). FIG. 32 is a graphical representation of an electric field strength of about 200 V/cm sufficient to induce irreversible electroporation at an elevated temperature (about 55° C.). Without wishing to be bound to any particular theory, it is believed that increasing the temperature of the tissue may reduce the electric field necessary to cause cell necrosis in the undesirable tissue. A comparison of FIGS. 31 and 32 shows that increasing the temperature of the tissue above body temperature (about 37° C.) reduced the electric field necessary to cause cell necrosis in the tissue. Additionally, the volume of the necrotic zone in FIG. 32 is greater than the volume of the necrotic zone in FIG. 31. As shown in FIG. 31, the volume of the necrotic zone in FIG. 31 does not contact each of the plurality of electrodes (524b) of the electrode array. As shown in FIG. 32, the volume of the necrotic zone in FIG. 32 contacts each of the plurality of electrodes and central electrode (524b).

In certain embodiments, the system may comprise instructions to be executed by the processor to form a pre-heated zone by applying an electric field that is less than about 800 V/cm by the first sequence of electrical pulses, and form a necrotic zone by applying an electric field that is greater than about 800 V/cm by the second sequence of electrical pulses. The system may comprise instructions to form a pre-heated zone by applying an electric field that is less than about 700 V/cm by the first sequence of electrical pulses, and form a necrotic zone by applying an electric filed that is equal to or greater than about 700 V/cm by the second sequence of electrical pulses. As discussed above, the shape of the pre-heated zone may be dependent on the position of the electrode array and ground pad. The pre-heated zone may be similar to the thermal zone discussed above. The shape of the necrotic zone may be dependent on the position of the central electrode and ground pad. The size of the pre-heated zone may be less than or equal to the size of the necrotic zone.

The shape and size of the thermal zone and/or necrotic zone may be controlled by the configuration and/or position of the central electrode, electrode array, the geometry of the electrodes, e.g., the length and width of each electrode, and the electrical pulses applied to the electrodes, and/or ground pad. For example, the size and shape of the thermal zone and/or necrotic zone may be changed by retracting or advancing the length of each electrode. In certain embodiments, the geometry of the central electrode and/or each of the plurality of electrodes may be one of parallel and non-parallel. The central electrode and electrode array may be configured to induce thermal heating and/or induce cell necrosis in large masses of tissue of various shapes and sizes by employing multiple electrodes.

In certain embodiments, the system may comprise instructions to be executed by the processor to heat the mass of tissue by applying an electric field that is less than about 800V/cm by the first sequence of electrical pulses to lower the necrotic threshold, and induce cell necrosis by irreversible electroporation by applying an electric filed that is greater than about 800 V/cm by the second sequence of electrical pulses. In one embodiment, the system may comprise instructions to be executed by the processor to heat the mass of tissue by applying an electric field that is less than about 700V/cm by the first sequence of electrical pulses to lower the necrotic threshold, and induce cell necrosis by irreversible electroporation by applying an electric filed that is greater than about 700 V/cm by the second sequence of electrical pulses.

In certain embodiments, the system may comprise instructions to be executed by the processor to apply a combination of a series of first electrical pulses having substantially lower voltage (in the range of 1000 V to 2000 V) to the electrode array to induce thermal heating, and a series of second electrical pulses having a higher voltage to the central electrode to induce cell necrosis. In one embodiment, a first series of pulses may be applied to create thermal zone to increase the temperature of the tissue and then a second series of pulses to induce cell necrosis at a lower voltage then otherwise would be necessary without the thermal heating of the tissue before inducing irreversible electroporation. In one embodiment, the system may comprise instructions to apply a combination of a series of first electrical pulses having substantially lower voltage to the electrode array to increase the size of the thermal zone at the same voltage.

In certain embodiments, the system may comprise instructions to be executed by the processor to apply a first sequence of electrical pulses to the electrode array less than the necrotic threshold to lower the necrotic threshold, and apply a second sequence of electrical pulses to the central electrode to induce cell necrosis by irreversible electroporation. In one embodiment, the system may comprise instructions to be executed by the processor to apply a first sequence of electrical pulses to the central electrode less than the necrotic threshold to lower the necrotic threshold when the first sequence of electrical pulses is applied to the electrode array. In one embodiment, the system may comprise instructions to be executed by the processor to not apply a second sequence of electrical pulses to the electrode array to induce cell necrosis by irreversible electroporation when the second sequence of electrical pulses is applied to the central electrode.

In certain embodiments, the system may comprise instructions to be executed by the processor to deliver a first energy dose that is less than the necrotic threshold to induce thermal heating by the first sequence of electrical pulses, and deliver a second energy dose equal to or greater than the necrotic threshold to induce cell necrosis in the tissue by irreversible electroporation by the second sequence of electrical pulses. As discussed above, FIG. 7 is a graphical representation of a first sequence of electrical pulses that deliver a first energy dose less than the necrotic threshold to induce thermal heating and a second sequence of electrical pulses that deliver a second energy dose to induce cell necrosis by irreversible electroporation. In one embodiment, the system may comprise instructions to be executed by the processor to deliver a first energy dose that is less than the necrotic threshold to the central electrode to induce thermal heating by the first sequence of electrical pulses. In one embodiment, the system may comprise instructions to be executed by the processor to not deliver an energy dose that is less than the necrotic threshold to the central electrode to induce thermal heating when the electrical pulses are delivered to the electrode array.

In certain embodiments, the system may comprise at least one of a temperature sensor and a pressure sensor adjacent at least one of the electrode array and central electrode. The temperature sensor may measure the temperature of the tissue surrounding one or more of the plurality of electrodes of the electrode array and/or central electrode. The pressure sensor may measure the pressure surrounding one or more of the plurality of electrodes of the electrode array and/or central electrode. In one embodiment, the apparatus may comprise at least one of a temperature sensor and a pressure sensor adjacent at least one of the electrode array and the central electrode. In one embodiment, the temperature sensor and/or pressure sensor may be located within one or more of the plurality of electrodes of the electrode array and/or central electrode. As discussed above, the pressure sensor may be adjacent to at least one of the vents in the shaft. In one embodiment, the pressure sensor may be adjacent at least one of the vents and the temperature sensor may be located at the distal end of the flexible shaft of the electrode array and/or central electrode. The energy source may be operative to generate and deliver the second sequence of electrical pulses to the central electrode when at least one of a predetermined temperature and a predetermined pressure is achieved.

In certain embodiments, the system may comprise instructions to be executed by the processor to apply a sequence of electrical pulses to the electrode array, the sequence of electrical pulses having amplitudes in the range of about ±100 VDC to about ±10,000 VDC, pulse widths in the range of about 1 μs to about 100 ms, and frequencies in the range of about 1 Hz to about 10,000 Hz, and re-apply the sequence of electrical pulses to the central electrode. In one embodiment, the energy source may be configured to generate and deliver DC first pulses and the second pulses at having amplitudes in the range of about ±100 VDC to about ±3,000 VDC, pulse widths in the range of about 1 μs to about 100 ms, and frequencies in the range of about 1 Hz to about 10,000 Hz. The sequence of electrical pulses may comprise a series of pulse trains each having a pulse train amplitude, a pulse train pulse width, and a pulse train frequency. The pulse trains may comprise a plurality of pulses each having an amplitude, a pulse width, and a frequency. The first sequence of electrical pulses may comprise a series of first pulse trains each having a first pulse train amplitude, a first pulse train pulse width, and a first pulse train frequency, and the second sequence of electrical pulses may comprise a series of second pulse trains each comprising a second pulse train amplitude, a second pulse train pulse width, and a second pulse train frequency.

Referring to FIG. 33, according to certain embodiments, a method for delivering energy to tissue having a necrotic threshold may generally comprise inserting an electrode array comprising a plurality of electrodes into the tissue (step 602), inserting a central electrode into the tissue (step 604), positioning a ground pad proximal to the tissue (step 606), applying a first sequence of electrical pulses to the electrode array less than the necrotic threshold to induce thermal heating in the tissue (step 608), applying a second sequence of electrical pulses to the central electrode equal to or greater than the necrotic threshold to induce cell necrosis in the tissue by irreversible electroporation (step 610), and applying a ground potential to the ground pad (step 612). The first sequence of electrical pulses may be applied to electrode array and the central electrode. The second sequence of electrical pulses may not be applied to the electrode array.

In certain embodiments, the method may comprise positioning each of the plurality of electrodes spaced apart from the other of the plurality of electrodes, and positioning the central electrode intermediate the plurality of electrodes. The user may position the electrode array and central array depending on the clinical conditions and/or clinical application. The user may consider the number of electrodes and the position of the electrodes relative to each other. The method may comprise independently positioning each of the plurality of electrodes of the electrode array at a first position, depth, and angle in the tissue, and positioning the central electrode at a second position, depth, and angle in the tissue. The first position, depth, and/or angle may be the same or different from the second position, depth, and/or angle. The method may comprise positioning one of the plurality of electrodes at the same or different position, depth, and/or angle of one or more of the other plurality of electrodes. The method may comprise positioning the plurality of electrodes spaced apart from the other of the plurality of electrodes. The method may comprise positioning the central electrode intermediate the plurality of electrodes. In one embodiment, the method may comprise positioning each of the electrodes of the electrode array as an outer electrode and positioning the central electrode as an inner electrode.

In certain embodiments, the method may generally comprise coupling the electrode array and the central electrode to an energy source operative to generate the first sequence of electrical pulses and the second sequence of electrical pulses. In various embodiments, the first sequence of electrical pulses may be sufficient to create at least one thermal zone in a portion of the tissue induced by thermal heating in an area near an electrode-tissue-interface of each of the plurality of electrodes, and the second sequence of electrical pulses may be sufficient to create a necrotic zone in a portion of tissue induced by irreversible electroporation in an area surrounding each of the plurality of electrodes and the central electrode. The thermal zone of one of the plurality of electrodes may contact the thermal zone of one or more of the other of the plurality of electrodes. The thermal zone of at least one of the plurality of electrodes may contact the central electrode. The thermal zone of each of the plurality of electrodes may contact the central electrode. The thermal zone of each of the plurality of electrodes may not contact the central electrode. The central electrode may be positioned within the thermal zone of each of the plurality of electrodes. The central electrode may be positioned outside the thermal zone of each of the plurality of electrodes. The volume of the necrotic zone may be greater than or equal to the volume of the thermal zone.

In certain embodiments, the method may generally comprise forming a pre-heated zone by applying an electric field that is less than about 800 V/cm by the first sequence of electrical pulses, and forming a necrotic zone by applying an electric filed that is greater than about 800 V/cm by the second sequence of electrical pulses. The method may comprise forming a pre-heated zone by applying an electric field that is less than about 700 V/cm by the first sequence of electrical pulses, and forming a necrotic zone by applying an electric filed that is greater than about 700 V/cm by the second sequence of electrical pulses. The electrode array and central electrode may be independently activated by the generator. In certain embodiments, the volume and/or geometry of the thermal zone and/or necrotic zone may be tailored to the clinical application. The relative positions and orientations of the electrodes may enable different shapes and sizes of volumes of the pre-heated zone and/or necrotic zone. The shape and size of the volume of pre-heated zone and/or necrotic zone may be controlled by the configuration and/or position of the electrode array and/or central electrode, the geometry of the electrodes, and parameters associated with the delivery of the electrical pulse. The size of the pre-heated zone may be less than or equal to the size of the necrotic zone.

In certain embodiments, the method may generally comprise heating the tissue by applying an electric field that is less than about 800V/cm by the first sequence of electrical pulses to lower the necrotic threshold, and inducing cell necrosis by irreversible electroporation by applying an electric filed that is greater than about 800 V/cm by the second sequence of electrical pulses. The method may comprise heating the tissue by applying an electric field that is less than about 700V/cm by the first sequence of electrical pulses to lower the necrotic threshold, and inducing cell necrosis by irreversible electroporation by applying an electric filed that is greater than about 700 V/cm by the second sequence of electrical pulses.

In certain embodiments, the method may generally comprise applying a first sequence of electrical pulses to the electrode array less than the necrotic threshold to lower the necrotic threshold, and applying a second sequence of electrical pulses to the central electrode to induce cell necrosis by irreversible electroporation. The method may comprise applying the first sequence of electrical pulses to the central electrode when the first sequence of electrical pulses is applied to the electrode array. The method may comprise applying the second sequence of electrical pulses to the electrode array when the second sequence of electrical pulses is applied to the central electrode. The method may comprise not applying the second sequence of electrical pulses to the electrode array when the second sequence of electrical pulses is applied to the central electrode.

In certain embodiments, the method may generally comprise delivering a first energy dose to the tissue that is less than the necrotic threshold to induce thermal heating by the first sequence of electrical pulses, and delivering a second energy dose to the tissue equal to or greater than the necrotic threshold to induce cell necrosis in the tissue by irreversible electroporation by the second sequence of electrical pulses. The first energy dose may be delivered by the electrode array and/or central electrode. The first energy dose may not be delivered by the central electrode. The second energy dose may be delivered by the central electrode. In one embodiment, the first energy dose may be delivered by the electrode array and the second energy dose may be delivered by the central electrode.

In certain embodiments, the method may generally comprise measuring at least one of temperature and pressure adjacent at least one of the electrode array and central electrode, applying a first sequence of electrical pulses to the electrode array to achieve at least one of a predetermined temperature and a predetermined pressure, and applying a second sequence of electrical pulses to the central electrode when the at least one of a predetermined temperature and a predetermined pressure is achieved. The predetermined temperature may be body temperature, about 37° C., and greater than 37° C., such as, for example, 40° C. to 60° C., 40° C. to 50° C., 40° C. to 55° C. and up to 60° C. The temperature of the tissue after the first sequence electrical pulses may be greater that body temperature, such as, for example, 37° C. The temperature of the tissue after the first sequence of electrical pulses may be about 55° C. The first and second sequences of electrical pulses may be configured to maintain the tissue at a temperature between 50-60° C. The predetermined pressure may be atmospheric pressure.

In certain embodiments, the method may generally comprise applying a sequence of electrical pulses to the electrode array, the sequence of electrical pulses having amplitudes in the range of about ±100 VDC to about ±10,000 VDC, pulse widths in the range of about 1 μs to about 100 ms, and frequencies in the range of about 1 Hz to about 10,000 Hz, and re-applying the sequence of electrical pulses to the central electrode. Each of the pulses may independently have amplitudes in the range of about ±100 VDC to about ±10,000 VDC, pulse widths in the range of about 1 μs to about 100 ms, and frequencies in the range of about 1 Hz to about 10,000 Hz. In one embodiment, the method may generally comprise applying a sequence of electrical pulses having amplitudes in the range of about ±100 VDC to about ±3,000 VDC, pulse widths in the range of about 1 μs to about 100 ms, and frequencies in the range of about 1 Hz to about 10,000 Hz. The sequence of electrical pulses may comprise a series of pulse trains each having a pulse train amplitude, a pulse train pulse width, and a pulse train frequency. The pulse trains may comprise a plurality of pulses each having an amplitude, a pulse width, and a frequency. As discussed above, the first sequence of electrical pulses may comprise a series of first pulse trains each having a first pulse train amplitude, a first pulse train pulse width, and a first pulse train frequency, and the second sequence of electrical pulses may comprise a series of second pulse trains each comprising a second pulse train amplitude, a second pulse train pulse width, and a second pulse train frequency.

In certain embodiments, the method may generally comprise lowering the necrotic threshold by heating the tissue by applying an electric field that is less than about 800 V/cm by the first sequence of electrical pulses. The method may comprise lowering the necrotic threshold by 30% by heating the tissue by applying an electric field that is less than about 800 V/cm. The method may comprise lowering the necrotic threshold by heating the tissue by applying an electric field that is less than about 700 V/cm by the first sequence of electrical pulses.

Once positioned by the user, at least one of the plurality of electrodes in the electrode array may be energized to form a pre-heated zone having a first shape in the tissue treatment region. The electrode array may be inserted into a tissue treatment region to create a plurality of pre-heated zones having a plurality of shapes by retracting the at least one of the plurality of electrodes in the electrode array, rotating at least one of the plurality of electrodes in the electrode array to a new location, advancing or retracting at least one of the plurality of electrodes in the electrode array into the tissue treatment region, and/or energizing or de-energizing at least one of the plurality of electrodes in the electrode array. For example, the shape of the pre-heated zone may be dependent on the position of the plurality of electrodes in the electrode array. When the central electrode is energized, a necrotic zone having a second shape may be formed in the tissue treatment region. This process may be repeated as often as necessary to create any number of necrotic zones using the electrical ablation apparatus.

Various parameters, such as, for example, pressure, temperature, and duration, may be altered or adjusted according to the type of tissue in the tissue treatment region and the desired size of the pre-heated zone and/or necrotic zone. The size of the pre-heated zone may be less than or equal to the size of the necrotic zone. In one embodiment, the ablation apparatus may increase the size of the necrotic zone relative to a similar ablation apparatus comprising a first sequence of electrical pulses to induce cell necrosis in the tissue by irreversible electroporation. At anytime, the surgeon or clinician may reposition the electrical ablation apparatus within the tissue treatment region and begin the process anew.

According to certain embodiments, the method may comprise applying a first sequence of electrical pulses to the electrode array to induce thermal heating and applying a second sequence of electrical pulses to the central electrode to induce cell necrosis by irreversible electroporation, wherein the first and second sequences of electrical pulses create a ratio of thermal volume to non-thermal volume of 5 to 1. The thermal volume may comprise the volume of the pre-heated zone. In one embodiment, at least one of the first sequence of electrical pulses, the second sequence of electrical pulses, and sequence interval may be configured to create a ratio of thermal volume to non-thermal volume of 2 to 1. In one embodiment, at least one of the first sequence of electrical pulses, the second sequence of electrical pulses, and sequence interval may be configured to create a ratio of thermal zone volume to necrotic zone volume of 1 to 1.

According to certain embodiments, the method may comprise measuring at least one of temperature and pressure of the tissue treatment region. The method may comprise measuring at least one of temperature and pressure of the undesirable tissue. The method may comprise measuring at least one of temperature and pressure adjacent at least one of the plurality of electrodes of the electrode array and the central electrode. The method may comprise measuring at least one of temperature and pressure adjacent at least one of the plurality of electrodes of the electrode array and the central electrode and applying a sequence of electrical pulses when at least one of a predetermined temperature and a predetermined pressure is achieved. The method may comprise measuring at least one of temperature and pressure adjacent at least one of the plurality of electrodes of the electrode array and the central electrode and stopping a sequence of electrical pulses when at least one of a predetermined temperature and a predetermined pressure is achieved. The method may comprise measuring at least one of temperature and pressure adjacent at least one of the plurality of electrodes of the electrode array and the central electrode and applying a sequence of electrical pulses to achieve at least one of a predetermined temperature and a predetermined pressure.

In one embodiment, the electrical ablation system comprising an electrode array and a central electrode may be used to deliver energy to tissue, such as, for example, undesirable tissue located on the surface of the liver. In use, the electrical ablation device may be introduced into or proximate the tissue treatment region through a port of a trocar. The trocar may be introduced into the patient via a small incision formed in the skin. The endoscope may be introduced into the patient trans-anally through the colon, trans-orally down the esophagus and through the stomach using translumenal techniques, or through a small incision or keyhole formed through the patient's abdominal wall (e.g., the peritoneal wall). The endoscope may be employed to guide and locate the distal end of the electrical ablation device into or proximate the undesirable tissue. Prior to introducing the flexible shaft through the trocar, the sheath may be slid over the flexible shaft in a direction toward the distal end thereof to cover each of the electrodes of the electrode array and central electrode until the distal end of the electrical ablation device reaches the undesirable tissue.

Once the electrical ablation device has been suitably introduced into or proximate the undesirable tissue, the sheath may be retracted to expose the at least one of the plurality of electrodes of the electrode array and/or central electrode to deliver energy to the undesirable tissue. To deliver the energy to the undesirable tissue, the operator initially may locate the each of the electrodes of the electrode array at a first position and the central electrode at a second position using endoscopic visualization and maintaining the undesirable tissue within the field of view of the flexible endoscope. The first position may be near a perimeter edge of the undesirable tissue. Once the electrodes are located into or proximate the undesirable tissue, the electrode array may be energized with a first sequence of electrical pulses to deliver a first energy dose that is less than the necrotic threshold to induce thermal heating in the tissue surrounding the electrode/tissue interface. Once the temperature and/or pressure of the undesirable tissue achieves a predetermined threshold, the central electrode may be energized with a second sequence of electrical pulses to deliver a second energy dose equal to or greater than the necrotic threshold to induce cell necrosis in the tissue by irreversible electroporation to create a necrotic zone. For example, once the electrode array and central electrode are located in the desired positions, the undesirable tissue may be exposed to an electric field generated by independently energizing the electrodes with the energy source.

According to certain embodiments, an ablation apparatus for delivering energy to tissue having a necrotic threshold may generally comprise an electrode array comprising a plurality of electrodes and a central electrode coupled to an energy source operative to generate and deliver a first sequence of electrical pulses to the electrode array and a second sequences of electrical pulses to the electrode array, wherein the first sequence of electrical pulses delivers a first energy dose to the tissue that is less than the necrotic threshold to induce thermal heating in the tissue and the second sequence of electrical pulses delivers a second energy dose to the tissue equal to or greater than the necrotic threshold to induce cell necrosis in the tissue by irreversible electroporation. The ablation apparatus may comprise a ground pad. The ground pad may be positioned proximal to or adjacent the tissue. The ablation apparatus may comprise a controller, including any of the controllers discussed herein. The controller may be coupled to the energy source and configured to control at least one parameter associated with the delivery of the electrical pulses. In various embodiments, each of the plurality of electrodes may comprise outer electrodes spaced apart from the other of the plurality of electrodes, and the central electrode may comprise an inner electrode intermediate the plurality of electrodes.

According to certain embodiments, an ablation apparatus may comprise an energy source configured to generate and deliver DC first pulses and the second pulses at frequencies in the range of 1 Hz to 10,000 Hz, amplitudes in the range of ±100 VDC to ±3000 VDC, and pulse width in the range of about 1 µs to about 100 ms. The first sequence of electrical pulses may be sufficient to create a thermal zone in a first portion of the tissue induced by thermal heating in an area near an electrode-tissue-interface of each of the plurality of electrodes, and the second sequence of electrical pulses may be sufficient to create a necrotic zone in a second portion of tissue induced by irreversible electroporation in an area surrounding each of the plurality of electrodes and the central electrode.

According to certain embodiments, a method of treating tissue may generally comprise obtaining an ablation apparatus comprising a central electrode and an electrode array coupled to an energy source operative to generate and deliver a first sequence of electrical pulses and a second sequence of electrical pulses to tissue having a necrotic threshold, wherein the first sequence of electrical pulses deliver a first energy dose that is less than the necrotic threshold to induce thermal heating in the tissue and the second sequence of electrical pulses deliver a second energy dose equal to or greater than the necrotic threshold to induce cell necrosis in the tissue by irreversible electroporation, inserting the electrode array into a mass of tissue having a necrotic threshold, applying a first sequence of electrical pulses to the electrode array less than the necrotic threshold to induce thermal heating, applying a second sequence of electrical pulses to the central electrode to induce cell necrosis by irreversible electroporation, and applying a ground potential to a ground pad, wherein the ablation apparatus is operative to reduce the necrotic threshold of the tissue relative to a corresponding ablation apparatus having an energy source configured to deliver a sequence of electrical pulses to induce cell necrosis by irreversible electroporation.

According to certain embodiments, a method of treating tissue may generally comprise inserting a central electrode and an electrode array comprising a plurality of electrodes into a mass of tissue having a membrane potential and a necrotic threshold, applying a first sequence of electrical pulses to the electrode array less than the necrotic threshold to induce thermal heating, applying a second sequence of electrical pulses to the central electrode to induce cell necrosis by irreversible electroporation, and applying a ground potential to a ground pad proximal to the tissue. In one embodiment, the method may comprise re-applying the sequence of electrical pulses to the central electrode. In one embodiment, an energy source may be operative to generate and deliver a sequence interval between the first sequence and second sequence. The first sequence of electrical pulses may comprise a series of first pulse trains each having a first pulse train amplitude, a first pulse train pulse width, and a first pulse train frequency, and the second sequence of electrical pulses may comprise a series of second pulse trains each comprising a second pulse train amplitude, a second pulse train pulse width, and a second pulse train frequency. The first pulse trains may comprise a plurality of first pulses each having a first amplitude, a first pulse width, and a first frequency, and each of the second pulse trains may comprise a plurality of second pulses each having a second amplitude, a second pulse width, and a second frequency. Each of the first pulses and the second pulses may independently have amplitudes in the range of about ±100 VDC to about ±10,000 VDC, pulse widths in the range of about 1 μs to about 100 ms, and frequencies in the range of about 1 Hz to about 10,000 Hz.

Although the various embodiments of the devices have been described herein in connection with certain disclosed embodiments, many modifications and variations to those embodiments may be implemented. For example, different types of end effectors may be employed. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A method for delivering energy to tissue having a necrotic threshold, the method comprising:
    inserting an electrode array comprising a plurality of electrodes into the tissue;
    inserting a central electrode into the tissue;
    positioning a ground pad proximal to the tissue;
    applying a first sequence of electrical pulses to the electrode array less than the necrotic threshold to induce thermal heating in the tissue;
    applying a second sequence of electrical pulses to the central electrode equal to or greater than the necrotic threshold to induce cell necrosis in the tissue by irreversible electroporation; and
    applying a ground potential to the ground pad.

2. The method of claim 1 comprising coupling the electrode array and the central electrode to an energy source operative to generate the first sequence of electrical pulses and the second sequence of electrical pulses.

3. The method of claim 1 comprising positioning each of the plurality of electrodes spaced apart from the other of the plurality of electrodes, and positioning the central electrode intermediate the plurality of electrodes.

4. The method of claim 1 comprising applying the first sequence of electrical pulses to the central electrode.

5. The method of claim 1, wherein the second sequence of electrical pulses is not applied to the electrode array.

6. The method of claim 1, wherein the first sequence of electrical pulses is sufficient to create at least one thermal zone in a portion of the tissue induced by thermal heating in an area near an electrode-tissue-interface of each of the plurality of electrodes, and wherein the second sequence of electrical pulses is sufficient to create a necrotic zone in a portion of tissue induced by irreversible electroporation in an area surrounding each of the plurality of electrodes and the central electrode.

7. The method of claim 6, wherein the thermal zone of each of the plurality of electrodes contacts the thermal zone of the other of the plurality of electrodes.

8. The method of claim 6, wherein the thermal zone of at least one of the plurality of electrodes contacts the central electrode.

9. The method of claim 6, wherein the thermal zone of each of the plurality of electrodes contacts the central electrode.

10. The method of claim 6, wherein the central electrode is positioned within the thermal zone of each of the plurality of electrodes.

11. The method of claim 6, wherein the volume of the necrotic zone is greater than the volume of the thermal zone.

12. The method of claim 6, wherein the thermal zone has a volume of about 4 cm$^3$ to about 6 cm$^3$.

13. The method of claim 6, wherein the thermal zone has a temperature greater than about 37° C.

14. The method of claim 6, wherein the thermal zone has a temperature of about of 55° C.

15. The method of claim 1 comprising:
    delivering a first energy dose to the tissue that is less than the necrotic threshold to induce thermal heating by the first sequence of electrical pulses; and
    delivering a second energy dose to the tissue equal to or greater than the necrotic threshold to induce cell necrosis in the tissue by irreversible electroporation by the second sequence of electrical pulses.

16. The method of claim 1 comprising:
    forming a pre-heated zone by applying an electric field that is less than about 800 V/cm by the first sequence of electrical pulses; and
    forming a necrotic zone by applying an electric field that is greater than about 800 V/cm by the second sequence of electrical pulses.

17. The method of claim 1 comprising:
    heating a mass of tissue by applying an electric field that is less than about 800V/cm by the first sequence of electrical pulses to lower the necrotic threshold; and
    inducing cell necrosis by irreversible electroporation by applying an electric field that is greater than about 800 V/cm by the second sequence of electrical pulses.

18. The method of claim 1 comprising:
    applying the first sequence of electrical pulses to the electrode array less than the necrotic threshold to lower the necrotic threshold; and
    applying the second sequence of electrical pulses to the central electrode to induce cell necrosis by irreversible electroporation.

19. The method of claim 1 comprising:
    lowering the necrotic threshold by heating the tissue by applying an electric field that is less than about 800 V/cm by the first sequence of electrical pulses.

20. The method of claim 1 comprising:
    measuring at least one of temperature and pressure adjacent at least one of the electrode array and central electrode;
    applying the first sequence of electrical pulses to the electrode array to achieve at least one of a predetermined temperature and a predetermined pressure; and
    applying the second sequence of electrical pulses to the central electrode when the at least one of the predetermined temperature and the predetermined pressure is achieved.

21. The method of claim 1 comprising:
    applying a sequence of electrical pulses to the electrode array, the sequence of electrical pulses having amplitudes in the range of about ±100 VDC to about ±10,000 VDC, pulse widths in the range of about 1 μs to about 100 ms, and frequencies in the range of about 1 Hz to about 10,000 Hz; and
    re-applying the sequence of electrical pulses to the central electrode.

22. A method for delivering energy to tissue having a necrotic threshold, the method comprising:
- inserting an electrode array comprising a plurality of electrodes into the tissue;
- inserting a central electrode into the tissue;
- measuring at least one of temperature and pressure in the tissue adjacent at least one of the electrode array and central electrode;
- applying a first sequence of electrical pulses to the electrode array less than the necrotic threshold to induce thermal heating in the tissue until at least one of a predetermined temperature and a predetermined pressure is achieved; and
- applying a second sequence of electrical pulses to the central electrode equal to or greater than the necrotic threshold to induce cell necrosis in the tissue by irreversible electroporation when the at least one of the predetermined temperature and the predetermined pressure is achieved.

23. A method for delivering energy to tissue having a necrotic threshold, the method comprising:
- inserting an electrode array comprising a plurality of electrodes into the tissue;
- inserting a central electrode into the tissue;
- applying a first sequence of electrical pulses to the electrode array less than the necrotic threshold to induce thermal heating and lower the necrotic threshold in the tissue; and
- applying a second sequence of electrical pulses to the central electrode equal to or greater than the necrotic threshold to induce cell necrosis in the tissue by irreversible electroporation.

* * * * *